United States Patent
Kaditz et al.

(10) Patent No.: US 10,222,441 B2
(45) Date of Patent: *Mar. 5, 2019

(54) TENSOR FIELD MAPPING

(71) Applicant: Q Bio, Inc, Millbrae, CA (US)

(72) Inventors: Jeffrey Howard Kaditz, Wilson, WY (US); Athanasios Polymeridis, Moscow (RU); Jorge Fernandez Villena, Somerville, MA (US)

(73) Assignee: Q Bio, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/362,808

(22) Filed: Nov. 28, 2016

(65) Prior Publication Data
US 2017/0285123 A1 Oct. 5, 2017

Related U.S. Application Data

(63) Continuation-in-part of application No. 15/089,571, filed on Apr. 3, 2016, now Pat. No. 9,958,521, and a
(Continued)

(51) Int. Cl.
*G01N 24/08* (2006.01)
*G01R 33/48* (2006.01)
(Continued)

(52) U.S. Cl.
CPC ......... *G01R 33/5608* (2013.01); *G01N 24/08* (2013.01); *G01R 33/48* (2013.01);
(Continued)

(58) Field of Classification Search
USPC .......................... 324/300–322; 600/407–435
See application file for complete search history.

(56) References Cited

U.S. PATENT DOCUMENTS

| 4,729,892 A | 3/1988 | Beall |
| 5,619,138 A * | 4/1997 | Rourke ............... G01R 33/446 324/309 |

(Continued)

FOREIGN PATENT DOCUMENTS

| WO | 2014205275 A1 | 12/2014 |
| WO | WO-2015183792 | 12/2015 |
| WO | WO-2016073985 | 5/2016 |

OTHER PUBLICATIONS

International Search Report and Written Opinion dated Nov. 28, 2016 re PCT/US16/51204.
(Continued)

*Primary Examiner* — Melissa Koval
*Assistant Examiner* — Tiffany Fetzner
(74) *Attorney, Agent, or Firm* — Aurora Consulting LLC; Steven Stupp; Ashley Sloat

(57) ABSTRACT

During operation, a system may apply an external magnetic field and an RF pulse sequence to a sample. Then, the system may measure at least a component of a magnetization associated with the sample, such as MR signals of one or more types of nuclei in the sample. Moreover, the system may calculate at least a predicted component of the magnetization for voxels associated with the sample based on the measured component of the magnetization, a forward model, the external magnetic field and the RF pulse sequence. Next, the system may solve an inverse problem by iteratively modifying the parameters associated with the voxels in the forward model until a difference between the predicted component of the magnetization and the measured component of the magnetization is less than a predefined value. Note that the calculations may be performed concurrently with the measurements and may not involve performing a Fourier transform.

23 Claims, 15 Drawing Sheets

Related U.S. Application Data continuation-in-part of application No. 15/169,719, filed on May 31, 2016.

(51) Int. Cl.

| | | |
|---|---|---|
| *G01R 33/465* | (2006.01) | |
| *G01R 33/56* | (2006.01) | |
| G01R 33/44 | (2006.01) | |
| G01R 33/563 | (2006.01) | |

(52) U.S. Cl.
CPC .......... *G01R 33/448* (2013.01); *G01R 33/465* (2013.01); *G01R 33/4804* (2013.01); *G01R 33/5602* (2013.01); *G01R 33/56358* (2013.01)

(56) References Cited

U.S. PATENT DOCUMENTS

| | | | |
|---|---|---|---|
| 5,793,210 A | 8/1998 | Pla et al. | |
| 6,084,408 A | 7/2000 | Chen | |
| 6,148,272 A | 11/2000 | Bergstrom et al. | |
| 6,392,409 B1 | 5/2002 | Chen | |
| 6,678,669 B2 | 1/2004 | Lapointe | |
| 7,924,002 B2* | 4/2011 | Lu | G01R 33/243 324/307 |
| 7,940,927 B2 | 5/2011 | Futa et al. | |
| 7,974,942 B2 | 7/2011 | Pomroy | |
| 8,427,157 B2* | 4/2013 | Fautz | G01R 33/246 324/309 |
| 8,432,165 B2 | 4/2013 | Weiger | |
| 8,502,532 B2* | 8/2013 | Assmann | G01R 33/56375 324/307 |
| 8,686,727 B2 | 4/2014 | Reddy et al. | |
| 8,723,518 B2 | 5/2014 | Seiberlich et al. | |
| 8,736,265 B2 | 5/2014 | Boernert et al. | |
| 9,046,589 B2* | 6/2015 | Gjesdal | A61B 5/055 |
| 9,192,322 B2* | 11/2015 | Wong | A61B 5/055 |
| 9,513,359 B2* | 12/2016 | Koch | G01R 33/56563 |
| 9,514,169 B2 | 12/2016 | Mattson | |
| 9,958,521 B2* | 5/2018 | Kaditz | G01R 33/48 |
| 2002/0155587 A1 | 10/2002 | Opalsky | |
| 2002/0177771 A1 | 11/2002 | Guttman et al. | |
| 2003/0210043 A1 | 11/2003 | Freedman | |
| 2005/0137476 A1 | 6/2005 | Welland | |
| 2005/0181466 A1 | 8/2005 | Dambinova | |
| 2008/0065665 A1 | 3/2008 | Pomroy | |
| 2008/0081375 A1 | 4/2008 | Tesiram et al. | |
| 2008/0082834 A1 | 4/2008 | Mattson | |
| 2008/0129298 A1* | 6/2008 | Vaughan | G01R 33/5612 324/322 |
| 2009/0315561 A1* | 12/2009 | Assmann | G01R 33/56375 324/309 |
| 2010/0131518 A1 | 5/2010 | Elteto | |
| 2010/0141252 A1* | 6/2010 | Fautz | G01R 33/246 324/307 |
| 2010/0142823 A1 | 6/2010 | Wang et al. | |
| 2010/0177188 A1 | 7/2010 | Kishima | |
| 2010/0189328 A1 | 7/2010 | Boernert et al. | |
| 2010/0244827 A1 | 9/2010 | Hennel | |
| 2010/0306854 A1 | 12/2010 | Neergaard | |
| 2011/0095759 A1 | 4/2011 | Bhattacharya et al. | |
| 2011/0166484 A1 | 7/2011 | Virta | |
| 2012/0124161 A1 | 5/2012 | Tudwell et al. | |
| 2012/0271157 A1* | 10/2012 | Wong | A61B 5/0042 600/419 |
| 2013/0271133 A1* | 10/2013 | Snyder | G01R 33/56 324/309 |
| 2013/0275718 A1 | 10/2013 | Ueda | |
| 2013/0294669 A1 | 11/2013 | El-Baz | |
| 2013/0338930 A1 | 12/2013 | Senegas | |
| 2014/0039300 A1* | 2/2014 | Gjesdal | A61B 5/055 600/420 |
| 2014/0062475 A1* | 3/2014 | Koch | G01R 33/56563 324/309 |
| 2014/0107469 A1* | 4/2014 | Gjesdal | A61B 5/055 600/420 |
| 2014/0336998 A1 | 11/2014 | Cecchi | |
| 2015/0003706 A1 | 1/2015 | Eftestol et al. | |
| 2015/0032421 A1 | 1/2015 | Dean et al. | |
| 2015/0040225 A1 | 2/2015 | Coates et al. | |
| 2015/0089574 A1 | 3/2015 | Mattson | |
| 2016/0007968 A1 | 1/2016 | Sinkus | |
| 2016/0127123 A1 | 5/2016 | Johnson | |
| 2017/0007148 A1* | 1/2017 | Kaditz | A61B 5/055 |
| 2017/0011255 A1* | 1/2017 | Kaditz | G01R 33/48 |
| 2017/0011514 A1 | 1/2017 | Westerhoff | |
| 2017/0038452 A1* | 2/2017 | Trzasko | G01R 33/56572 |
| 2017/0285122 A1* | 10/2017 | Kaditz | G01R 33/445 |

OTHER PUBLICATIONS

International Search Report and Written Opinion dated Sep. 19, 2016 re PCT/US16/040578.

International Search Report and Written Opinion dated Sep. 19, 2016 re PCT/US16/040215.

Hasenkam et al. "Prosthetic Heart Valve Evaluation by Magnetic Resonance Imaging." European Journal of Cardio-Thoracic Surgery 1999, pp. 300-305, 16, [Retrieved Aug. 25, 2016] <http://ejcts.oxfordjournals.org/content/16/3/300.full.pdf+html>.

Nestares, et al. "Robust Multiresolution Alignment of MRI Brain Volumes." Magnetic Resonance in Medicine 2000, pp. 705-715, [Retrieved Aug. 27, 2016] <http://web.mit.edu/ImagingPubs/Coregistration/nestares_heeger_coreg.pdf>.

G. Schultz, "Magnetic Resonance Imaging with Nonlinear Gradient Fields: Signal Encoding and Image Reconstruction" Springer Verlag, New York, 2013), Chapter 2, pp. 1-10.

International Application Serial No. PCT/US2017/035071, International Search Report dated Aug. 22, 2017, 2 pgs.

Siemens. Magnetic Resonance Imaging. (Dec. 2012) [retrieved on Jun. 27, 2017, https://w5.siemens.com/web/us/ru/medecine/detection_diagnosis/magnetic_resonans/035-15-MRI-scaners/Documents/mri-magnetom-family_brochure-00289718.pdf] 15 pgs.

International Application Serial No. PCT/US2017/035073, Written Opinion dated Aug. 11, 2017, 6 pgs.

International Application Serial No. PCT/US2017/022842, International Search Report dated May 23, 2017, 2 pgs.

International Application Serial No. PCT/US2017/035071, Written Opinion dated Aug. 22, 2017, 7 pgs.

Gualda et al. SPIM-fluid: open source light-sheet based platform for high-throughput imaging. Biomed Opt Express (Nov. 1, 2015) vol. 6, No. 11, pp. 4447-4456.

International Application Serial No. PCT/US2017/022842, Written Opinion dated May 23, 2017, 4 pgs.

International Application Serial No. PCT/US2017/022911, International Search Report dated Jul. 19, 2017, 4 pgs.

International Application Serial No. PCT/US2017/022911, Written Opinion dated Jul. 19, 2017, 10 pgs.

International Application Serial No. PCT/US2017/035073, International Search Report dated Aug. 11, 2017, 2 pgs.

I. Kononenko "Machine learning for medical diagnosis: history, state of the art and perspective" Artificial Intelligence in Medicine 23 (2001) 21 pgs.

Kwan et al: "MRI Simulation-Based Evaluation of Image-Processing and Classification Methods" IEEE Transactions on Medical Imaging. vol. 18 No. 11, Nov. 1999, 13 pgs.

* cited by examiner

TENSOR FIELD MAPPING

CROSS-REFERENCE TO RELATED APPLICATION

This application claims priority under 35 U.S.C. § 120 to: U.S. Non-Provisional application Ser. No. 15/089,571, entitled "Field-Invariant Quantitative Magnetic-Resonance Signatures," by Jeffrey H. Kaditz and Andrew G. Stevens, filed on 3 Apr. 2016; and U.S. Non-Provisional application Ser. No. 15/169,719, entitled "Fast Scanning Based on Magnetic-Resonance History," by Jeffrey H. Kaditz and Andrew G. Stevens, filed on 31 May 2016, the contents of each of which are hereby incorporated by reference.

This application also claims priority under 35 U.S.C. § 119(e) to: U.S. Provisional Application Ser. No. 62/189,675, entitled "Systems and Method for Indexed Medical Imaging of a Subject Over Time," by Jeffrey H. Kaditz and Andrew G. Stevens, filed on Jul. 7, 2015; U.S. Provisional Application Ser. No. 62/213,625, entitled "Systems and Method for Indexed Medical Imaging of a Subject Over Time," by Jeffrey H. Kaditz and Andrew G. Stevens, filed on Sep. 3, 2015; U.S. Provisional Application Ser. No. 62/233,291, entitled "Systems and Method for Indexed Medical Imaging of a Subject Over Time," by Jeffrey H. Kaditz and Andrew G. Stevens, filed on Sep. 25, 2015; U.S. Provisional Application Ser. No. 62/233,288, entitled "Systems and Method for Indexed Medical and/or Fingerprinting Tissue," by Jeffrey H. Kaditz and Andrew G. Stevens, filed on Sep. 25, 2015; U.S. Provisional Application Ser. No. 62/245,269, entitled "System and Method for Auto Segmentation and Generalized MRF with Minimized Parametric Mapping Error Using A Priori Knowledge," by Jeffrey H. Kaditz, filed on Oct. 22, 2015; U.S. Provisional Application Ser. No. 62/250,501, entitled "System and Method for Auto Segmentation and Generalized MRF with Minimized Parametric Mapping Error Using A Priori Knowledge," by Jeffrey H. Kaditz, filed on Nov. 3, 2015; U.S. Provisional Application Ser. No. 62/253,128, entitled "System and Method for Auto Segmentation and Generalized MRF with Minimized Parametric Mapping Error Using A Priori Knowledge," by Jeffrey H. Kaditz, filed on Nov. 9, 2015; U.S. Provisional Application Ser. No. 62/255,363, entitled "System and Method for Auto Segmentation and Generalized MRF with Minimized Parametric Mapping Error Using A Priori Knowledge," by Jeffrey H. Kaditz, filed on Nov. 13, 2015; and U.S. Provisional Application Ser. No. 62/281,176, entitled "System and Method for Auto Segmentation and Generalized MRF with Minimized Parametric Mapping Error Using A Priori Knowledge," by Jeffrey H. Kaditz, filed on Jan. 20, 2016, the contents of each of which are herein incorporated by reference.

BACKGROUND

Field

The described embodiments relate generally to determining one or more physical parameters associated with a sample by iteratively converging measurements of a physical phenomenon associated with the sample with a forward model that predicts the physical phenomenon based on the one or more physical parameters.

Related Art

Many non-invasive characterization techniques are available for determining one or more physical parameters of a sample. For example, magnetic properties can be studied using magnetic resonance or MR (which is often referred to as 'nuclear magnetic resonance' or NMR), a physical phenomenon in which nuclei in a magnetic field absorb and re-emit electromagnetic radiation. Moreover, density variations and short or long-range periodic structures in solid or rigid materials can be studied using characterization techniques such as x-ray imaging, x-ray diffraction, computed tomography, neutron diffraction or electron microscopy, in which electromagnetic waves or energetic particles having small de Broglie wavelengths are absorbed or scattered by the sample. Furthermore, density variations and motion in soft materials or fluids can be studied using ultrasound imaging, in which ultrasonic waves are transmitted and reflected in the sample.

In each of these characterization techniques, one or more external excitation (such as a flux of particles or incident radiation, static or time-varying scalar fields, and/or static or time-varying vector fields) are applied to the sample, and a resulting response of the sample, in the form a physical phenomenon, is measured. As an example, in MR magnetic nuclear spins may be partially aligned (or polarized) in an applied external DC magnetic field. These nuclear spins may precess or rotate around the direction of the external magnetic field at an angular frequency (which is sometimes referred to as the 'Larmor frequency') given by the product of a gyromagnetic ratio of a type of nuclei and the magnitude or strength of the external magnetic field. By applying a perturbation to the polarized nuclear spins, such as one or more radio-frequency (RF) pulses (and, more generally, electro-magnetic pulses) having pulse widths corresponding to the angular frequency and at a right-angle or perpendicular to the direction of the external magnetic field, the polarization of the nuclear spins can be transiently changed. The resulting dynamic response of the nuclear spins (such as the time-varying total magnetization) can provide information about the physical and material properties of a sample, such as one or more physical parameters associated with the sample.

In general, each of the characterization techniques may allow one or more physical parameters to be determined in small volumes or voxels in a sample, which can be represented using a tensor. Using magnetic resonance imaging (MRI) as an example, the dependence of the angular frequency of precession of nuclear spins (such as protons or the isotope $^1H$) on the magnitude of the external magnetic field can be used to determine images of three-dimensional (3D) or anatomical structure and/or the chemical composition of different materials or types of tissue. In particular, by applying a non-uniform or spatially varying magnetic field to a sample or a patient, the resulting variation in the angular frequency of precession of $^1H$ spins is typically used to spatially localize the measured dynamic response of the $^1H$ spins to voxels, which can be used to generate images, such as of the internal anatomy of a patient.

However, the characterization of the physical properties of a sample is often time-consuming, complicated and expensive. For example, acquiring MR images in MRI with high-spatial resolution (i.e., small voxels sizes) often involves a large number of measurements (which are sometimes referred to as 'scans') to be performed for time durations that are longer than the relaxation times of the $^1H$ spins in different types of tissue in a patient. Moreover, in order to achieve high-spatial resolution, a large homogenous external magnetic field is usually used during MRI. The external magnetic field is typically generated using a superconducting magnetic having a toroidal shape with a narrow bore, which can feel confining to many patients. Furthermore, Fourier transform techniques may be used to facilitate image reconstruction, at the cost of constraints on the RF pulse sequences and, thus, the scan time.

The combination of long scan times and, in the case of MRI, the confining environment of the magnet bore can degrade the user experience. In addition, long scan times reduce throughput, thereby increasing the cost of performing the characterization.

SUMMARY

A group of embodiments relate to a system that determines parameters associated with a sample. The system includes: a generating device that generates magnetic fields; a measurement device that performs measurements; a memory that stores a program module; and a processor that executes the program module. During operation, the system may apply an external magnetic field and an RF pulse sequence to the sample. Then, the system may measure at least a component of a magnetization associated with the sample. Moreover, the system may calculate at least a predicted component of the magnetization for voxels associated with the sample based on the measured component of the magnetization, a forward model, the external magnetic field and the RF pulse sequence. Next, the system may solve an inverse problem by iteratively modifying the parameters associated with the voxels in the forward model until a difference between the predicted component of the magnetization and the measured component of the magnetization is less than a predefined value.

Note that the parameters may include a density of a type of nuclei, a longitudinal relaxation time along a direction parallel to the external magnetic field and a transverse relaxation time along a direction perpendicular to the external magnetic field.

Moreover, the iterative modification may be based on a Jacobian matrix using Newton's method.

Furthermore, the iterative modifications may be constrained based on parameters determined using previous measurements of at least the component of the magnetization. Alternatively or additionally, initial values of the parameters may be within predefined parameter ranges for different types of tissue in the sample.

In some embodiments, the system may segment tissue types in the sample based on discontinuous changes in at least some of the parameters along a direction between the voxels.

Moreover, the parameters may be determined without performing a Fourier transform on the measured component of the magnetization.

Furthermore, the calculation of the component of the magnetization and the iterative modifications may be performed concurrently with the measurement of the component of the magnetization.

Additionally, the system may: modify at least one of the external magnetic field and the RF pulse sequence; apply at least the one of the modified external magnetic field and the RF pulse sequence to the sample before the sample has completely relaxed or without resetting a state of the sample; measure at least a second instance of the component of the magnetization; calculate at least a second instance of the predicted component of the magnetization for the voxels associated with the sample based on the measured second instance of the component of the magnetization, the forward model, the modified external magnetic field or the modified RF pulse sequence; and solve the inverse problem by iteratively modifying the parameters associated with the voxels in the forward model until a difference between the second instance of the predicted component of the magnetization and the second instance of the measured component of the magnetization is less than the predefined value. In some embodiments, the system may determine a dynamic state of the sample based on the forward model, the external magnetic field and the RF pulse sequence, where the dynamic state when at least one of the modified external magnetic field and the modified RF pulse sequence is applied to the sample may be used as an initial condition when calculating the second instance of the predicted component of the magnetization.

Note that at least one of a magnitude and a direction of the external magnetic field may be changed as a function of time during the measurement.

Moreover, at least one of the modified external magnetic field and the modified RF pulse sequence may be selected to minimize the difference between the second instance of the predicted component of the magnetization and the second instance of the measured component of the magnetization.

Furthermore, the parameters may be determined sequentially based on time scales associated with the parameters, and a parameter that has a shortest time scale may be determined first.

Another embodiment provides a computer-readable storage medium for use with a system. This computer-readable storage medium includes a program module that, when executed by the system, causes the system to perform at least some of the aforementioned operations.

Another embodiment provides a method for determining parameters associated with a sample. This method includes at least some of the aforementioned operations performed by the system.

This Summary is provided for purposes of illustrating some exemplary embodiments, so as to provide a basic understanding of some aspects of the subject matter described herein. Accordingly, it will be appreciated that the above-described features are simply examples and should not be construed to narrow the scope or spirit of the subject matter described herein in any way. Other features, aspects, and advantages of the subject matter described herein will become apparent from the following Detailed Description, Figures, and Claims.

Figure 1:
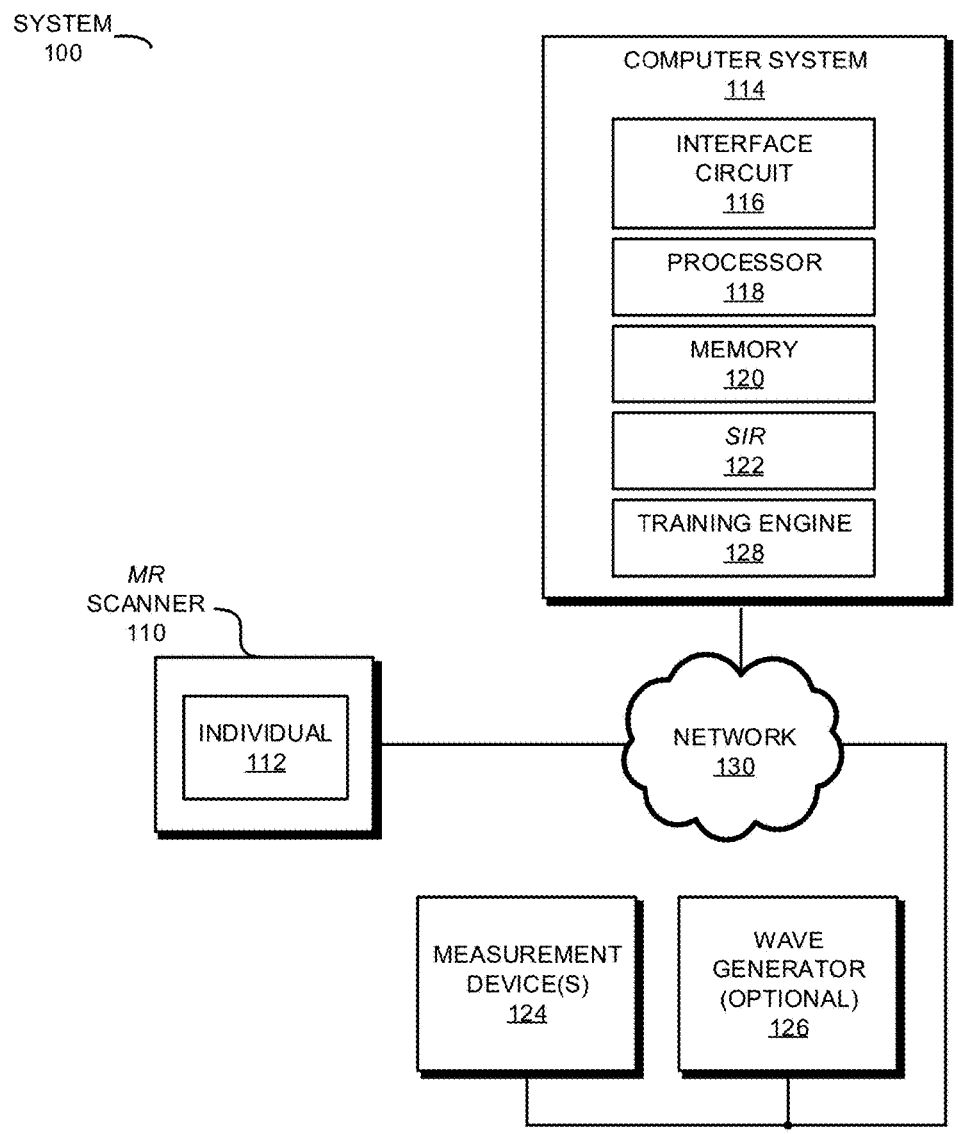
FIG. 1 is a block diagram illustrating a system with a magnetic-resonance (MR) scanner that performs an MR scan of a sample in accordance with an embodiment of the present disclosure.

Table 1 provides spin-lattice ($T_1$) and spin-spin ($T_2$) relaxation times in different types of tissue in accordance with an embodiment of the present disclosure.

Note that like reference numerals refer to corresponding parts throughout the drawings. Moreover, multiple instances of the same part are designated by a common prefix separated from an instance number by a dash.

DETAILED DESCRIPTION

During operation, a system may apply an external magnetic field and an RF pulse sequence to a sample. Then, the system may measure at least a component of a magnetization associated with the sample, such as MR signals of one or more types of nuclei in the sample. Moreover, the system may calculate at least a predicted component of the magnetization for voxels associated with the sample based on the measured component of the magnetization, a forward model, the external magnetic field and the RF pulse sequence. Next, the system may solve an inverse problem by iteratively modifying the parameters associated with the voxels in the forward model until a difference between the predicted component of the magnetization and the measured component of the magnetization is less than a predefined value. Note that the calculations may be performed concurrently with the measurements and may not involve performing a Fourier transform on the measured signal.

More generally, the system may apply a polarizing field and an excitation sequence to the sample, and may measure a corresponding response or physical phenomenon of the sample. Then, the system may iteratively converge the measurements with a forward model that predicts the physical phenomenon based on the parameters.

By facilitating determination of the parameters in voxels in the sample (which is sometimes referred to as 'tensor field mapping,' because the parameters in the voxels can be represented by a hybrid tensor as opposed to a true tensor for a vector field), this characterization technique may reduce the scan or measurement time. Therefore, the characterization technique may significantly reduce the cost of characterizing the sample by increasing throughput. Moreover, in embodiments where the sample is a patient, the reduced scan time may improve the user experience, such as by reducing the amount of time people spend in the confining environment of a magnet bore in an MR scanner. In addition, the one or more parameters and the forward model may facilitate quantitative analysis of the measurements and, thus, may improve the accuracy of the scans, thereby reducing errors, and improving the health and well-being of people.

In general, the characterization technique may use a wide variety of measurement techniques, including: an MR technique, x-ray imaging, x-ray diffraction, computed tomography, positron emission spectroscopy, neutron diffraction, electron microscopy, ultrasound imaging, electron spin resonance, optical/infrared spectroscopy (e.g., to determine a complex index of refraction at one or more wavelengths), electrical impedance at DC and/or an AC frequency, proton beam, photoacoustic, and/or another non-invasive measurement technique. In the discussion that follows, an MR technique is used as an illustration. For example, the MR technique may include: MRI, MR spectroscopy (MRS), magnetic resonance spectral imaging (MRSI), MR elastography (MRE), MR thermometry (MRT), magnetic-field relaxometry, diffusion-tensor imaging and/or another MR technique (such as functional MRI, metabolic imaging, molecular imaging, blood-flow imaging, etc.).

In particular, 'MRI' should be understood to include generating images (such as 2D slices) or maps of internal structure in a sample (such as anatomical structure in a biological sample, e.g., a tissue sample or a patient) based on the dynamic response of a type of nuclear spin (such protons or the isotope $^1$H) in the presence of a magnetic field, such as a non-uniform or spatially varying external magnetic field (e.g., an external magnetic field with a well-defined spatial gradient). Moreover, MRS should be understood to include determining chemical composition or morphology of a sample (such as a biological sample) based on the dynamic response of multiple types of nuclear spins (other than or in addition to $^1$H) in the presence of a magnetic field, such as a uniform external magnetic field.

Furthermore, 'MRSI' should be understood to include generating images or maps of internal structure and/or chemical composition or morphology in a sample using MRS in the presence of a magnetic field, such as a non-uniform or spatially varying external magnetic field. For example, in MRSI the measured dynamic response of other nuclei in addition to $^1$H are often used to generate images of the chemical composition or the morphology of different types of tissue and the internal anatomy of a patient.

Additionally, 'magnetic-field relaxometry' (such as $B_0$ relaxometry with the addition of a magnetic-field sweep) may involve acquiring MR images at different magnetic-field strengths. These measurements may be performed on the fly or dynamically (as opposed to performing measurements at a particular magnetic-field strength and subsequently cycling back to a nominal magnetic-field strength during readout, i.e., a quasi-static magnetic-field strength). For example, the measurements may be performed using un-tuned RF coils or a magnetometer so that measurements at the different magnetic-field strengths can be performed in significantly less time.

Moreover, in the discussion that follows 'MRE' should be understood to include measuring the stiffness of a sample using MRI by sending mechanical waves (such as sheer waves) through a sample, acquiring images of the propagation of the shear waves, and processing the images of the shear waves to produce a quantitative mapping of the sample stiffness (which are sometimes referred to as 'elastograms') and/or mechanical properties (such as rigidity, density, tensile strength, etc.).

Furthermore, 'MRT' should be understood to include measuring maps of temperature change in a sample using MRI.

As described further below, the characterization technique may exclude the use of a Fourier transform. Therefore, the characterization technique may be different from MR fingerprinting (MRF), which can provide quantitative maps of parameters associated with a sample in k-space based on, e.g., a pseudorandom pulse sequence. Instead, the characterization technique may analytically solve a system of equations to determine parameters in an MR model that describes a sample (as opposed to performing pattern matching in k-space).

In contrast, the tensor field maps determined in the characterization technique can be used in conjunction with the forward model (which describe or specify the relationships between state of a sample, excitation and response of the sample) to quantitatively predict the dynamic MR response of the voxels in the sample to an arbitrary external magnetic field, an arbitrary gradient and/or an arbitrary RF pulse sequence. Therefore, the tensor field maps may be independent of the particular MR scanner that was used to perform the measurements.

Note that the sample may include an organic material or an inorganic material. For example, the sample may include: an inanimate (i.e., non-biological) sample, a biological lifeform (such as a person or an animal, i.e., an in-vivo sample), or a tissue sample from an animal or a person (i.e., a portion of the animal or the person). In some embodiments, the tissue sample was previously removed from the animal or the person. Therefore, the tissue sample may be a pathology sample (such as a biopsy sample), which may be formalin fixed-paraffin embedded. In the discussion that follows, the sample is a person or an individual, which is used as an illustrative example.

We now describe embodiments of a system. While the pace of technical innovation in computing and MR software and hardware is increasing, today MR scans are still performed and interpreted in an 'analog' paradigm. In particular, MR scans are performed with at best limited context or knowledge about an individual and their pathologies, and typically are based on a limited set of programs that are input by a human operator or technician. Similarly, the resulting MR images are usually read by radiologists based on visual interpretation with at best limited comparisons with prior MR images. The disclosed system and characterization technique leverages computing power to significantly decrease the scan time of MR scans, and to facilitate a digital revolution in MR technology and radiology, with a commensurate impact of accuracy, patient outcomes and overall cost.

The disclosed system and characterization technique leverages predictive models of the sample to facilitate rapid determination of one or more physical parameters in voxels in the sample. These parameters may include: the spin-lattice relaxation time $T_1$ (which is the time constant associated with the loss of signal intensity as components of the nuclear-spin magnetization vector relax to be parallel with the direction of an external magnetic field), the spin-spin relaxation time $T_2$ (which is the time constant associated with broadening of the signal during relaxation of components of the nuclear-spin magnetization vector perpendicular to the direction of the external magnetic field), proton density (and, more generally, the densities of one or more type of nuclei) and/or diffusion (such as components in a diffusion tensor). The determination of the model parameters may be performed concurrently with MR measurements, thereby allowing the iterative process of comparison and refinement to converge rapidly (e.g., on time scales smaller than $T_1$ or $T_2$ in an arbitrary type of tissue.) Moreover, the predictive forward model may be used to simulate MR signals from the sample when subjected to an arbitrary external magnetic field (including an arbitrary direction, magnitude and/or gradient) and/or an arbitrary pulse sequence. Therefore, the model and the determined parameters may be used to facilitate fast and more accurate measurements, such as: soft-tissue measurements, morphological studies, chemical-shift measurements, magnetization-transfer measurements, MRS, measurements of one or more types of nuclei, Overhauser measurements, and/or functional imaging.

Furthermore, in some embodiments the characterization technique uses so-called 'breadth-first indexing' as a form of compressed sensing. In particular, the system may spend more time scanning and modeling interesting or dynamic parts of an individual, and may avoid spending time on parts that are not changing rapidly. Note that 'interesting' regions may be determined based on information gathered in real-time and/or based on historical information about the individual being scanned or other individuals. The breadth-first indexing may employ inference or inductive techniques, such as oversampling and/or changing the voxel size in different regions in the body based on an estimated abundance of various chemical species or types of nuclei (which may be determined using chemical shifts or MRS). The scan plan in such breath-first indexing may be dynamically updated or modified if a potential anomaly is detected.

In the discussion that follows, a scan plan can include a scan of some or all of an individual's body, as well as a reason or a goal of the scan. For example, a scan plan may indicate different organs, bones, joints, blood vessels, tendons, tissues, tumors, or other areas of interest in an individual's body. The scan plan may specify, directly or indirectly, scanning instructions for an MR scanner that performs the scan. In some embodiments, the scan plan includes or specifies one or more MR techniques and/or one or more pulse sequences. Alternatively, the one or more MR techniques and/or the one or more pulse sequences may be included or specified in the scanning instructions. As described further below, the scanning instructions may include registration of an individual, so that quantitative comparisons can be made with previous MR scans on the same or another occasion. Thus, at runtime, the areas of interest in the scan may be mapped to 3D spatial coordinates based on a registration scan.

The scan plan, as well as the related scanning instructions (such as the voxel size, one or more spectra, one or more types of nuclei, pulse sequences, etc.), may be determined based on a wide variety of information and data, including: instructions from a physician, medical lab test results (e.g., a blood test, urine-sample testing, biopsies, etc.), an individual's medical history, the individual's family history, comparisons against previous MR scan records, analysis of MR signals acquired in a current scan, and/or other inputs. In some embodiments, the MR scan plan is determined based on risk inputs, such as inputs used to determine the individual's risk to pathologies that are included in a pathology knowledge base. The risk inputs can include: age, gender, current height, historical heights, current weight, historical weights, current blood pressure, historical blood pressures, medical history, family medical history, genetic or genomic information for the individual (such as sequencing, next-generation sequencing, RNA sequencing, epigenetic information, etc.), genetic or genomic information of the individual's family, current symptoms, previously acquired MR signals or images, quantitative tensor field maps, medical images, previous blood or lab tests, previous microbiome analysis, previous urine analysis, previous stool analysis, the individual's temperature, thermal-imaging readings, optical images (e.g., of the individual's eyes, ears, throat, nose, etc.), body impedance, a hydration level of the individual, a diet of the individual, previous surgeries, previous hospital stays, and/or additional information (such as biopsies, treatments, medications currently being taken, allergies, etc.).

Based on scanning instructions that are determined from an initial scan plan (such as using predefined or predetermined pulse sequences for particular at-risk pathologies), the system may measure and store for future use MR signals, such as MR signals associated with a 3D slice through the individual. In general, the MR measurements or scans may acquire 2D or 3D information. In some embodiments, the MR measurements include animations of the individual's body or a portion of their body over time, e.g., over weeks, months, years, or shorter timescales, such as during a surgical procedure.

As noted previously, during the measurements the system may perform a registration scan, which may include a fast morphological scan to register, segment, and model a body in 3D space, and to help calibrate noise-cancellation techniques, such as those based on motion of the individual. For example, the system may include optical and thermal sensors, as well as pulse monitoring, to measure motion of the individual associated with their heartbeat and respiration. Note that a scan can be interrupted to re-run a registration scan to make sure an individual has not shifted or moved. Alternatively or additionally, the measured MR signals during a scan may be used to track and correct the motion of the individual. This correction may be performed during a scan (e.g., by aggregating MR signals associated with a voxel at a particular 3D position) and/or subsequently when the MR signals are analyzed.

In some embodiments (such as during MRI), the system may determine segments of the individual's body. This segmentation may be based, at least in part, on a comparison with segments determined in one or more previous scans. Alternatively or additionally, the measurements may include a segmentation scan that provides sufficient information for a segmentation technique to correctly segment at least a portion of the body of the individual being imaged. In some embodiments, segmentation between different types of tissue is based on discontinuous changes in at least some of the determined model parameters along a direction between the voxels.

Then, the system may analyze the MR signals. This analysis may involve resampling and/or interpolating measured or estimated MR signals from the 3D positions of the voxels in the previous scan(s) to the 3D positions of the voxels in the current scan. Alternatively or additionally, the analysis may involve alignment of voxels based on registration of the 3D positions of the voxels in the individual in the current scan with those in one or more previous scan(s) for the same and/or other individuals. For example, the aligning may involve performing point-set registration, such as with reference markers at known spatial locations or with the voxels in previous MR scan. The registration may use a global or a local positioning system to determine changes in the position of the individual relative to an MR scanner.

Moreover, a previous MR model may be used to generate estimated MR signals for sets of voxels. The estimated MR signals in a given set of voxels may be averaged, and the resulting average MR signals in the sets of voxels may be compared to MR signals measured during a current scan to determine a static (or a dynamic) offset vector. For example, the positions of the average MR signals in the set of voxels (such as average MR signals in 3, 6, 12 or 24 regions or portions of an individual) may be correlated (in 2D or 3D) with the MR signals in the set of voxels in the current scan. This offset vector may be used to align the MR signals and the estimated MR signals during subsequent comparisons or analysis. Alternatively, the comparisons may be made on a voxel-by-voxel basis without averaging. Thus, the MR signals for a voxel in the individual may be compared to corresponding MR signals for the voxel measured on a prior occasion by performing a look-up in a table. In some embodiments, the registration or the offset vector of an individual is computed based on variation in the Larmor frequency and the predetermined spatial magnetic-field inhomogeneity or variation in the magnetic field of an MR scanner.

Furthermore, the registration technique may involve detecting the edges in node/voxel configurations. Because of the variability of anatomy across different individuals, transforming small variations of data into more generalized coordinates may be used to enable analysis and to generalize the results to a population. In general, the transforms may be one-to-one and invertible, and may preserve properties useful for identification and diagnostics, such as: curves, surfaces, textures and/or other features. For example, the features may be constrained to diffeomorphic transformations (such as smooth invertible transformations having a smooth inverse) or deformation metric mappings computed via geodesic flows of diffeomorphisms. In some embodiments, a diffeomorphic transformation between surfaces is used to compute changes on multi-dimensional structures (e.g., as a function of time).

Additionally, linear combinations of diffeomorphic transformations computed based on sets of matches between MR signals and simulated or estimated MR signals can provide spatial offset corrections based on a piori estimated information (such as motion, deformation, variations in anatomy, magnetic field, environmental conditions, etc.). These spatial offset corrections may be used as a weighted component in a supervised-learning registration engine. For example, a set of diffeomorphic velocity fields tracking a set of points across a set of phases of distortion (caused by movement of the lungs during regular breathing, the heart during heartbeat motion or a muscle during contraction or expansion) can be applied to a region of the body corresponding to the sets of points in the region (e.g., a set of voxels in or around the heart or lungs).

Next, during the analysis, the system may compare current MR signals with estimated MR signals based on the forward model and current values of the parameters. Note that the comparison may be performed on a voxel-by-voxel basis. Then, the system may modify or update the model parameters based on the comparison so that a difference between the measurements and the simulations converges (i.e., a magnitude of the difference decreases below a threshold or a predefined value, such as a 0.1, 1 or 5% error).

In some embodiments, the system compares current measurements of MR signals with previous MR signals. Note that the comparison may be facilitated using a look-up table. For example, the system may compare measured MR signals from a voxel with a value in a look-up table that is based on simulated MR signals associated with a previous scan. In this way, the system can compare metabolic chemical signatures between adjacent voxels in an MRS scan to detect a potential anomaly or can perform comparisons to MR signals that are a composite of two or more individual's bodies.

Note that the initial scan plan may include an MR scan using a low magnetic field or no magnetic field MR scan (e.g., RF only) or a measurement other than MR, such as synthetic aperture radar (SAR), to scan for ferromagnetic or paramagnetic materials (e.g., metal plates, pins, shrapnel, other metallic or foreign bodies) in an individual's body. Alternatively or additionally, the initial scan may use electron-spin resonance. In some embodiments, the presence of a ferromagnetic or paramagnetic material in the sample may be identified based on the known $T_1$, $T_2$ and/or the permeability of a ferromagnetic or a paramagnetic material. Furthermore, the presence of a ferromagnetic or paramagnetic material may be determined based on a systematic error in the parameters in the forward model. For example, the determined type of tissue may be incorrect or may be anatomically incorrect (such as the wrong shape) because of errors induced by the presence of a ferromagnetic or paramagnetic material. In addition to identifying a ferromagnetic or paramagnetic material, the MR model based on the MR measurements may be used to remove or correct the corresponding artifacts in the MR images. Consequently, the characterization technique may allow patients with metal in or on their bodies to be scanned. This may allow patients to leave their clothing on during an MR scan.

The initial scan for ferromagnetic or paramagnetic materials can improve safety in the system when MR scanning is used. This may be useful in case an individual's medical record does not include information about foreign objects, the foreign objects are new or unknown (e.g., shrapnel fragments remaining in a wound or in excised tissue), or in the event of an error. In particular, this 'safety scan' can prevent damage or injury to the individual, and can protect the system from damage. In addition, the size of any ferromagnetic or paramagnetic material can be estimated during the initial scan, and a safe magnetic-field strength for use during the MR scan can be estimated. Conversely, if the individual does not contain any ferromagnetic of paramagnetic materials, one or more higher magnetic-field strengths can be used during one or more subsequent MR scans.

Based on the comparison, the system may classify a voxel as: low risk, high risk or unknown risk. For example, a voxel may be classified as indicative of: early-stage cancer, late-stage cancer, or an unknown-stage cancer. In particular, the system may perform automatic quantitative processing of MR signals from the individual voxels based on a library of baseline tissue characterizations or templates. In this way, quantitative MR measurements based on a scan plan can be used to quantify the health of: particular organs (such as scanning the liver of the individual for cancer), performing assays of blood, detecting known-good and known-bad quantitative signatures of specific tissues (e.g., skin, heart, liver, muscle, bone, etc.), performing post-biopsy analysis, another type of evaluation, etc.

The resulting classifications (including unknown classifications) may be provided to a radiologist (such as via a graphical user interface that is displayed on a display). In particular, the radiologist may provide a classification, identification feedback or verification feedback. The information from the radiologist may be used to update the analysis (such as one or more supervised-learning models, the look-up table and/or the associated classifications).

When a potential anomaly is detected, the system may dynamically revise or modify the scan plan (and, thus, the scanning instructions) based on the detected potential anomaly, as well as possibly one or more of the factors mentioned previously that were used to determine the initial scan plan. For example, the system may change the voxel size, a type of nuclei, the MR technique (such as switching from MRI to MRS), etc. based on the detected potential anomaly. The modified scan plan may include a region that includes or that is around the detected potential anomaly. Thus, the size of the region may be determined based on a size of the detected potential anomaly. Alternatively or additionally, the region in the modified scan plan may be determined based on a location or segment in the individual's body where the potential anomaly is located.

Next, the system may perform additional MR measurements, which are then analyzed and stored for future use. Note that this additional scan may occur after completion of the first or initial scan of the individual. For example, the modified scanning instructions may be queued for execution after the first scan is completed. Alternatively, when the potential anomaly is detected, the first scan may be stopped (i.e., when it is only partially completed) and the partial MR signals may be stored and/or provided to the system. In some embodiments, the system stops the first scan by providing an interrupt to the MR scanner. Then, after the second or the additional scan is completed, the MR scanner may complete the first scan, and the remainder of the MR signals may be stored and/or provided to the system. In order to complete the interrupted or stopped first scan, the MR scanner may save or store information that specifies the current position when it stopped, as well as the scanning context (such as the MR measurement being performed). This positioning and scanning context information may be used by the MR scanner when the first scan is resumed.

After completing the first and/or the second MR scan (or any additional related scans), as well as the associated analysis, the system may determine a recommended time for a follow up scan of the individual based on any detected anomalies (and, more generally, the results of the current MR scan(s) and/or one or more previous MR scans) and/or any of the aforementioned factors that were used to determine the scan plan(s). Moreover, the system may determine a future scan plan for the individual or another individual based on the results of the current MR scan(s) and/or comparisons of the current MR scan(s) with one or more previous MR scans. This capability may allow the system to facilitate monitoring of one or more individuals over time or longitudinally. Furthermore, this approach may allow the feedback from even a single radiologist to impact the future scan plans of one or more individuals.

When determining a scan plan and/or analyzing measured or acquired MR signals the system may access a large data structure or knowledge base of tensor field maps of parameters from multiple individuals (which is sometimes referred to as a 'biovault'), which may facilitate quantitative comparisons and analysis of MR scans. The biovault may include: the tensor field maps, additional information and/or identifiers of individuals in the data structure (such as unique identifiers for the individuals). Furthermore, the additional information may include diagnostic information or metadata associated with previous measurements on the individuals or tissue samples associated with the individuals, including: weight, size/dimensions, one or more optical images, one or more infrared images, impedance/hydration measurements, data associated with one or more additional MR techniques, demographic information, family histories and/or medical histories. Note that the biovault may include information for symptomatic and/or asymptomatic individuals. (Therefore, the individuals may not solely be healthy or unhealthy. For example, a particular tensor field map may be healthy in certain medical contexts, such as for a particular person, but may be unhealthy in another medical context.) Thus, the biovault can be used to characterize healthy tissue, as well as disease or pathology.

FIG. 1 presents a block diagram illustrating an example of a system 100. This system includes: an MR scanner 110 and computer system 114. As described further below with reference to FIG. 14, computer system 114 may include: a networking subsystem (such as an interface circuit 116), a processing subsystem (such as a processor 118), and a storage subsystem (such as memory 120). During operation of system 100, a technician or an MR operator can scan or read in information about an individual 112 using sample-information reader (SIR) 122 to extract information (such as an identifier, which may be a unique identifier) from a label associated with individual 112 (who is used as an illustrative example of a sample in the discussion that follows). For example, sample-information reader 122 may acquire an image of the label, and the information may be extracted using an optical character recognition technique. More generally, note that sample-information reader 122 may include: a laser imaging system, an optical imaging system (such as a CCD or CMOS imaging sensor, or an optical camera), an infrared imaging system, a barcode scanner, an RFID reader, a QR code reader, a near-field communication system, and/or a wireless communication system.

Alternatively, the technician or the MR operator may input information about individual 112 via a user interface associated with computer system 114. Note that the extracted and/or input information may include: the unique identifier of individual 112 (such as a subject or patient identifier), an age, a gender, an organ or a tissue type being studied, a date of the MR scan, a doctor or practitioner treating or associated with individual 112, the time and place of the MR scan, a diagnosis (if available), etc.

Then, the technician or the MR operator can place individual 112 in MR scanner 110, and can initiate the MR scans (which may involve MRI, MRT, MRE, MRS, magnetic-field relaxometry, etc.) and/or other measurements, e.g., by pushing a physical button or activating a virtual icon in a user interface associated with computer system 114. Note that the same individuals (and, more generally, the same tissue sample or material) can have different MR signals (such as different signal intensities and/or frequencies) in different datasets that are measured in the same MR scanner or in different MR scanners. In general, such measurement-to-measurement variation depends on many factors, including: the particular instance of MR scanner 110, a type or model of MR scanner 110, a set-up of MR scanner 110, the scanning instructions (such as the magnetic-field strengths, magnetic gradients, voxel sizes, the pulse sequences that are applied to individual 112, the MR techniques, the regions of interest in individual 112, one or more voxel sizes and/or the types of nuclei or molecules), a detector in MR scanner 110, and/or one or more signal-processing techniques. For example, the one or more signal-processing techniques may include: gradient-echo imaging, multi-slice imaging, volume imaging, oblique imaging, spin-echo imaging, inversion recovery imaging, chemical contrast agent imaging, fat suppression imaging using spin-echo imaging with saturation pulses before taking regular images, etc.

These challenges are addressed in system 100 in the characterization technique by performing MR scans and comparing the associated MR signals with simulated or estimated MR signals based on a tensor field map of parameters and a forward model. The stored information may specify MR scanner 110, magnetic-field inhomogeneity, the scanning instructions, etc., so that the parameter results from previous measurements of MR signals can be used to generate estimated MR signals that are compared to current measurements of MR signals. In some embodiments, the stored information includes one or more 'invariant MR signatures' (which are sometimes referred to as 'magnetic-field-invariant MR signatures'), where an invariant MR signature is independent of magnetic field, the scanning instructions (e.g., magnetic-field strengths and/or pulse sequences) and the MR scanner used, and that specifies the dynamic MR response of voxels at 3D positions in individual 112 to an arbitrary magnetic field based on previous measurements of MR signals. Note that an invariant MR signature may be determined by iteratively converging MR signals of one or more types of nuclei with estimated or estimated MR signals that are generated using a forward model (which is sometimes referred to as an 'MR model') and scanning instructions, including measurements or scans performed at different magnetic fields.

The one or more invariant MR signatures may include the information about individual 112, such as high-quality quantitative maps of $T_1$, $T_2$, nuclei density, diffusion, velocity/flow, temperature, off-resonance frequency, and magnetic susceptibility. Moreover, the one or more invariant MR signatures may be corrected for measurement-to-measurement variation, including variation that occurs from one MR scanner to another. Alternatively, the one or more invariant MR signatures may include information that corrects for measurement-to-measurement variation and/or that allows a version of an MR image, an MR spectra, etc. to be generated for particular measurement conditions, such as: a particular MR scanner, a particular model of the MR scanner, scanning instructions, a particular detector, etc. Thus, in conjunction with characteristics of a particular MR scanner (such as the model of this particular MR scanner, the scanning instructions, the detector, noise characteristics of the particular MR scanner, and the magnetic-field inhomogeneity in the particular MR scanner), the one or more invariant MR signatures may be used to generate or calculate a version of an MR image, an MR spectra, etc. as if it were measured by the particular MR scanner. Note that the noise characteristics of the particular MR scanner may depend on the pulse sequence used.

In some embodiments, an invariant MR signature includes parameters in an MR model' of voxels in at least individual 112. Because each voxel in the MR model may include multi-dimensional data on the volumetric density of certain chemical signatures and atomic nuclei, the invariant MR signature of individual 112 may be based on an awareness of one or more regions of individual 112. For example, the voxel size in the MR model may depend on an anatomical location in individual 112.

Moreover, system 100 may use the information in the biovault, the MR signals acquired in an initial scan of individual 112 and/or one or more detected potential anomalies to further optimize the scan plan and, thus, scanning instructions (and, more generally, the conditions during the MR measurements) when collecting additional MR signals from individual 112. For example, the extracted and/or input information about individual 112, as well as additional stored information in memory 120 that is accessed based on the unique identifier (such as a medical record or medical history that is linked or queried based on the unique identifier), may be used by computer system 114 to update the scanning instructions (such as different pulse sequences and/or different magnetic-field strengths, e.g., a range of magnetic-field strengths, including 0 T, 6.5 mT, 1.5 T, 3 T, 4.7 T, 9.4 T, and/or 15 T, the MR techniques, the regions of interest in individual 112, the voxel sizes and/or the types of nuclei), the other measurements to perform and, more generally, a scan or analysis plan. In general, the scanning instructions may specify more than a single value of the magnetic-field strength. For example, the scanning instructions may provide or specify a function that describes how the magnetic field will change over time and in space, or multiple functions that specify a 'surface' that can be used to determine the invariant MR signature of individual 112. As described further below with reference to FIG. 2, in some embodiments the magnetic field is physically and/or virtually manipulated to achieve the specified surface. In particular, the magnetic field may be rotated as a function of time, or in embodiments with physically separate ring magnets that generate the magnetic field, the magnetic field may be changed by: changing the physical distance between the ring magnets, changing the orientation of one ring magnet with respect to the other ring magnet, moving a ring magnet along the z axis, etc. Moreover, the changes in the external magnetic field magnitude and/or direction, which is used to polarize the nuclei in individual 112, may occur while the MR signals are being measured using MR scanner 110.

Moreover, as described further below, note that the other measurements may include: impedance measurements, optical imaging, scanning of dimensions of individual 112, weighing individual 112 and/or other tests that may be included in the characterization technique. For example, a gel-covered table in MR scanner 110 can be used to measure an impedance of individual 112 and/or a weight of individual 112. In some embodiments the other measurements probe individual 112 non-destructively (e.g., using electromagnetic or mechanical waves). However, in other embodiments the characterization technique includes integrated therapeutics, such as: proton beam therapy, radiation therapy, magnetically guided nano particles, etc.

In addition, predetermined characterization of MR scanner 110 may be used to determine the scanning instructions. Alternatively, if MR scanner 110 has not already been characterized, system 100 may characterize and store characteristics of MR scanner 110 prior to calculating simulated or estimated MR signals or determining the invariant MR signature, so that the characteristic of MR scanner 110 can be used during the characterization technique, such as to determine the scanning instructions. For example, during operation, computer system 114 may characterize MR scanner 110 based on scans of a phantom.

Note that the predetermined characterization of MR scanner 110 may include a mapping or determination of the inhomogeneity of the magnetic field of MR scanner 110 (because the magnetic-field inhomogeneity may depend on the magnetic-field strength, measurements may be performed at different magnetic-field strengths). The predetermined characterization may also include environmental, geographical and/or other parameters. For example, RF pulses generated by a pulse generator in system 100 may vary from one MR scanner to another, and may vary as a function of time because the performance of components may depend on parameters such as: the load, the temperature, the MR coil configuration, amplifiers, humidity, magnetic storms and/or geolocation. Consequently, in addition to MR signals, the RF pulses (and/or the inhomogeneity in the RF pulses) may be measured, e.g., using a signal splitter between an RF pulse generator and an RF (transmission) coil in MR scanner 110. In some embodiments, the magnetic field produced by the RF coil is measured using a test coil. Note that, because a specific pulse sequence may correspond to a specific voxel size, different pulse sequences corresponding to different voxel sizes may be used when characterizing MR scanner 110 and/or when determining the scanning instructions.

As described further below with reference to FIGS. 3-5 and 12-14, the measurements and recorded signals associated with MR scanner 110 may be used to generate an MR model of MR scanner 110 that accurately predicts MR signal evolution or response for a phantom having known properties over a range of parameters ($T_1$, $T_2$, proton density, off-resonances, environment, location, temperature, pulse sequences, etc.) using the Bloch equations, full Liouvillian computations or another simulation technique. In this way, the MR model may characterize MR scanner 110.

The predetermined characterization of MR scanner 110 can be used to transform a generic invariant MR signature into a machine-specific invariant MR signature associated with a particular MR scanner, such as MR scanner 110. In conjunction with the magnetic field and the pulse sequence, the machine-specific invariant MR signature may be used to predict or calculate simulated MR signals during an arbitrary MR scan in the particular MR scanner. Similarly, predetermined characterizations of different MR scanners can be used to convert from one machine-specific invariant MR signature to another.

In some embodiments, the predetermined characterization of MR scanner 110 includes measured ambient noise from electronics in or associated with MR scanner 110. During subsequent MR scans or simulations, digital filters may use the measured noise (or statistical parameters that describe the measured noise) to improve the quality of measured MR signals and/or calculated MR models. Moreover, the various measurements may be synchronized with an external reference clock or to a biological time period (such as a respiration period, a heart-beat period, a fundamental period for body motion, etc.) to enable subsequent synchronous averaging or additional signal processing.

Moreover, during the characterization technique, computer system 114 may repeatedly perform MR scans of different materials (such as different types nuclei) in individual 112 using MR scanner 110 based on instances of the scanning instructions that are received via network 130. Note that the MR scans of the different materials may be pseudorandomly acquired. For example, an MR scan of a particular material in individual 112 may be selected based on a random or a pseudorandom number provided by a circuit or software-implemented random or a pseudorandom number generator in computer system 114. In some embodiments, the MR scan of a particular material in individual 112 may be selected based on a Bayesian statistical approach that guides a search for potential anomalies.

Alternatively, the different materials in individual 112 may be systematically scanned for each instance of the scanning instructions.

Furthermore, the MR signals acquired or captured during a particular MR scan may be used to modify or adapt an MR model of voxels in individual 112. For example, as noted previously and as described further below with reference to FIGS. 3-5 and 12-14, computer system 114 may determine the MR model (such as parameters in the MR model) based on differences (or a difference vector) between MR signals associated with the voxels in one or more MR scans and simulated or estimated MR signals (which may be generated using the MR model, an instance of the scanning instructions and optionally the characteristics of MR scanner 110). Note that the difference vector may be weighted based on a priori computed information to reduce the error, e.g., to obtain the smallest difference vector or the smallest difference vector measured across a set of weighted simulated MR signals (which may be precomputed). In some embodiments, the difference vector is determined using a dot product or inner product of one or more MR signals and simulated or estimated MR signals (which are each associated with or corrected to a common magnetic-field strength), cosine similarity between one or more MR signals and estimated MR signals, spectral analysis, and/or another comparison technique.

Then, based on the remaining differences (or the remaining difference vector) and/or one or more detected potential anomalies, the scanning instructions may be modified, i.e., a new instance of the scanning instructions (including one or more magnetic-field strengths and one or more pulse sequence(s) that will be applied to individual 112, the MR technique, the regions of interest in individual 112, the voxel sizes and/or the types of nuclei) may be determined. In some embodiments, the scanning instructions (such as the changes to the external magnetic field and/or the RF pulse sequence) are selected in order to minimize or reduce the remaining differences. In this way, the process of determining the MR model may converge rapidly or optimally.

These operations may be iteratively repeated until a convergence criterion is achieved. For example, the convergence criterion may include that the difference between the MR signals and the simulated MR signals is less than a predefined value (such as 0.1, 1, 3, 5 or 10%) and/or that the changes to the scanning instructions are less than the predefined value. Furthermore, the convergence criterion may include completion of the scan plan.

These capabilities of the system 100 may allow scans to be performed as needed, after a time interval or periodically on an individual, so that the biovault can amass information and knowledge about the individual's (as well as other individuals) body and health. This information and knowledge can be used tailor or target scan plans based on the individual's needs, such as based on changes over time in their body.

Figure 2:
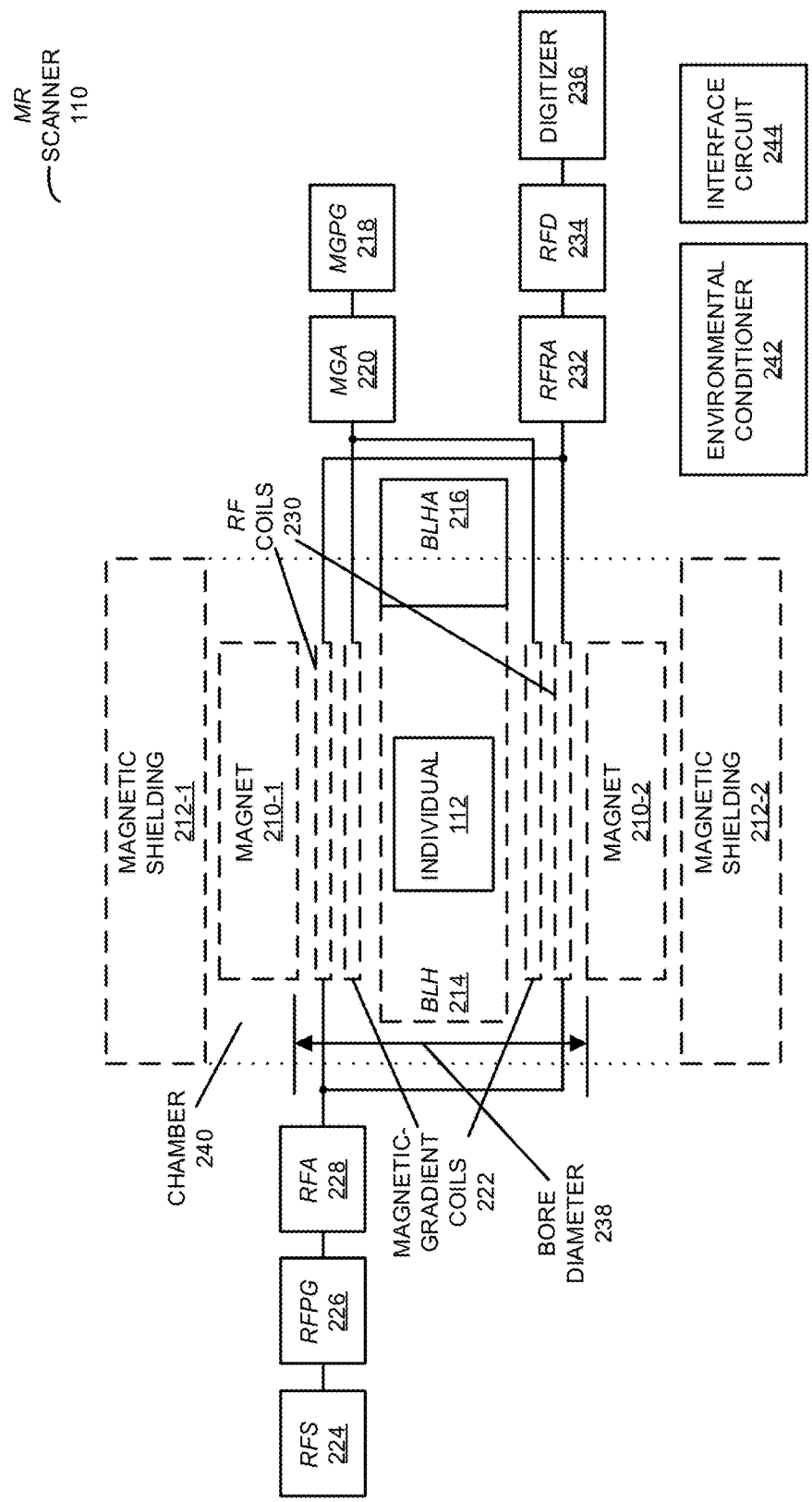
FIG. 2 is a block diagram of the MR scanner in the system of FIG. 1 in accordance with an embodiment of the present disclosure.

We now further describe operations in the characterization technique in more detail. FIG. 2 presents a block diagram of an example of MR scanner 110. This MR scanner may include a magnet 210, magnetic shielding 212, a biological lifeform holder (BLH) 214, a biological lifeform holder articulator (BLHA) 216, a magnetic-gradient pulse generator (MGPG) 218, a magnetic-gradient amplifier (MGA) 220, magnetic-gradient coils 222, an RE pulse generator (RFPG) 226, an RF source (RFS) 224, RF amplifier (RFA) 228, RF coils 230, an RF receive amplifier (RFRA) 232, an RF detector (RFD) 234, a digitizer 236 (such as an analog-to-digital converter), an environmental conditioner 242 and an interface circuit 244. (Note that mechanical and electrical connections to environmental conditioner 242 and interface circuit 244 are not shown in FIG. 2.) At least some of these components may be coupled, via interface circuit 244, network 130 (FIG. 1) and interface circuit 116 (FIG. 1), to computer system 114, which may control operation of MR scanner 110. The components in MR scanner 110 are described briefly below.

Note that MR scanner 110 may be a closed-bore or an open-bore system. In particular, magnet 210 (illustrated in a cross-sectional view in FIG. 2 by portions of magnet 210-1 and 210-2) may be closed bore or open bore. For example, a bore diameter 238 of magnet 210 may be between 1 and 10 cm or between 5 and 30 cm. An open-bore system may generate a magnetic field using two plates separated by a gap, and individual 112 may be exposed to (and nuclei in individual 112 may be polarized by) the magnetic field between the plates. Alternatively, a closed-bore system may have a toroidal shaped magnet 210, individual 112 may be moved through a hole in the center of the toroid (thus, using a strong field or high field to polarize nuclei in individual 112). Moreover, the orientation of magnet 210 may be horizontal (which is sometimes referred to as 'horizontal bore') so that individual 112 moves horizontally through the magnetic field, but can also be vertically oriented. In general, MR scanner 110 may scan individual 112 in various positions, including at different angles, orientations and perspectives (e.g., by adjusting biological lifeform holder articulator 216). (Thus, when MR scans are performed on individuals or animals, MR scanner 110 may allow measurements to be made while an individual is standing, sitting, laying down, suspended, positioned under a load (e.g., a position or posture required for a sports motion or a weightlifting technique), positioned on their side or even in motion, such as walking on a treadmill or jumping in the air.) Note that embodiments with a smaller bore diameter 238 may allow MR scanner 110 to be portable. While FIG. 2 illustrates MR scanner 110 with magnet 210, note that in some embodiments MR scanner 110 may exclude magnet 210. This may be facilitated by the characterization technique, which, as described further below, may allow the parameters in the MR model to be determined using very low and/or inhomogenous magnetic fields.

Depending on the MR technique, the magnetic-field strength $B_0$ of magnet 210 may be low field (e.g., an electromagnet having a peak magnetic-field strength that is less than 0.1 T, such as a magnetic-field strength as low as 0.001 T or even 0 T), a strong field (e.g., a ferro-magnet having a peak magnetic-field strength of around 0.5 T) or high field (e.g., a superconducting magnet having a peak magnetic-field strength greater than around 0.5 T). In general, a wide variety of magnets and magnetic configurations may be used. In embodiments with a superconductor, magnet 210 may be cooled using a cryogenic fluid, such as liquid helium or liquid helium in a surrounding dewar filled with liquid nitrogen or that is refrigerated. However, in other embodiments magnet 210 operates at or near room temperature. Furthermore, magnet 210 may be modular, such as a set of superconducting rings that each can have a peak magnetic-field strength of 0.5 T and that can be added, removed or moved to create different magnetic-field magnitudes and configurations.

Magnet 210 may produce magnetic fields that can be changed physically and/or virtually (via gradient fields and/or pulse sequences). This capability may allow slow rotation of the main external magnetic field, so that MRS can be performed at low magnetic-fields strengths. This additional degree of freedom may provide more ways to perturb the magnetic moments in individual 112 to obtain information that can reduce the complexity of the invariant MR signature and/or the MR model calculations. Note that moving or changing the orientation of magnet 210 may involve: moving pairs of ring magnets closer or further away on the z axis as part of a scan plan; rotating magnet 210 relative to the volume of space being indexed; changing the orientation/alignment of magnet 210 with respect to the z axis of the volume being indexed, etc. Moreover, 'physically' can mean physical movement of magnet 210, while 'virtually' may indicate that gradient fields and/or pulse sequences (such as a so-called 'spin-lock technique') are used to achieve the same result without physically changing the orientation of magnet 210. In general, these techniques may be used independently of each other or two or more of the techniques may be used in conjunction with each other.

Magnet 210 may also be used to (intentionally) dynamically vary the magnetic-field inhomogeneity. For example, by physically rotating a shim coil and/or by applying particular pulse sequences, the magnetic-field inhomogeneity may be modified. Moreover, by introducing specific kinds of magnetic-field inhomogeneity at different points in space, MR scanner 110 can differentiate certain kinds of tissue that are in close proximity.

Magnetic shielding 212 may include steel plates or metal sheets of silicon steel. This magnetic shielding may be placed all around a room, fully covering walls, floors and ceilings, in order to attenuate the magnetic-field strength outside the room to below 5 Gauss (or 0.5 mT). Moreover, special doors and doorframe seals may be used to further reduce the magnetic field that 'leaks' out of the room. Furthermore, magnet 210 may include shielding (such as a second set of superconducting windings with an opposite current flow than the main superconducting windings) in order to reduce the fringe magnetic field. For example, the magnetic-field strength may be 0.5 mT at a distance of four meters from magnet 210. This configuration may reduce the amount of magnetic shielding 212 or may eliminate the need for magnetic shielding 212 entirely.

In some embodiments, magnetic shielding 212 may provide a chamber 240 (defined by a surface of magnetic shielding 212), and this chamber may be optionally sealed so that at least a portion of individual 112 or a tissue sample being measured is at less than atmospheric pressure (i.e., a vacuum chamber) or may contain an inert gas (such as xenon) that can be pre-polarized to improve the MR imaging quality. (More generally, a solid, liquid or gas contrast agent may be used to improve the MR imaging quality.) In particular, environmental conditioner 242, such as a gas valve and a vacuum pump that are controlled by computer system 114, may be used to reduce the pressure in chamber 240. Alternatively, environmental conditioner 242 may include the gas valve and a gas tank that selectively allow (under control of computer system 114) the inert gas to flow into chamber 240. However, in other embodiments chamber 240 is defined by or provided by a surface of biological lifeform holder 214.

Note that magnetic-gradient pulse generator 218 may provide gradient pulses. These gradient pulses may be amplified by magnetic-gradient amplifier 220 to a level suitable for driving magnetic-gradient coils 222. Note that magnetic-gradient pulse generator 218 and magnetic-gradient amplifier 220 may be controlled by computer system 114 via an interface circuit 116 (FIG. 1), network 130 (FIG. 1) and interface circuit 244. For example, computer system 114 may specify the types and shapes of magnetic pulses provided by magnetic-gradient pulse generator 218, and may specify the amplification or gain of magnetic-gradient amplifier 220.

Moreover, magnetic-gradient coils 222 may produce the shape and amplitude of the gradient magnetic field along the x, y and z axes (in a right-handed Cartesian coordinate system). Magnetic-gradient coils 222 typically operate at room temperature and may produce spatial gradients in the magnetic field $B_0$. For example, in a horizontal bore system, a gradient in the magnetic field $B_0$ along the z-axis or direction (i.e., parallel to a symmetry axis of the bore of magnet 210) may be achieved using an anti-Helmholtz coil, with current in each coil adding to or subtracting from the magnetic field $B_0$ to achieve the gradient. Furthermore, gradients along the x and y-axes may be generated or created using a pair coils having a 'FIG. 8' shape (which create gradients along their respective axes).

In some embodiments, magnetic-gradient coils 222 have gradients of 100 mT/m and have fast switching times (or slew rates) of 150 T/m/s, which may enable a slice thickness of 0.7 mm and a voxel resolution of 0.1 mm in 3D imaging. However, by using high frequencies (such as frequencies above approximately 100 kHz), slew rates higher than the current U.S. slew-rate limit of 200 T/m/s may be used. If magnet 210 produces a larger magnetic-field strength (such as 7 T), an isometric voxel resolution of 60 μm may be achieved.

Furthermore, RF pulse generator 226 may generate RF pulses based on carrier waves output by RF source 224 (such as sinewaves or RF pulses having desired fundamental frequencies based on a target type of nuclei and magnetic-field strength $B_0$), and RF amplifier 228 may increase the power of the RF pulses to be strong enough to drive RF coils 230 (e.g., increasing the power from milliWatts to kiloWatts). RF coils 230 may create a magnetic field $B_1$ that rotates the net magnetization of type of nuclei in individual 112 based on the pulse sequence. Note that RF pulse generator 226, RF source 224 and RF amplifier 228 may be controlled by computer system 114 via interface circuit 116 (FIG. 1), network 130 (FIG. 1) and interface circuit 244. For example, computer system 114 may specify the type or shape of pulse(s) output by RF pulse generator 226, the frequencies in the carrier frequencies or pulses provided by RF source 224 and/or the amplification or gain of RF amplifier 228.

In some embodiments, RF pulse generator 226 shapes the carrier waves or RF pulses into apodized sine pulses, which may smooth discontinuities that can adversely affect the measurements and/or subsequent signal processing. Apodized sine pulses may excite the spin states of the nuclei, and these excited spin states may decay and release a pulse of RF energy that is captured during acquisition. In general, a wide variety of pulse sequences may be used during the characterization technique. For example, the pulse sequence may include or may be associated with MR techniques such as: turbo field echo (TFE), fast field echo (FFE), susceptibility weighted imaging (SWE), short tau inversion recovery (STIR) or short $T_1$ inversion recovery (a type of suppression technique for fatty tissue with an inversion time TI equal to $T_1 \cdot \ln(2)$ so that the MR signal of fat is zero), turbo spin echo (TSE), fast low angle shot or FLASH (a type of spin-echo sequence in which larger tip angles provide more $T_1$-weighted images and smaller tip angles provide more $T_2$-weighted images), volumetric interpolated brain examination (VIBE), magnetic pulse rapid gradient echo (MP RAGE), fluid attenuation inverted recovery (FLAIR), a parallel imaging technique such as sensitivity encoding (SENSE), or another pulse sequence. Note that SENSE may involve: generating coil sensitivity maps, acquiring partial k-space MR data, reconstructing partial field of view images from each of RF coils 230, and combining the partial field of view images using matrix inversion. Moreover, the pulse sequence may include or may be associated with second and third generation parallel imaging techniques, such as GRAPPA, Auto-Smash or VD-SMASH, which are imaging techniques that speed up MRI pulse sequences using k-space undersampling, and the acquisition of additional lines provides a form of calibration because the coefficients of MR signals across RF coils 230 can be determined from the measurements. However, as described further below with reference to FIGS. 3-5, in some embodiments the characterization technique facilitates direct time-domain measurements, such as measurements of the free-induction decay of excited spin states, and analysis of MR signals without the use of k-space techniques or the use of a Fourier transform. Consequently, the pulse sequence may be selected accordingly. Furthermore, the pulse sequence(s) may be designed or selected to be independent of the hardware or MR scanner. For example, a pulse sequence may be designed or selected to cancel noise and amplify specific parameters of interest (which is sometimes referred to as 'quantum pumping'). (These pulse sequences may be used in NMR or MRI to quantify certain parameters in a machine-independent manner). Note that the MR scanner may not be tuned to a specific electromagnetic frequency. Instead, the receiver may have a wide bandwidth that covers the resonance frequencies of may different types of nuclei at a given magnetic-field strength.

Thus, in general, the pulse sequences may include: existing pulse sequences (when accurate measurements and simulations of the properties of the MR scanner can be obtained so that invariant MR signatures or MR models can be determined); pseudorandom pulse sequences (which may also involve accurate measurement and simulation of noise, but the pseudorandom nature may help to create more unique Bloch trajectories at each point in space); and/or quantum pumping (which may, at least in part, cancel out MR scanner-dependent noise, and thus, may simplify or reduce the required accuracy of the simulations used to determine the invariant MR signatures or MR models).

RF coils 230 also may detect the transverse magnetization as it precesses in the xy plane. In general, a given one of RF coils 230 may be transmit only, receive only or can transmit and receive RF signals. Moreover, RF coils 230 may be oriented such that the magnetic field $B_1$ is perpendicular to the magnetic field $B_0$. Furthermore, RF coils 230 may be tuned to the Larmor frequency (e.g., the resonant frequency of a type of nuclei being imaged or measured at the magnetic field $B_0$), e.g., by adjusting a capacitor or an inductor, or changing its capacitance or inductance (such as by using matching and tuning capacitors). Note that RF coils 230 may include: an Alderman-Grant coil, a bird cage (which may be used for volume measurements), a butterfly coil, a dome resonator, a gradiometer, an implantable coil, an inside out/Schlumberger coil, an intravascular coil, a ladder coil, a Litz coil, a loop-gap resonator coil, a loop-stick coil, a meanderline coil, a mouse coil, a multi-turn solenoid coil, a phased-array coil, a phased-array volume coil, a ribbonator coil, a saddle coil, a scroll coil, a single-turn solenoid coil (which may be used for extremity measurements), a spiral coil, a surface coil (which may be used for receiving body or volume signals because they have a good signal-to-noise ratio for tissues and samples adjacent to the coil), a multi-nuclear surface coil, a diffusion-tensor-imaging surface coil, a superconducting coil, a transmission-line coil, a truncated-spiral coil, a 3-axis coil, and/or a wide-band RF coil (which may be used to simultaneously excite multiple spectra). Note that coils with additional density can be designed to focus on regions of particular interest, such as: the brain, the abdomen, the chest, the reproductive, organs, spine, a joint (e.g., the neck, a shoulder, a knee, an elbow, a wrist, etc.), hands or feet. Moreover, the one or more of RF coils 230 may be full-body coils that are designed to capture the full body.

In some embodiments, one or more of RF coils 230 includes a thermal imaging sensor, which can include a forward looking infrared (FUR) sensor. (This may allow thermal imaging and MRI of, e.g., breast tissue.) Note that one or more sensors (such as the one or more of RF coils 230) in MR scanner 200 can be attached modularly (e.g., snapped together in concentric shells, snapped on additions, assembled with interlocking interfaces, etc.) and can communicate with each other via wireless or wired communication.

Furthermore, the one or more of RF coils 230 may be included in form-fitting elastic fabric that resembles football pads or suit of armor, and the size can be adjusted based on the size of individual 112. Additional RF coils can be included in hats, helmets, long-sleeve shirts, pants, gloves, socks, legwarmers, tights, jackets, vests, breeches, and/or other clothing items. For example, a measurement-equipped suit may include a soft wearable set of RF coils that is worn by individual 112, and then individual 112 can also be enclosed in a more rigid suit, such as a clamshell design. Note that the soft, wearable clothing suit may have one or more integrated ultrasonic generators attached to some or all parts of the body and/or integrated electrocardiogram sensors, and the harder outer shell may include integrated optical and thermal sensors. In some embodiments, a head coil includes: a mirror, a prism, a fiber-optic cable, a holographic display, a retinal projector, a projection screen, a stereo-projection screen, and/or another type of display for presenting visual information.

Moreover, in some embodiments surface coils that can be controlled by software on computer system 114 that executes the scan plan allow certain modalities or MR techniques to be turned on and off in real-time as the analysis of individual 112 progresses (such as during a second MR scan in response to detection of a potential anomaly, which is sometimes referred to as a 'drill down' protocol scan). For example, this approach may allow MRE to be performed on an anomaly, or a thermal image to be acquired of individual 112 or the surrounding region. Thus, if a potentially anomaly is detected in the individual's chest, the system may decide to send an ultrasonic wave through their chest during MRE of the potential anomaly and/or the surrounding region. In these embodiments, RF coils 230 can be constructed to include multiple sensors and data-collection equipment to facilitate specialized anomaly detection. Thus, RF coils 230 may be optimized for parallel collection of data using: MRT, MRS, MRE, multi-nuclear imaging of two or more nuclei (such as $^1$H, $^{23}$Na, $^{31}$P, $^{13}$C, $^{19}$F, $^{39}$K, $^{43}$Ca, etc.), diffusion-tensor imaging, N-channel scanning, magnetic-field relaxometry, etc.

In some embodiments, MR scanner 110 includes non-inductive sensing technologies in addition to or instead of RF coils 230, such as a magnetometer, a superconducting quantum interference device (SQUID), opto-electronics, etc. Note that non-inductive sensors may enable sweeping of the magnetic field generated by magnet 210 without requiring that RF coils 230 be tuned to different frequencies corresponding to the magnetic-field strengths.

The RF signals received by RF coils 230 may be amplified by RF receive amplifier 232 and detected using RF detector 234. In particular, RF detector 234 may capture or demodulate the RF signals to baseband. For example, RF detector 234 may measure MR signals in their simplest form, such as the free-induction decay of excited spin states, though it is possible to receive many more complicated pulse sequences. Computer system 114 may control RF detector 234 via interface circuit 116 (FIG. 1), network 130 (FIG. 1) and interface circuit 244. For example, computer system 114 may specify which MR (or RF) signals to capture.

Note that RF detector 234 may be a linear analog detector, a quadrature analog detector or a heterodyne receiver. Linear analog detectors may capture MR signals along one vector in the coordinate space (e.g., the magnetization along the x or y axis), and a quadrature analog detector may simultaneously capture MR signals along two vectors in the coordinate space (e.g., the magnetization along the x and they axis). In some embodiments, a linear analog detector includes a doubly balanced mixer, and a quadrature analog detector includes a pair of double balanced mixers, a pair of filters, a pair of amplifiers and a 90° phase shifter.

Furthermore, digitizer 236 may digitize the MR signals received by the RF detector 234. For example, digitizer 236 may use a 1 MHz sampling frequency. While this may oversample the MR signal, digital filtering (such as filtering using by multiplying by a bandpass filter in the frequency domain or convolving using a sinc function in the time domain) may be used to capture the desired frequencies and to remove higher frequency signals. In the process, the amount of data to be processed and stored by computer system 114 may be reduced to a more manageable level. However, in general, a variety of sampling frequencies greater than twice the Nyquist frequency may be used. For example, there may be up to 1000 samples per MR signal so that a frequency resolution of at least 500 Hz can be achieved. Computer system 114 may control digitizer 236 via interface circuit 116 (FIG. 1), network 130 (FIG. 1) and interface circuit 244. In particular, computer system 114 may specify the sampling rate and/or filter settings used by digitizer 236.

After digitizing, computer system 114 (FIG. 1) may perform a variety of digital signal processing (such as filtering, image processing, etc.), noise cancellation and transformation techniques (such as a discrete Fourier transform, a Z transform, a discrete cosine transform, data compression, etc.). In general, the MR signal may specified in the time domain and/or the frequency domain. Thus, in some embodiments, the MR signal is represented in k space. However, as noted previously, in some embodiments the characterization technique facilitates analysis of MR signals without the use of a Fourier transform.

In one embodiment, the readings from RF coils 230 are digitized within or just outside of the coil assembly and transmitted wirelessly to computer system 114 to avoid messy cable tangling, and without creating significant RF noise in the frequencies of interest. For example, the data may be transmitted to computer system 114 at lower or higher frequencies than the Larmor frequencies of targeted nuclei in individual 112, which may allow the data to be filtered to exclude noise artifacts. Furthermore, in some embodiments RF coils 230 are tuned to receive one or more frequencies. For example, depending on the spectra desired, a wide-band receiver coil can be used or a software or hardware-based tuner can be used to automatically tune at least one of RF detector 234 to receive one or more frequencies from a desired nuclei or molecule. (However, as noted previously, in other embodiments an un-tuned receiver, such as a magnetometer, is used.) Additionally, in embodiments where parallel imaging techniques are used, different parts of surface coils on individual 112 operate in parallel to concurrently or simultaneously capture different spectra.

Note that biological lifeform holder 214 may support individual 112 while individual 112 is moved through the magnetic fields and measured by MR scanner 110. Moreover, as noted previously, biological lifeform holder articulator 216 may articulate or move biological lifeform holder 214 as needed to position individual 112 in relation to the magnetic fields generated by magnet 210 and magnetic-gradient coils 222. In particular, biological lifeform holder articulator 216 may rotate individual 112 in 2D or 3D while individual 112 is being measured by MR scanner 110 based on instructions received from computer system 114 via interface circuit 116 (FIG. 1), network 130 (FIG. 1) and interface circuit 244. Furthermore, as noted previously, biological lifeform holder 214 may be enclosed in chamber 240 or may be an enclosed chamber, including a sealed chamber that can be pumped down to reduced pressure using a vacuum pump or flooded with an inert gas. In some embodiments, because environmental conditions can have an effect on individual 112, biological lifeform holder 214 includes sensors that measure temperature, humidity, pressure, another environmental condition, etc. inside the room, inside chamber 240 that contains biological lifeform holder 214, or inside biological lifeform holder 214.

In some embodiments, biological lifeform holder 214 includes a tube (or a vessel) and biological lifeform holder articulator 216 includes one or more air jets. These air jet(s) can be used to manipulate the position of individual 112. For example, the tube can be made of glass (such as optically clear or transparent glass), Teflon (which may be transparent at other frequencies of electromagnetic radiation), or another suitable material. Moreover, the tube may include features on its outer surface (such as a texture, fins or other features) that enable individual 112 to be articulated or manipulated into different positions using a gripping or interlocking interface to a motor or robotic arm, thereby allowing system 100 (FIG. 1) to re-orient individual 112 during the indexing or sample-measurement process.

Moreover, the tube may be inserted into a multi-axis magnet, such as a multi-axis magnet provided by Cryomagnetics, Inc. of Oak Ridge, Tenn. Then, system 100 (FIG. 1) can probe or measure individual 112 from multiple directions, angles, perspectives and alignments without requiring multiple sensors around bore 236. For example, individual 112 may be rotated, and a single camera, CCD or CMOS sensor can capture multiple photographs of individual 112 so that images of some or all of individual 112 may be captured, thereby reducing the cost and complexity of system 100, and improving the reliability. Furthermore, the tube may provide the chamber that is under vacuum or that is filled with an inert pre-polarized gas to increase the resolution. In some embodiments, a low-cost and portable chip-scale device (such as a microfluidic chip) is used to produce the polarized or magnetized gas, so that faint MR signals can be detected. For example, as noted previously, polarized xenon can be used as a contrast agent to enhance images in MRI of, e.g., human lungs. The polarized xenon atoms may be produced in the chip by collisions with rubidium atoms that are illuminated with circularly polarized light. Then, the polarized xenon may flow out of the chip and may be directed into the tube or chamber 240.

While not shown in FIG. 2, in some embodiments MR scanner 110 includes a watchdog or another automatic failsafe safeguard that monitors MR scanner 110. For example, the watchdog or automatic failsafe safeguard may monitor the specific absorption rate of individual 112 using thermal imaging. If a high or dangerous level of specific absorption is detected (such as one that may be perceived or that may cause pain or injury), computer system 114 (FIG. 1), via interface circuit 116 (FIG. 1), network 130 (FIG. 1) and interface circuit 244, may control pulse sequences to slow down or interrupt a current MR scan.

Referring back to FIG. 1, computer system 114 may instruct one or more optional measurement devices 124 to perform other measurements on individual 112 to obtain physical property information that specifies a measured physical property of individual 112, which may be used to determine a diagnostic classification of individual 112 and/or which may be included in metadata associated with individual 112. For example, the one or more optional measurement devices 124 may include: a medical grade scale that determines a weight of individual 112; a measurement device that measures one or more dimensions of individual 112 (such as: a laser imaging system, an optical imaging system, an infrared imaging system, and/or a spectroscopy system); a light source that can selectively illuminate individual 112 and a camera-enabled microscope that acquires or measures one or more optical images of individual 112 at one or more perspectives, orientations or lighting conditions; and/or a bioelectric impedance analyzer that performs a multi-lead measurement of an impedance of individual 112 at DC or an AC frequency (and which may correspond to hydration of individual 112, and thus may be used to determine or compute the hydration of individual 112). Alternatively, the hydration or hydration level, which can affect individual 112, and thus the invariant MR signature or the MR model, may be measured directly. In some embodiments, the other measurements on individual 112 include: cell cytology, genetic sequencing (such as sequencing some or all of the DNA in the genome, RNA sequencing or transcriptomics, gene expression, etc.), protein analysis or proteomics (e.g., using mass spectrometry, metabolomics, liquid chromatography and/or NMR), epigenetic sequencing, lipidomics, microbiomics, radiomics, cytomics, toxomics (i.e., measurement of non-biological compounds in individual 112), an electrical measurement (such as an electrocardiogram, an electromyogram, an electroencephalogram, etc.), motion detection (such as body movement), acceleration, one or more vital signs, computed tomography, electron-spin resonance (which may be used to measure free radicals), x-ray imaging, ultrasonic imaging (e.g., ultrasound), photo-acoustic imaging, infrared imaging or infrared spectroscopy, other non-destructive measurements (such as radar or millimeter-wave scanning), activity or behavior data for an individual (such as data capture using a wearable electronic device), measurements performed by nano particles in individual 112, chemical composition of fluids (such as blood) measured at arbitrary locations in individual 112 non-destructively or by drawing a blood sample (e.g., using microfluidics), another quantitative or qualitative characteristic or property of individual 112, etc. Alternatively, computer system 114 may access data for some or all of these other measurements that are stored in a remote data structure (such as the biovault) based on the unique identifier for individual 112.

Note that the weight and the dimensions of individual 112 may be used to calculate their density. Moreover, the one or more optional measurement devices 124 may acquire images of individual cells for inspection and pathology identification. Furthermore, the medical grade scale may provide information about the chemical composition and hydration levels of individual 112 if individual 112 is weighed. The weight may be measured before and/or after the MR scanning (or other imaging operations). In some embodiments, measuring individual 112 in different portions of the electromagnetic spectrum may allow a correction for susceptibility artifacts that may not show in optical or infrared scans, but that can occur in certain radio scans.

In some embodiments, system 100 includes an optional wave generator 126 that is controlled by computer system 114 via interface circuit 116. This optional wave generator may generate ultrasonic waves (and, more generally, mechanical waves) that are applied to individual 112 during MRE to measure a stiffness of individual 112. For example, optional generator 126 may generate waves at one or both ends of bore 236 (FIG. 2) of MR scanner 110 or may direct waves at one of both ends of bore 236 (FIG. 2) of MR scanner 110 using a waveguide, such that individual 112 receives the ultrasonic waves. In some embodiments, the ultrasonic waves include sheer waves. MR scanner 110 may acquire quantitative MR signals of the propagation of the shear waves through individual 112, and may process the images of the shear waves to produce a quantitative mapping of the tissue stiffness.

(If, instead of an individual, a tissue sample that is embedded in formalin fixed-paraffin, then after the invariant MR signature is determined computer system 114 may transform the determined invariant MR signature so that it approximates an in-vivo tissue, i.e., without the formalin or the paraffin. For example, on a voxel-by-voxel basis, computer system 114 may subtract a predefined or predetermined invariant MR signature of the formalin or the paraffin from the determined invariant MR signature to generate an estimated invariant MR signature. Alternatively, computer system 114 may correct the parameters in the MR model on a voxel-by-voxel basis for the formalin or the paraffin to generate an estimated invariant MR signature. In some embodiments, a partial volume technique is used to subtract out the contribution or the effect of the paraffin or wax at borders of the tissue sample. In particular, computer system 114 may determine what percentage of a given voxel is paraffin and may remove or subtract out that weighted portion of the invariant MR signature or the MR signals that are used to computer the invariant MR signature.)

Furthermore, computer system 114 may store the raw data (such as MR signals from a biological sample or lifeform, the applied non-ideal pulse sequences, and measured noise), the invariant MR signature(s), the MR model(s) and/or other measurements in the biovault, such as in memory 120 (which may be locally and/or remotely located, such as in a cloud-based archive device). In general, the measured information stored in the biovault may be sufficiently encompassing to allow the MR model to be trained based on the scanning instructions (e.g., using training engine 128) and, thus, the invariant MR signature(s) or MR model(s) to be determined. Note that training engine 128 may train or generate the MR model and may not: require previous training or information in order quantify tissue parameters or automatically segment tissues/structures; and/or rely on a non-deterministic, statistical, or pattern matching technique. In general, the training engine 128 may use equations that represent the physics (the forward model) and may determine parameters to model the dynamic response of one or more volume(s) in a sample to an arbitrary excitation that is applied to the sample provided that the physics are not changing during the measurements on the sample. Thus, the stored information may include different output signals at different points in the measurement pipeline (e.g., before an amplifier, after the amplifier, etc.), environmental conditions, geographic location, etc. The stored information may facilitate accurate simulations of an MR scan and individual 112, e.g., by training an MR model.

The stored information may include or may be associated with the unique identifier or a new unique identifier generated by computer system 114 that facilitates subsequent identification, as well as searching or querying of the biovault. Thus, if individual 112 is subsequently re-measured at a later time, computer system 114 may store the results or differential results (such as any changes in the invariant MR signatures) so that changes since the last measurements can also be used for searching. Moreover, the stored information may include information about the time, location and/or system parameters (such as information that specifies or identifies MR scanner 110) when individual 112 was measured. Note that the stored information may be encrypted. For example, symmetric or asymmetric encryption based on an encryption key associated with the unique identifier may be used.

In some embodiments, computer system 114 optionally compares the invariant MR signature or MR model of individual 112 to one or more other invariant MR signatures or MR models, which may have been previously determined for individual 112 or another individual. (Alternatively, computer system 114 may optionally compare a measured MR signal or one calculated from or based on the determined invariant MR signature or MR model with one or more predetermined MR signals.) Based on this comparison, computer system 114 may optionally determine a classification of individual 112 (such as a diagnosis), which may be stored in the biovault along with or associated with the unique identifier. Note that the determined or selected classification may be the one that has the lowest chance of being a classification error or the lowest matching error. Furthermore, if there are multiple potential or candidate classifications that have similar estimated classification errors (e.g., based on a predetermined supervised-learning model), then the classification of a given voxel may be determined based on a priori information, e.g., the classifications of nearby voxels or combinations (such as linear combinations) of these neighboring classifications, which may help reduce the classification error of the given voxel.

The ability to track labels or classifications and outcomes over time may allow the system to take an invariant MR signature or MR model and look up information that is known about it, such as: how frequently it is found, in which organs, has it been labeled bad or good, in which circumstances was it labeled bad or good, etc. In this way, the metadata about the invariant MR signatures of MR models may get richer over time. For example, an individual (or tissue samples from the individual) may be indexed every six months. If cancer occurs during one of these indexing operations, this invariant MR signature or MR model may be labeled 'bad.' But what about the classifications of historical MR signatures or MR models in that same region of individual 112? Does the cancer diagnosis potentially make them pre-cancerous? The system may find enough evidence, based on multiple MR scans, that the earlier MR signatures or MR models are early indictors of cancer and that there is a path through the MR-signature or MR-model space is characteristic of this pathology evolving over time. Consequently, the biovault may allow such longitudinal and cross-individual analysis to identify such paths, which can be use in subsequent classifications and diagnoses, e.g., to detect one or more potential anomalies (such as a tumor).

Moreover, by comparing longitudinally for a particular individual and/or across individuals within the biovault, the system may be able to solve problems and assist in identifying pathologies without requiring the use of a deterministic machine-learning or supervised-learning model. For example, the system may be able to differentially identify the presence of a foreign object (such as screws, pins, joint replacements, etc.) embedded in individual 112 even if the biovault does not include or does not have previous knowledge about the foreign object. In particular, a ferromagnetic or paramagnetic material may be detected based on the resulting magnetic-field distortion, and the invariant MR signature or the MR model may include a correction for this magnetic-field distortion.

In some embodiments, the biovault provides the ability to aggregate invariant MR signatures or MR models on related individuals in other biovaults without these biovaults sharing other information about the individuals. This may allow global analytics to be performed on the individuals in siloed or isolated biovaults.

(If, instead of individual 112, a tissue sample is measured, system 100 may use an optional vacuum sealer to enclose and seal the tissue sample in vacuum in preparation for archival storage. Moreover, in some embodiments, the tissue sample is formalin fixed-paraffin embedded after the measurements. Furthermore, a physical or an electronic label may be attached to or associated with the tissue sample by an optional labeler to facilitate subsequent identification. The information in the physical or electronic label may include the information input and/or extracted at the start of the characterization technique. In some embodiments, the tissue sample is destroyed after measurements are made.)

While the preceding discussion illustrated the use of system 100 to scan or index individual 112, in other embodiments system 100 may be used to scan or index an individual or an animal multiple times, or multiple MR scans of different persons or animals. These scans may partially or fully overlap in time (i.e., may, at least in part, occur concurrently or simultaneously) to increase throughput.

Moreover, while the preceding discussion illustrated the technician or the MR operator using system 100, in other embodiments system 100 is highly automated, so that individual 112 may be loaded into MR scanner 110, MR measurements and/or the other measurements may be performed, one or more potential anomalies may be detected, an invariant MR signature or MR model can be determined, information may be stored in the biovault, individual 112 may be removed, and these operations can be repeated for one or more additional MR scans with minimal or no human action.

Figure 3:
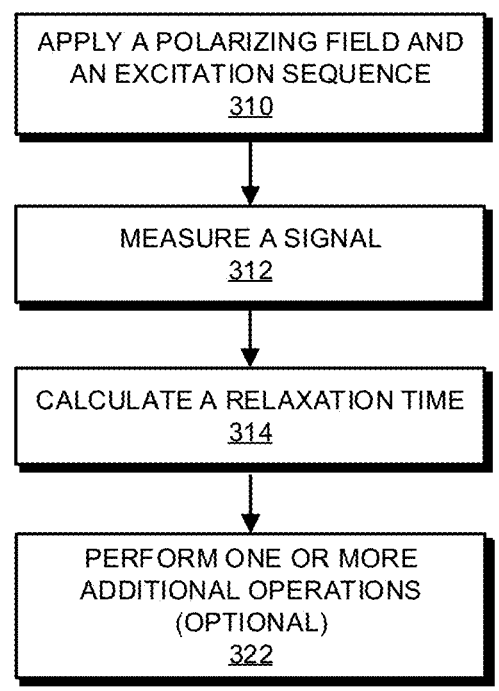
FIG. 3 is a flow diagram illustrating a method for determining a relaxation time associated with a sample in accordance with an embodiment of the present disclosure.

We now further describe the characterization technique. FIG. 3 presents a flow diagram illustrating a method 300 for determining a relaxation time associated with a sample. This method may be performed by a system, such as system 100 in FIG. 1. During operation, the system may apply a polarizing field and an excitation sequence (operation 310) to the sample. For example, the system may include a generating device that generates a field, such as magnet 210, magnetic gradient coils 222 in FIG. 2.

Then, the system may measure a signal (operation 312) associated with the sample for a time duration that is less than a magnitude of the relaxation time. For example, the system may include a measurement device that performs measurements, such as RF coils 230 in FIG. 2.

Note that the polarizing field may include an external magnetic field, the excitation sequence may include an RF pulse sequence, the measured signal may include a component of a magnetization of the sample, and the relaxation time may include a longitudinal relaxation time along a direction parallel to the external magnetic field (such as $T_1$) or a transverse relaxation time along a direction perpendicular to the external magnetic field (such as $T_2$). For example, the relaxation time may be associated with a type of nuclei in the sample and/or a type of tissue in the sample.

Next, the system may calculate the relaxation time (operation 314) based on a difference between the measured signal and a predicted signal of the sample, where the predicted signal is based on a forward model, the polarizing field and the excitation sequence.

In some embodiments, the system optionally performs one or more additional operations (operation 316). For example, the system may apply a gradient to the polarizing field along a direction in the sample, where the relaxation time is calculated on a voxel basis in the sample.

Moreover, the system may: modify at least one of the polarization field and the excitation sequence; apply at least the one of the modified polarization field and the modified excitation sequence to the sample before the sample has completely relaxed or without resetting a state of the sample; measure a second signal associated with sample for a second time duration that is less than the magnitude of the relaxation time; and calculate the relaxation time based on a second difference between the second measured signal and a second predicted signal of the sample, where the second predicted signal is based on the forward model, the polarizing field and the excitation sequence. Additionally, the system may determine a dynamic state of the sample based on the forward model, the polarizing field and the excitation sequence, where the dynamic state when at least one of the modified polarization field and the modified excitation sequence is applied to the sample may be used as an initial condition when calculating the relaxation time based on the second difference.

Furthermore, the calculation of the relaxation time may be performed concurrently with the measurement of the signal. In some embodiments, the relaxation time is calculated continuously during the measurement of the signal and the second signal.

Note that at least one of a magnitude and a direction of the polarizing field may be changed as a function of time during the measurement.

Additionally, the relaxation time may be calculated without performing a Fourier transform on the measured signal.

Figure 4:
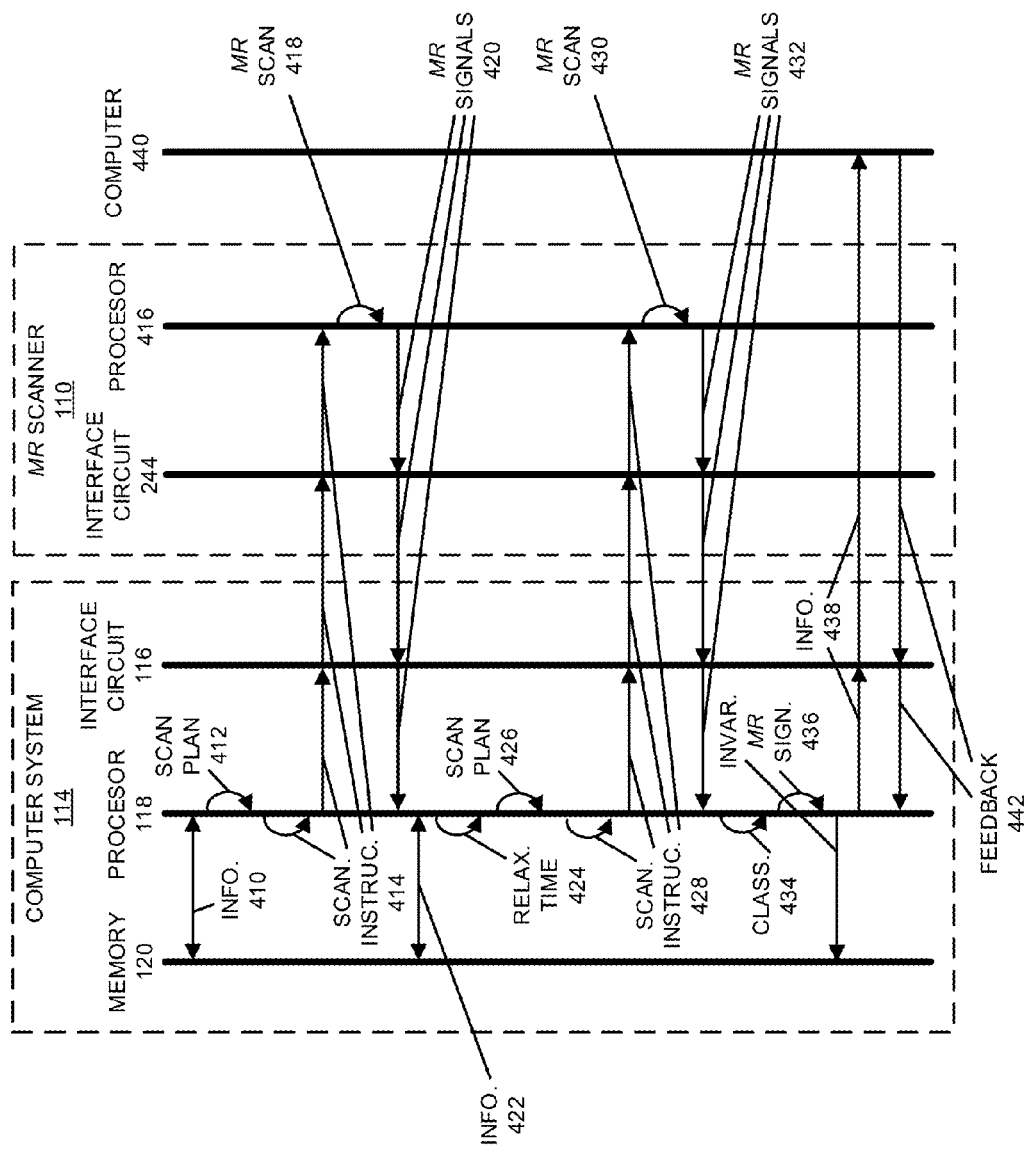
FIG. 4 is a drawing illustrating communication among components in the system in FIG. 1 in accordance with an embodiment of the present disclosure.

FIG. 4 presents a drawing illustrating communication among components in system 100 in FIG. 1. In particular, processor 118 in computer system 114 may access information 410 in memory 120. Using this information, processor 118 may determine a scan plan 412 and scanning instructions 414. Then, processor 118 may provide, via interface circuit 116, scanning instructions 414 to MR scanner 110.

After interface circuit 244 receives scanning instructions 414, processor 416 may execute them, so that MR scanner 110 performs an initial MR scan 418. During MR scan 418, MR scanner 110 may acquire or capture MR signals 420, which are provided to computer system 114.

Processor 118 may analyze MR signals 420 to determine a relaxation time 424. This analysis may involve: registration, alignment, segmentation, determination of parameters in an MR model, simulation or estimation of MR signals using the MR model, and/or comparison of MR signals 420 with one or more templates. During the analysis, processor 118 may access additional information 422 in memory 120.

Based on residual differences between MR signals 420 and the estimated MR signals, processor 118 may dynamically update scan plan 426. Then, processor 118 may determine updated scanning instructions 428, which are provided to MR scanner 110.

After MR scanner 110 receives scanning instructions 428, processor 416 may execute them, so that MR scanner 110 performs MR scan 430. During MR scan 430, MR scanner 110 may acquire or capture MR signals 432, which are provided to computer system 114.

Note that processor 118 may repeat one or more of the aforementioned operations until the MR scan(s) of the individual are completed and/or a desired accuracy of one or more determined parameters (such as relaxation time 424) is achieved. Furthermore, processor 118 may determine classification(s) 434 of one or more potential anomalies and/or an invariant MR signature 436 or an MR model based on the measured MR signals, which is stored in memory 120. Processor 118 may also store the MR signals, metadata and other related information in memory 120.

In addition, computer system 114 may provide information 438 about the MR scan(s) to a third party (such as a radiologist), such as to a computer 440 associated with the third party. Subsequently, computer 440 may provide feedback 442 from the third party that is used to update the current scan plan, a future scan plan, a recommended future scan time, one or more templates, etc.

Figure 5:
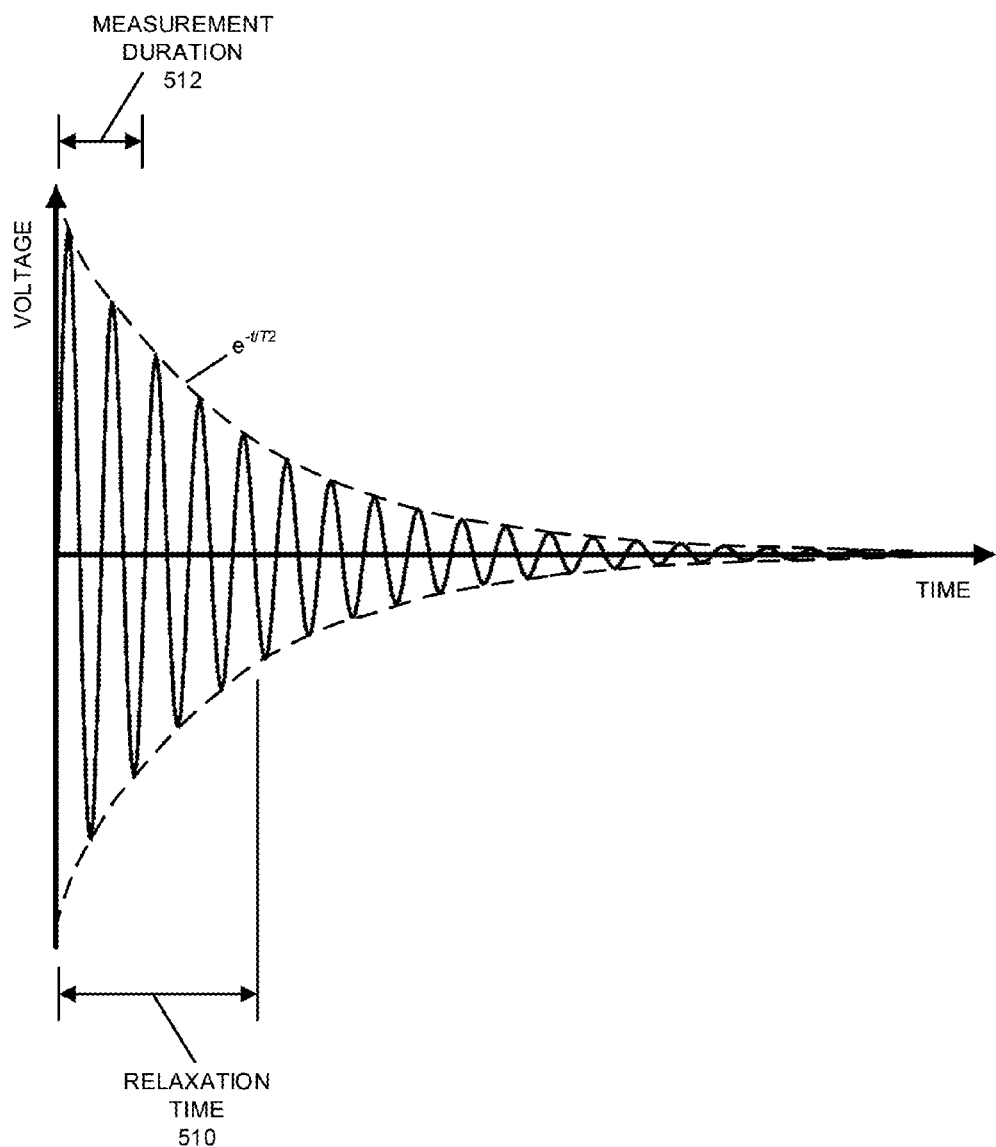
FIG. 5 is a drawing illustrating the determination of a relaxation time associated with a sample in accordance with an embodiment of the present disclosure.

FIG. 5 presents a drawing illustrating the determination of a relaxation time associated with a sample. In particular, FIG. 5 illustrates the measured voltage as a function of time during a free-inductive decay. While the nuclei spin oscillate at the Larmor frequency, the magnitude of the peak magnetization decreases exponentially with a time constant $T_2$, which includes contributions from the sample as well as extrinsic factors (such as inhomogeneity in the external magnetic field). Note that the decay of the magnetization along the direction of the external magnetic field has a similar exponential decay with a time constant $T_1$.

In existing MR techniques (such as MRI), the time constants are typically determined using a scan or measurement duration that is at least an integer multiple of $T_1$ or $T_2$. As shown in Table 1, there is considerable variation of $T_1$ and $T_2$ in different types of tissue. Consequently, accurate determination of these relaxation times often involves measurements for seconds to hundreds of seconds. In addition, in existing MR techniques the spins are usually returned to a known state prior to a subsequent measurement (such as a subsequent RF pulse sequence). Typically, this is achieved by waiting for a time duration much larger than $T_1$ and $T_2$, or by re-magnetizing the spins along the external magnetic field.

TABLE 1

| Tissue | $T_1$ (s) | $T_2$ (ms) |
| --- | --- | --- |
| Cerebrospinal Fluid | 0.8-20 | 110-2000 |
| White Matter | 0.76-1.08 | 61-100 |
| Gray Matter | 1.09-2.15 | 61-109 |
| Meninges | 0.5-2.2 | 50-165 |
| Muscle | 0.95-1.82 | 20-67 |
| Adipose | 0.2-0.75 | 53-94 |

In contrast, in the characterization technique, relaxation time 510 (such as $T_1$, $T_2$ or the adjusted spin-spin relaxation time $T_2^*$) may be accurately determined using a measurement duration 512 that is a fraction of the relaxation time being determined. For example, for cerebrospinal fluid, the measurement duration may be 0.55 s, instead of hundreds of seconds. This is because the iterative comparisons of the measured MR signals and the estimated MR signals based on the MR model allows the model parameters, including $T_1$ or $T_2$, to be rapidly and accurately determined (i.e., with a high signal-to-noise ratio) without significant (or any) synchronous averaging over multiple instances of the measurement.

Moreover, the characterization technique may allow real-time computing of the relaxation time, as opposed to retroactively or after the MR measurements. Indeed, in some embodiments the MR measurements and the calculation of the MR model parameters is performed continuously.

Furthermore, the state of the nuclei spins may be dynamically tracked during the characterization technique, and the current state may be used as the initial condition in the next iteration of the simulations or prediction of the MR signal. Consequently, in the characterization technique the MR scanner may not have to pause between a first MR scan and a subsequent MR scan. Thus, the MR scanner may not have to wait for the nuclei spins to decay to an appropriate level (i.e., for a time duration that is longer than $T_1$, $T_2$ or the adjusted spin-spin relaxation time $T_2^*$) or may not need to re-magnetize to the nuclei spins along the external magnetic field. Therefore, this capability may allow the MR scanner to modify the external magnetic field (i.e., to change the magnitude and/or the direction of the external magnetic field) and/or the RF pulse sequence before the nuclei spins in the sample are fully relaxed or reset to predefined state.

In some embodiments, the parameters in the MR model are determined based time-domain measurements of one or more components of the magnetization in the sample. In particular, the parameters (including the relaxation time(s)) may be determined without using a Fourier transform (such as a discrete Fourier transform) by performing MR measurements at a high temporal sampling rate (such as at a rate equal to or higher than twice a frequency of interest in the estimated MR signals). This capability may simplify the signal processing in the analysis of the measured MR signals and/or may provide additional degrees of freedom in the types of RF pulse sequences that can be used.

Therefore, the characterization technique may facilitate significantly faster scan times than existing MR techniques. Moreover, the characterization technique may facilitate quantitative analysis of MR signals without requiring the use of a phantom or by merely comparing intensities. In addition, the characterization technique may allow the use of lower external magnetic fields and/or external magnetic fields that have more spatial magnetic-field inhomogeneity than the large (and expensive) toroidal superconducting magnets using in most MR scanners. For example, the characterization technique may allow different configurations of the external magnets (such as an open configuration or a configuration where the patient is seated), the elimination of the superconducting magnets or the elimination of the external magnet. Thus, in some embodiments the characterization technique may facilitate a portable or a hand-held MR scanner. Consequently, the characterization technique may reduce the cost of MR scans, and may significantly improve the patient experience during MR scans.

We now describe determination of one or more parameters in an MR model. This MR model may be a 3D model of voxels in a portion of an individual (and, more generally, a sample), and may include parameters in the Bloch equations for each of the voxels. In particular, with a quasi-static magnetic field $B_0$ along the z axis, the Bloch equations are $$\frac{DM_x(t)}{dt} = \gamma \cdot \left(\vec{M}(t) \otimes \vec{B}(t)\right)_x - \frac{M_x(t)}{T_2},$$

$$\frac{dM_y(t)}{dt} = \gamma \cdot \left(\vec{M}(t) \otimes \vec{B}(t)\right)_y - \frac{M_y(t)}{T_2}, \text{ and}$$

-continued
$$\frac{dM_z(t)}{dt} = \gamma \cdot \left(\vec{M}(t) \otimes \vec{B}(t)\right)_z - \frac{M_z(t) - M_0}{T_1},$$

where $\gamma$ is the gyromagnetic ratio, $\otimes$ denotes a vector cross product and $\vec{B}(t)=(B_x(t), B_y(t), B_0+\Delta B_z(t))$ is the magnetic field experienced by a type of nuclei in the individual. The parameters in the Bloch equations may include $T_1$, $T_2$, a density of a type of nuclei, diffusion, velocity/flow, temperature, and magnetic susceptibility. Note that there may be different parameters for different types of nuclei for each of the voxels. Moreover, note that the Bloch equations are a semi-classical, macroscopic approximation to the dynamic response of the magnetic moments of the type of nuclei in the individual to a time-varying magnetic field. For example, there may be 67 M cells in a 1 $mm^3$ voxel.

In principle, the solution space for the parameters in the Bloch equations for the individual may be underdetermined, i.e., there may be significantly more parameters to be determined than there are observations with which to specify or constrain the parameters. Therefore, the characterization technique may leverage additional information to constrain or reduce the dimensionality of the problem. For example, an aspect of the anatomy of the individual may be determined using other imaging techniques, such as computed tomography, x-ray, ultrasound, etc. Moreover, regions that do not look like (i.e., that has very different MR signals) than a targeted type of tissue (such as heart tissue) may be excluded from the MR model. In this way, for example, regions that consist of air may be excluded. Alternatively or additionally, tissue that deviates significantly from the expected MR signals based on previous MR scans (e.g., anomalies or changes) may become the focus of the MR model, such as by using a contour map (e.g., a cubic spline) to bound the regions (or specify a boundary of the regions) where there are significant differences. In some embodiments, the error between measured MR signals and simulated or estimated MR signals may be represented using one or more level-set functions, and the boundaries of regions with errors exceeding a threshold value may be determined based on the intersection of a plane corresponding to the threshold value and the one or more level-set functions. In addition, by performing scans at different magnetic-field strengths $B_0$ (which may provide similar information to pseudorandom pulse sequences) using different pulse sequences and/or different MR techniques, the ratio of parameters to observations may be reduced, thereby simplifying the determination of the MR model.

For example, if a portion of the individual included one voxel, there may be 4-10 MR model parameters (which specify an invariant MR signature or an MR model) that need to be determined for a particular type of tissue. If the voxel includes M types of tissue, there may be 4M-10M MR model parameters (which may specify M invariant MR signatures) that need to be determined for the particular type of tissue. As the number of voxels increases, this can appear to be a daunting problem.

However, because different types of nuclei have different Larmor frequencies, the spatial distribution of the types of nuclei and their local concentrations may be determined from the measured MR signals. Then, a predefined anatomical template for the human body (or a portion of the human body), with associated initial parameters for an MR model, may be scaled to match the spatial distribution of the types of nuclei and their local concentrations.

Next, for a type of tissue (such as a particular organ), the MR model parameters may be iteratively refined as the size of the voxels is progressively decreased (and, thus, the number of voxels is increased). This analysis may be driven by the error between the measured MR signals and simulated or estimated MR signals using the MR model. Over time, the focus during the training will be on the residual regions with errors that are larger than a convergence criterion. For example, the parameters in the MR model may be trained based on measured MR signals at one magnetic-field strength and then the error may be determined based on the predictions of the MR model at another magnetic-field strength. Furthermore, note that initially the MR model may assume that there is no contribution or interaction between different voxels. However, as the error and the voxel size are reduced, subsequently such contributions and/or interactions may be included when training the MR model.

In order to facilitate this fitting or computational approach, the characterization technique may determine 'surface signatures,' as opposed to 1D signatures. For example, using measurements at multiple magnetic-field strengths or in the presence of known magnetic-field disturbances (such as rotation), a set of MR trajectories in a multidimensional space may be determined and may be used to determine the invariant MR signature(s) and/or MR models. Note that each MR trajectory may be defined by a magnetic-field function rather than a fixed magnetic-field strength.

In an exemplary embodiment, a simulation that is used to determine the MR model may be vertex/voxel centric. Using a physical model (such as a Bloch-equation-based model) running at each vertex, the system may 'apply' RF pulse sequences or disturbance to the physical model of the individual being scanned. For example, a message may be broadcast to the vertices that describe the disturbance in terms of the physics. Each of the vertices may compute its predicted change in state and the resulting forces and energies, which are then relayed as messages to adjacent vertices about the forces and energies exported from that vertex. When all the vertices have generated a message, the message has been forwarded to the adjacent vertices and the state of the system has been updated, a time interval in the calculation may be complete. This approach can be generalized so that the message is forwarded to non-cyclical paths of length N (where N is an integer) radiating out from the vertex to improve the accuracy of the simulation.

Once the state has been updated, a computational technique can be run over the new computed state and then compared to the measured state. The error may be the difference between the predicted state and the measured state. As the computational technique is applied, the system may determine how to optimally assign the current state to each vertex in a way that reduces or minimizes the global error. Next, the system may choose a new set of perturbations for the system and may broadcast these as a new message to the vertices, as well as executing this disturbance physically on the individual being scanned. In this way, the system may provide real-time or near-real-time analysis and feedback during the characterization technique. Therefore, in some embodiments, the determination of the model parameters may occur currently with the MR measurements. Indeed, in some embodiments the model parameters may be determined continuously during the MR measurements.

Thus, the inverse problem of determining the MR model parameters based on measured MR signals may be 'solved' by minimizing the error or difference between the measured MR signals and simulated or estimated MR signals that are generated based on the MR model, characteristics of the MR scanner (such as magnetic-field inhomogeneity) and the scanning instructions used to acquire the measured MR signals. In some embodiments, the inverse problem is solved using one or more computational techniques, including: a least-squares technique, a convex quadratic minimization technique, a steepest descents technique, a quasi-Newton technique, a simplex technique, a Levenberg-Marquardt technique, simulated annealing, a genetic technique, a graph-based technique, another optimization technique and/or Kalman filtering (or linear quadratic estimation).

Note that the inverse problem may be solved using dynamic programming. In particular, the problem may be divided up and performed by multiple computers in parallel, e.g., in a cloud-based computing system. For example, a particular thread may attempt to solve the inverse problem for particular scanning instructions. Multiple potential parameter solutions generated by the computers (or processors) may be combined (e.g., using linear superposition) to determine an error metric that is minimized using the one or more computational techniques.

Moreover, as described previously, the inverse problem may be solved iteratively by first attempting to find suitable parameters (e.g., parameters that minimize the error between the MR signals and simulated or estimated MR signals) for the MR model using a coarse voxel size and then progressively finding suitable parameters with smaller voxel sizes. Note that the final voxel size used in this iterative procedure may be determined based on the gyromagnetic ratio of a type of nuclei being scanned. The voxel size can also be determined based on the kind of 'query' that is made to the biovault or that forms the based on the MR scan plan, the current hardware configuration and/or hardware limitations. Furthermore, the voxel size or locations may also be chosen so that a voxel is evenly portioned into a set of subvoxels, or so that there is certain amount of overlap with preview voxel sizes to effectively "oversample" the overlapping region and potentially further localize where an MR signal originates. This last technique may be akin to shifting the entire gradient system in one or more dimensions by a distance dx that is less than a characteristic length of the voxels (such as a length, a width or a height of the voxels). In some embodiments, the voxel size in the MR model is smaller than that used in the MR scans (i.e., the MR model may use a super-resolution technique).

Additionally, the MR model may include simulations of dynamics, such as motion associated with: respiration, a heartbeat, blood flow, mechanical motion, etc. (Thus, there may be additional terms in the Bloch equations for diffusion, thermometry, spectroscopy, elastography, etc. Consequently, the MR model may be based on the Bloch-Torrey equations, etc.) For example, when a voxel contains a space that has a fluid flowing through it (such as in a vein), the flow of the liquid may be simulated by building a map of the flow directions and velocity magnitudes in the individual being scanned to be accounted for in the computation of the invariant MR signature or the MR model. Furthermore, when scanning a human or an animal, the MR model may include the resting motion (such as that associated with respiration, a heartbeat, etc.). As noted previously, in order to facilitate calculation of the MR model, measured MR signals and/or other temporal measurements may be synchronized with or relative to a reference clock or a biological time period.

The MR model may be used to predict how the individual's body will respond to particular scanning instructions. In particular, the MR model may be used to simulate or estimate the MR signals for a particular MR scanner having particular characteristics, for particular scanning instructions and/or for a particular individual (who has a medical history, previous MR scan results, etc.). Stated different, an invariant MR signature or an MR model may be used to determine representations or projections (i.e., the MR signals) in particular contexts, such as based on the particular characteristics of the MR scanner, the particular scanning instructions and/or the particular individual.

Thus, the MR model may allow system 100 (FIG. 1) to perform active learning. In particular, the MR model may be iteratively fit or determined based on 'queries' generated by a learning system or a learning engine (which may be implemented in computer system 114 in FIG. 1). In particular, the queries generated by the learning engine may include different magnetic-field strengths $B_0$, different RF pulse sequences and/or different ultrasonic pulse sequences that are based on confidence intervals for parameters in the MR model. Consequently, the learning engine may use the measured MR signals in response to these queries to determine unknown parameters in the MR model and/or parameters having a poor accuracy (such as a confidence interval greater than 0.1 1, 5 or 10%). More generally, the adaptive learning performed by system 100 (FIG. 1) may be based on a wide variety of measurements, such as optical/infrared spectroscopy, x-ray, computed tomography, proton beam, photoacoustic, ultrasound, etc.

In an exemplary embodiment, computer system 114 (FIG. 1) first approximates the parameters in the MR model and computes the error (or difference vector) between the measured MR signals and simulated or estimated MR signals based on this initial MR model. Note that when there are multiple candidate parameter solutions (having similar errors) to the inverse problem for a thread corresponding to particular scanning instructions, computer system 114 (FIG. 1) may keep the candidates (i.e., a unique parameter solution may not be identified at this point in the calculation). Alternatively, if there is no unique parameter solution within a desired error range (such as less than 50, 25, 10, 5 or 1%), the best (least-error) parameter solution may be kept. In addition, when there is no parameter solution within the desired error range, computer system 114 (FIG. 1) may modify the scanning instructions.

Moreover, computer system 114 (FIG. 1) may compute first and second derivatives along a surface(s) of parameter solutions in the individual. (In order to facilitate calculation of a derivative, note that the parameters may be represented using one or more level-set functions.) A set of voxels along the line where the first derivative is zero may be identified. This set of voxels may be fit using a cubic spline with a minimum error between the voxel positions and the cubic spline. This fitting operation may be repeated at all the boundaries in the parameter-solution space. Moreover, the largest continuous surface within the boundary defined by the cubic splines may be determined and the parameter-solution calculation may be repeated to determine a new continuous surface that is within the previous continuous surface. This generalized framework may minimize the error across intra-voxel volumes, thereby improving the agreement between the MR signals and the simulated or estimated MR signals based on the MR model.

For example, the inverse problem may be solved using a Jacobian matrix of the parameters for the voxels in the MR model and Newton's method to iteratively modify the parameters for the voxels based on how perturbations in the parameters affect the difference between the measured MR signal and the estimated MR signal. During the RF pulses, the MR signal may be estimated by solving a system of equations (such as the Bloch equations) numerically because, for $^1H$, the RF pulses are close to or at Larmor frequency for $^1H$ (this may not be the case for other types of nuclei). In particular, Runge-Kutta method 4 may be used to determine the numerical solution to a differential equation for the rotating coordinate system. The effect of gradient changes can be solved analytically because the time scale (milliseconds) is much lower than the Larmor frequency.

In some embodiments, the dynamics of the magnetization associated with the nuclei spins is decomposed into relaxation along the direction of the external magnetic field per $T_1$ and rotation and relaxation per $T_2$ in plane perpendicular to the direction of the external magnetic field. However, the analysis in the characterization technique does not require an assumption about a rotating frame of reference or a particular direction of polarization. As noted previously, the magnitude and/or the direction of the external magnetic field may be changed as a function of time. This may allow the external magnetic field to be swept over a range of magnitudes and/or directions in order to characterize anisotropy (as opposed to the structured excitation using in existing MR techniques), such that the relaxation times that are determined are with respect to or associated with different axes or directions. Alternatively or additionally, the characterization technique may use weaker external magnetic fields and/or external magnetic fields that have more spatial inhomogeneity than existing MR techniques. Indeed, the polarizing external magnetic field may be weaker than the excitation field, such as the RF pulses.

In some embodiments, the analysis in the characterization technique alternates between the Bloch equations (or something more sophisticated, such as the full Hamiltonian) and Maxwell equations in the forward model to rapidly calculate magnetic properties of the sample volume and electric properties of the sample volume. In this way, the estimates provided using one forward model can be used to regularize the estimates from the other forward model. This approach may accelerate converge and may allow the permittivity and the conductivity of each voxel to be determined in the parameters for the MR model.

In an exemplary embodiment, 2-3 iterations of measurement of MR signals and modification of the parameters in the MR model are needed to obtain values of the parameters for the voxels to less than 1% accuracy. This may be an order of magnitude better than MR fingerprinting and, at least in some embodiments, may be determined without requiring the use of pre-existing data structure with prior results for the parameters.

However, in some embodiments, a priori knowledge is used to constrain the inverse problem. For example, predetermined or predefined ranges for the parameters in different types of tissue may be used to determine the initial values of the parameters. Alternatively or additionally, values of the parameters based on previous MR measurements may be used as the initial values of the parameters in a current instance of the analysis in the characterization technique. Other constraints during the analysis may include: thermodynamic constraints on heat flow (from hot to cold) for perfusion or MRT to quantify metabolism and/or Maxwell's equations constraints.

Note that the characterization technique may allow spatial distributions of relaxation times and densities in inhomogeneous tissues to be determined. For example, the characterization technique may allow voxel-by-voxel densities and relaxation times for an inhomogeneous sample to be estimated.

In some embodiments, the geometry of the voxels in the MR model may be calculated to the accuracy of the estimated MR signals or to reduce the error between the measured MR signals and the estimated MR signals. For example, the voxels may be represented as a graph. As described further below with reference to FIG. 7, this may facilitate auto-segmentation and/or registration. The spatial resolution in the MR model may be higher than is typically used for or associated with the strength of the external magnetic field (i.e., super resolution). In an exemplary embodiment, there are 512×512 voxels or 1024×1024 voxels at a magnetic-field strength of 3 T. Note that the voxel size may be less than $0.25^3$ mm$^3$.

In order to speed up the determination of the parameters in the characterization technique, compressed sensing may be used. For example, regions with air may be dropped. Moreover, because there may be more equations than unknowns, a down-selection technique may be used during the analysis. For example, linearly independent rows in a system of equations may be selected. Alternatively or additionally, the down selection may be: random, a subset of the equations that are most orthogonal, a subset of the equations that linearly independent in a particular setting, a subset of the equations that maximize the volume (such as a submatrix with the largest determinant), etc.

As noted previously, the external magnetic field and/or the RF pulse sequence may be modified or changed during the MR measurements. In some embodiments, the 'excitation' may be chosen to minimize the error in the next iteration of the analysis. For example, the external magnetic field and/or the RF pulse sequence may be changed based on how well conditioned the Jacobian is.

Note that the inputs to and the outputs from the analysis in the characterization technique may be stored for future use. Note that the inputs may include information about the measurement device and how the measurements were performed. This may allow accuracy to be traded off with acquisition time. In addition, it may allow the analysis to be continued offline over long times.

Figure 6:
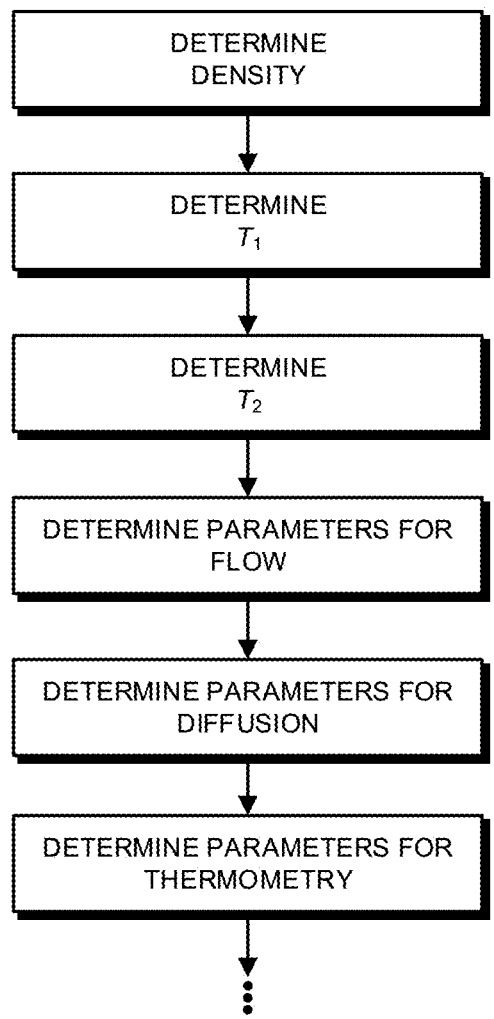
FIG. 6 is a drawing illustrating sequential determination of parameters having different associated time scales in accordance with an embodiment of the present disclosure.

Moreover, the parameters in the MR model may be determined sequentially based on the time scales associated with physical phenomena. This is shown in FIG. 6, which presents a drawing illustrating sequential determination of parameters having different associated time scales. In particular, temporal decomposition may allow the density to be determined, followed by $T_1$, $T_2$, parameters for flow, parameters for diffusion, parameters for thermometry, etc. This approach may be more efficient, because physical phenomena on longer time scales may require longer RF pulse sequences.

As noted previously, the characterization technique may not require the use of a Fourier transform or synchronous averaging. Instead, the parameters may be determined rapidly as long as the initial values of the parameters are reasonable (such as within 25, 50, 100, 500 or 1000% of the correct parameter values). Alternatively or additionally, a longer RF pulse sequence may be used.

Figure 7:
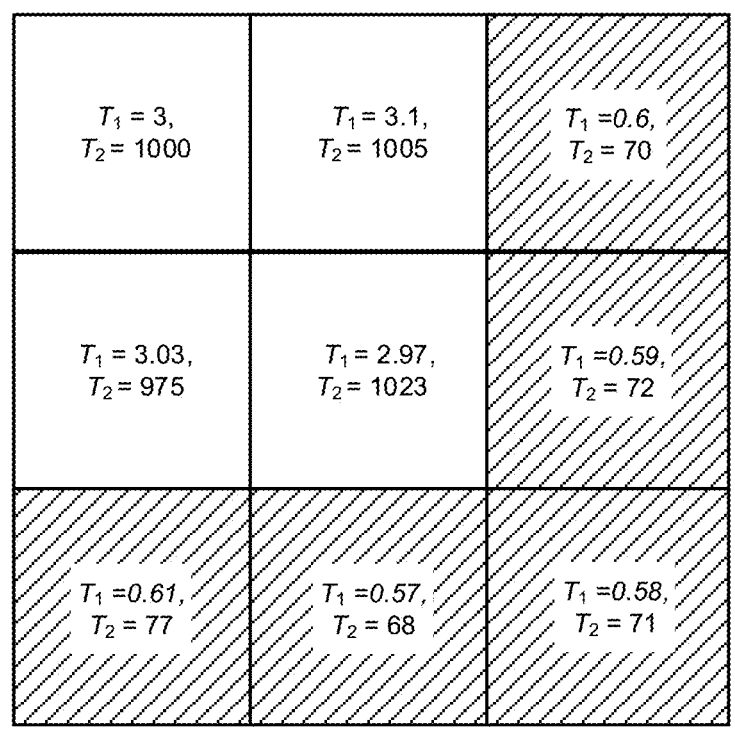
FIG. 7 is a drawing illustrating segmentation of tissue types in a sample in accordance with an embodiment of the present disclosure.

Furthermore, the variation in the parameters in different types of tissue may allow the types of tissue to be segmented. In particular, at a spatial boundary of two types of tissue there may be a discontinuity in a dimension in a high-dimensional space of the parameters. This is shown in FIG. 7, which presents a drawing illustrating segmentation of tissue types in a sample, such as distinguishing cerebrospinal fluid from the meninges (which is illustrated using cross-hatched boxes). As noted previously, the variation in the parameters for different types of tissue may be used to constrain the search space when solving the inverse problem.

We now describe embodiments of a technique for segmenting different types of tissue. Define a dictionary $D_{mr}$ of measured time sampled MR trajectories (or vectors) in a multi-dimensional parameter space for different types of tissue dj (for j=1 to n) such that a measured MR signal $y_{obv}$ for a voxel can be expressed as $$y_{obv} = \sum_{j=1}^{n} \alpha_j \cdot d_j + \varepsilon,$$

where $\alpha_j$ are normalized weights $$\left(\text{i.e., } \sum_{j=1}^{n} \alpha_j = 1\right)$$

and $\varepsilon$ is an error (i.e., $\varepsilon=(y_j, \alpha_j)$, for j=1 to n. This may define an intra-voxel linear equation problem. A generalized inter-voxel problem may model a set of voxels (such as a cube with 27 voxels) as a graph G. Note that each voxel in the set may have 26 edges to eight adjacent voxels. A parameter solution to the inverse problem may be defined as one that minimizes the error.

Consider the case of two adjacent voxels u and v. The intra-voxel linear equations $U_y$ and $V_y$ need to be solved at both u and v. There are several possible outcomes. First, $U_y$ and $V_y$ may have unique parameter solutions (where a 'unique parameter solution' may be a best fit to an existing MR model, i.e., with an error or difference vector that is less than a convergence criterion) and the analysis may be finished. Alternatively, $U_y$ may have a unique parameter solution but not $V_y$. It may be possible that the parameter solution for $U_y$ imposes a constraint on $V_y$ such that $V_y$ has a single parameter solution, in which case the analysis may be finished. However, neither $U_y$ and $V_y$ may have unique parameter solutions, in which case combining the systems of equations (i.e., effectively increasing the voxel size) may yield a unique parameter solution. Moreover, neither $U_y$ and $V_y$ may have any parameter solutions, in which case the intra-voxel problem cannot be solved without further constraints.

In the last case, it may be possible to look at an adjacent voxel w, i.e., series voxels u, v and w, with the corresponding intra-voxel linear equations $U_y$, $V_y$ and $W_y$ need to be solved at u, v and w. Note that the intra-voxel linear equations $V_y$ and $W_y$ reduce to the previous case. When the intra-voxel linear equations do not reduce to the previous case, this paring operation can be applied recursively until it does and then the intra-voxel linear equations can be solved as described previously.

In general, this computational technique may be isomorphic to the problem of fitting a 3D surface (or volume) to minimize the error. One challenge in this regard is that it assumes that all adjacent volumes have an equal effect on the parameter solution $\alpha_j$ that minimizes the error.

The minimization of the error may initially assume that there is no inter-voxel contribution (i.e., that the voxels are independent). Subsequently, inter-voxel contributions may be included. In particular, considering adjacent voxel volumes, there are two distinct classes. Volumes that share a surface and volumes that only share a 1D edge. The minimization function can be improved by weighting the error contribution at voxel u at the center of the relative coordinate system. If the effect on the error is proportional to $r^{-2}$ (where r is the distance between center points of voxels) and assuming 1 mm isotropic voxels in the weightings, the minimization or fitting problem with inter-voxel contributions can be expressed as $$\min(\text{error}(y(0, 0, 0), \alpha(0, 0, 0) + \frac{1}{(1)^2}\sum_{k=1}^{m}\text{error}(y_k, \alpha_k) + \frac{1}{(\sqrt{2})^2}\sum_{l=1}^{p}\text{error}(y_l, \alpha_l),$$

where the summation over k is for adjacent voxels sharing a common surface (i.e., (−1,0,0), (1,0,0), (0,−1,0), (0,1,0), (0,0,−1) and (0,0,1)) and the summation over l is for a remainder of adjacent voxels sharing a common edge. The assumption in the analysis is that the most difficult place to fit or determine parameter solutions is at discontinuities or interfaces between different tissues. Consequently, during the characterization technique, computer system 114 (FIG. 1) may solve these locations first and then may solve the remaining locations.

Alternatively, because the magnetic contribution from neighboring voxels is proportional to $r^2$, given a sphere of radius R from the center of a primary or central voxel in the minimization problem, surrounding voxels may be weighted based on the how much the sphere expands into the volume of the adjacent voxels (and, thus, based on how strong their inter-voxel contribution is estimated to be). For example, there may be three different weights that need to be assigned, including: a weight for voxels that share a 2D surface, a weight for voxels that share a 1D line, and a weight for voxels that share a 0D point. Because there may not be a uniform tissue distribution within each voxel, the weights may be dynamically adjusted to model different kinds of distributions inside each voxel in order find the distributions that minimize the error. This may provide the ability to identify multiple MR signatures within a single voxel for different types of tissue. Note that, as computational power increases, the accuracy of the predictive model may increase and the computational technique used to solve the minimization problem (and, thus, the inverse problem) may be modified.

Thus, in embodiments where the invariant MR signature or MR model of a voxel depends on the invariant MR signatures or MR models of surrounding or neighboring voxels, the invariant MR signature or MR model of a voxel may be computed using $2^{nd}$ or $N^{th}$-order effects. For example, if there are N $1^{st}$-order invariant MR signatures or MR models (where N is an integer), there may be as many as $N!/(N-27)!$ $2^{nd}$-order invariant MR signatures or MR models (if all the voxels interact with each other). In some embodiments, locality is used to simplify the inverse problem. In this way, an invariant MR signature or MR model may be generated by incorporating how the invariant MR signatures or MR model in adjacent voxels effect the invariant MR signature or MR model in a primary (central) or $1^{st}$-order voxel.

In some embodiments, a dithering technique is used to overcome the arbitrary locations of the voxels relative to the distribution of types of tissue in the body. In particular, there may be two or more types of tissue in a voxel because of the arbitrary voxel placement or the current voxel size. This may significantly change the MR model parameters for this voxel. This may suggest that there is more than one invariant MR signature or MR model needed for the voxel. In order to confirm this, the voxels may be displaced by a distance dx (which is a fraction of the voxel length, width or height) and the MR model parameters may be determined again. In the processes, the tissue distribution may be determined. Consequently, this approach may effectively increase the spatial resolution in the analysis without changing the voxel size.

While the preceding discussion used the Bloch equations as an illustrative example of the MR model, in other embodiments full Liouvillian computations (such as a Liouville supermatrix of interactions between two or more elements) or another simulation technique are used. Note that the MR signals computed or predicted using the MR model may be sampled at a rate equal to or higher than twice the Nyquist frequency of MR signals acquired during an MR scan.

In some embodiments, the assumptions underlying the Bloch equations are invalid. In particular, in the rotating frame with an RF pulse (even an infinitesimally short RF pulse), the parallel and antiparallel components of the magnetization are coupled. If the state is reset before each RF pulse sequence, this effect is secondary. However, when the state is dynamically varied, such as allowed by the characterization technique, error terms may need to be added to the Bloch equations. This insight allows the characterization technique to be used with rapid variations (on/off) in the RF pulse sequences and/or the acquisition of data between RF pulses.

In some embodiments, the tensor field mapping in the characterization technique uses one or more forward models (such as the MR model) and one or more inverse solvers. As noted previously, the tensor field mapping (the determination of the forward model parameters in the sample) may not require any precomputation or training. Moreover, the tensor field mapping may solve the generalized reconstruction problem without any assumption about the measurement device or hardware, such as the use of a Fourier transform (e.g., a fast Fourier transform). Thus, the tensor field mapping may not require any specific measurement hardware. Instead, the parameters that specify the hardware just may be incorporated into the forward model.

The use of the forward model may also provide additional degrees of freedom in the measurements. For example, in the case of an MR technique, linear magnetic-field gradients and/or a homogenous magnetic field may not be required. This means that, in principle, at least some of the voxels can have slightly different dimensions. Indeed, the tensor field mapping may eliminate the need for a separate magnetic-field gradient system, which is typically required for MRI.

Figure 10:
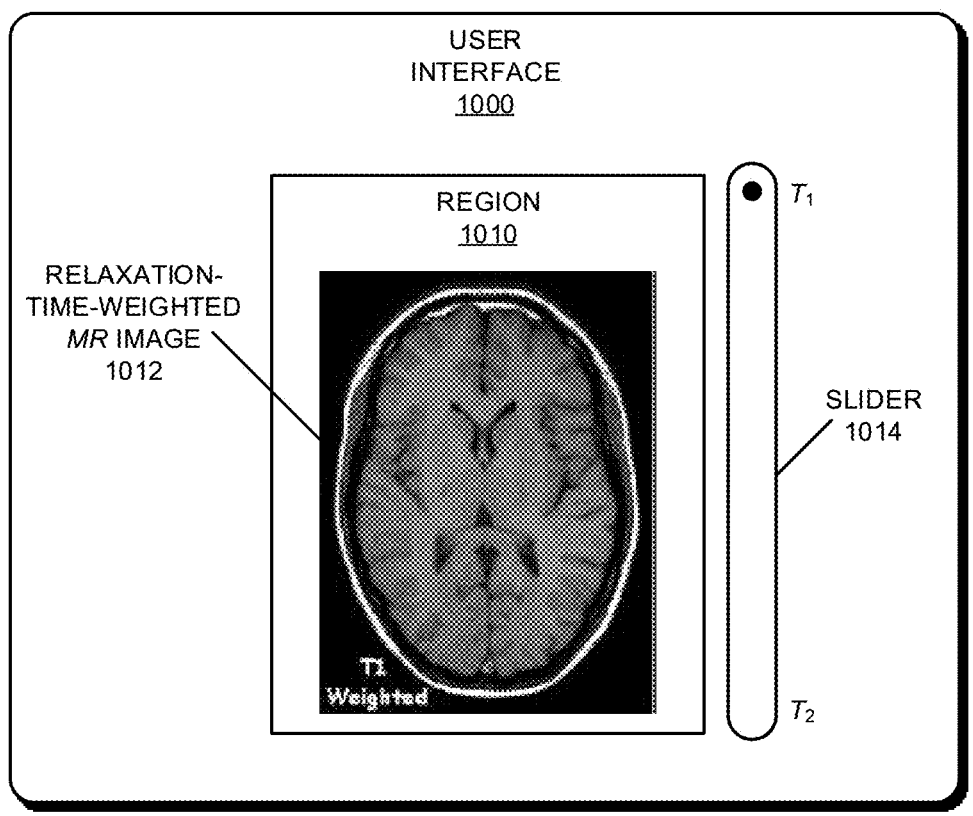
FIG. 10 is a drawing illustrating a graphical user interface in accordance with an embodiment of the present disclosure.
Figure 11:
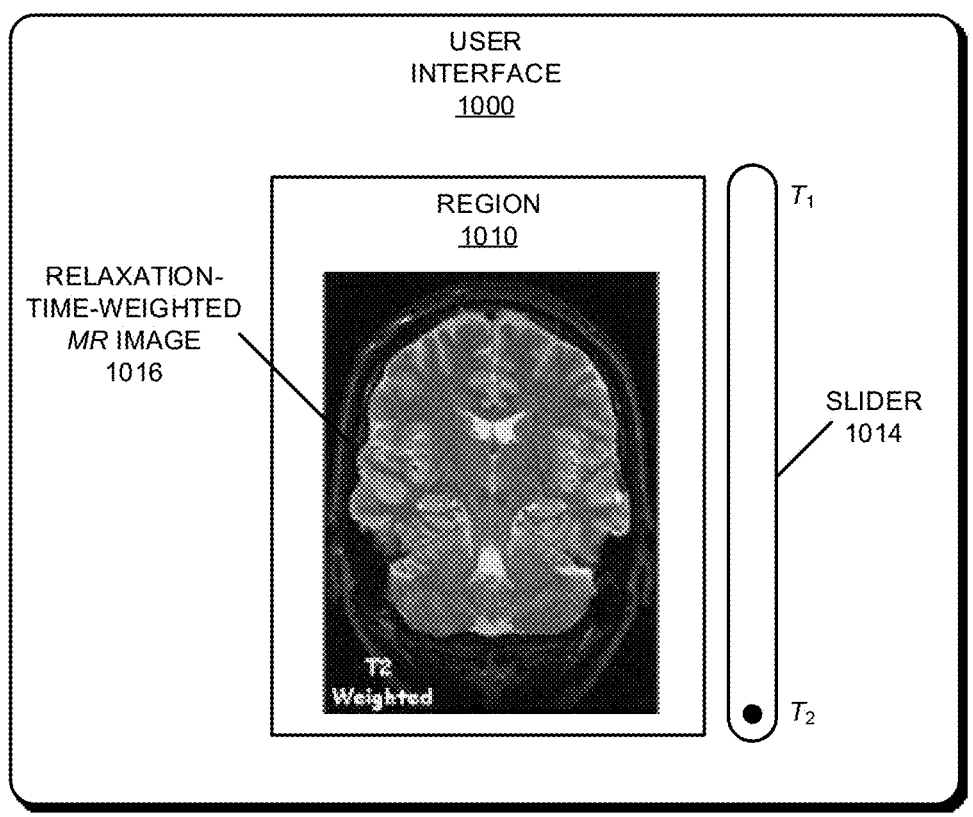
FIG. 11 is a drawing illustrating a graphical user interface in accordance with an embodiment of the present disclosure.

The tensor field mapping may allow parameters, such as $T_1$ and $T_2$, to be characterized more rapidly than existing MR techniques. Furthermore, the use of tensor field mapping may extend or generalize the meaning of the relaxation parameters. For example, the characterization technique may provide allow dynamic modulation to extract more information about a sample. For example, in materials that are anisotropic, it may be useful to measure $T_1$ with many different polarizing external magnetic fields because it can provide more information about the material. In particular, a rigid material (such as bone) may be anisotropic, while fluids are often isotropic because the molecules tend to align with the polarizing external magnetic field. The constant polarizing external magnetic field in MRI may be well suited for characterizing isotropic materials, such as water. However, with anisotropic materials proper characterization may involve a range of external magnetic-field directions, with corresponding relaxation parameters associated with each direction. The full wealth of this information may be available via the tensor field mapping. In some embodiments, as shown in FIGS. 10 and 11, the higher dimensional information can be projected into 2D images that correspond to a fixed external magnetic-field direction, as is the case with MM. Nonetheless, the tensor field mapping may provide richer, higher-dimensional and more general relaxation parameters.

Note that with tensor field mapping signal averaging or repeated measurements may not be needed. Thus, there may not be a need to reset the polarization of the state of the sample, repeat the RF pulse sequence and average the measurements in order to boost the signal-to\-noise ratio.

Moreover, the tensor field mapping may allow an arbitrary number of isochromes (spins at locations in space) to be simulated per 'voxel.' Indeed, the tensor field mapping may allow the isochromes to be simulated or determined in space that is higher resolution than any voxel. Subsequently, after solving the problem, the information from the higher dimensional parameter space can be projected to arbitrary voxel boundaries (or an arbitrary grid of voxels) to determine the parameters of a voxel. In this way, the parameters in the tensor field mapping can be used to determine parameter values in a range of voxel sizes that are determined or specified afterwards.

Furthermore, the tensor field mapping may benefit from every 'experiment' or measurement being different or changed, because new information can be extracted that further constrains the solutions to the high-dimensional parameter space. Consequently, the tensor field mapping may benefit from real-time measurements and simulations (e.g., the simulations may be performed in the same time as the RF pulse sequence, thus, the simulations may be performed in 300 ms for a 300 ms RF pulse sequence). In particular, by performing real-time simulations, the excitation in the measurements can be changed to fill in sparse portions of the parameter space in order to reduce the residual error between the measurements and the estimated response, thereby allowing the tensor field mapping to converge more rapidly. In some embodiments, an optimal RF pulse sequence with one or more RF pules can be selected in order to minimize the error on the next iteration.

Thus, because the tensor field mapping can be performed rapidly, the sample can be continuously excited and the parameters in the forward model can be continuously determined. This means that new information can be obtained with every RF pulse. Moreover, this capability allows iterative improvement in the quantitative accuracy in real-time until a condition (such as a residual error or a convergence criterion) is met. In contrast, approaches that may attempt to determine the parameters using post-processing may either have to contend with missing information that is needed to solve the problem or may need to re-scan the sample, as opposed to the capability in the characterization technique to gather the additional or missing information in real time. As noted previously, the additional or missing information that is acquired in real time may include information about a specific region of the volume that is obtained by changing the spatial resolution or the set of measurements.

The characterization technique may allow real-time video of phenomena that are occurring inside of the sample. For example, the characterization technique may be used to record a physiological process in real time. Thus, instead of acquiring a scan unto a minimum error is reached, the characterization technique may be used to 'record' something happening inside the body, such as watching the temperature of water that was ingested diffuse into a patient's stomach.

Note that the fast or real-time convergence during the characterization technique may make it more resilient to random noise spikes or errors in the measurement device (such as an MR scanner) because it iteratively and dynamically converges the measurements and simulations in real time. Moreover, the real-time measurement/simulation capability in the characterization technique may eliminate the need to reset the sample state between measurements. Instead, the dynamic state may be tracked and used in subsequent simulations or estimations of the sample response as the tensor field map is generated.

The tensor field mapping may not be limited to RF pulses. As noted previously, a wide variety of excitation may be used to 'excite' a region of space as long as there is a forward model that describes those excitations and there are sensors that can measure the response of a volume of space in the sample. For example, in some embodiments mechanical excitations may be used. This may involve the use of ultrasonic waves or actually 'touching' an object. Moreover, the excitations may include constructive/destructive interference of an infrared laser to heat up a region of space and see how the region responds. In general, there will be spatial differences because different types of material have different thermodynamic properties and may absorb and emit heat at different rates. In some embodiments, the excitation may include an electron beam.

As noted previously, the inputs to the forward model may include information specifying the hardware and/or the software during the measurements and the simulations using the forward model. The software inputs may include: one or more forward models that describe the relationships between the sample state, the excitation and the sample response; one or more inverse solvers; an excitation selector that chooses the next set of excitations to apply to a volume of space in a sample in order to optimize an objective function (such as reducing the error or difference between the measurements and the simulations); parameters that define the sample response; an application-programming interface that can be used to specify the excitations; and/or an application-programming interface to control/read information back from sensors in the measurement device. Moreover, the hardware inputs may include: generators that generator the excitations or different ways of depositing or transferring energy into a volume of space in the sample; generating sensors that measure that output of the generating devices that generate the excitations; and/or measurement sensors that measure the response of the volume of space in the sample that is being scanned.

Note that the outputs from the characterization technique may include a set of raw time series signals gathered from the sample measurement sensors during a scan (which can be used to generate a temporal series or stream of tensor field maps). The sample measurement sensors may include an arbitrary number of different types of sensors that perform measurements about the volume of space being scanned. In addition, the outputs may include information about the measurement device (such as the MR scanner) that includes physical properties, parameters, and measurements taken about the measurement device as well as its performance during a scan. Moreover, another output from the characterization technique may include a so-called quantitative space or Q-space, i.e., a time series of tensor field maps. These tensor field maps may be reconstructed from the inverse solver(s). The tensor field maps may be thought of as a data stream with 3 spatial×one temporal×N measurement dimensions, where each measurement may be a vector or scalar quantity. For example, temperature is a scalar quantity, while flow is a vector quantity. Note that the spatial resolution in a tensor field map is arbitrary and may not need to be evenly or uniformly distributed in space. Thus, the spatial sampling can be higher density in some regions than others. Furthermore, another output from the characterization technique may include a physical forward model of the volume of space in the sample that is being scanned and that can be reconstructed from one or more of the series of tensor field maps that were generated. Using the forward model, the way that the volume of space will respond to an arbitrary excitation can be determined. For example, if a human is scanned, a forward MR model may be used to subsequently predict how this human's body will respond to an arbitrary external magnetic field and/or an arbitrary RF pulse sequence. While the tensor field maps and/or the forward model can be recomputed an arbitrary number of times after a scan has been completed to generate higher quality results (such as the forward models, the inverse solvers get better over time and as the cost of computation continues to fall), as noted previously there are significant advantages to performing the tensor field mapping and dynamically adjusting the measurements in real time.

In some embodiments, computational geometry engine may be used to fit surfaces in the parameter space in order to help the inverse solvers minimize the error by finding the boundaries of tissue. Moreover, an anatomical model of male or female anatomy may be used to accelerate the determination of the tensor field map and the convergence of the parameters with the measurements. Furthermore, historical information about the sample (such as previous outputs of the tensor field mapping) may be used to help select initial values of the sample and/or the anatomical model in order to more quickly converge on solutions. In this way, the subsequent tensor field mapping can be performed differentially relative to the previous outputs of the tensor field mapping. Additionally, the tensor field mapping may use a diagnostic platform that integrates or uses a data structure of medical knowledge, known tissue signatures, one or more individual's medical histories (such as genetic, epigenetic, information about the transcriptome, information about the proteome, information about the metabolome, information about the microbiome, etc.).

In addition to not requiring specialized hardware, as noted previously the characterization technique may not require previous training or information in order quantify tissue parameters or automatically segment tissues/structures. Moreover, the characterization technique may not rely on a non-deterministic, statistical, or pattern-matching technique. The characterization technique may use equations that represent the physics that govern the measurement device and the volume of space in the sample that it scans. So long as the physics is not changing during the scan of the volume, the characterization technique may be used to rapidly determine the tensor field maps.

In some embodiments, the characterization technique can make decisions not to do something based on the confidence of the measurements it has made and the forward model of the volume of space in the sample that was generated. Thus, using the characterization technique, computer system 120 in FIG. 1 can introspect itself and the outputs it generates. For example, computer system 120 may terminate an MR scan as being inconclusive because it failed to converge after a certain amount of time.

Alternatively or additionally, computer system 120 may integrate or include therapeutic techniques. In particular, suppose the MR scanner integrates or communicates with one or more proton beam generators, so that it is able to ablate malignant tissue as it was detected. Moreover, assume that the MR scanner has a way to ablate tissue in a 3D space without damaging surrounding tissue using constructive/destructive interference from the proton beams. Using the characterization technique, computer system 120 may decide, after N iterations, N seconds and/or a combination of factors of generating tensor field maps, that it is unable to generate a physical forward model of the volume of space in the sample being scanned within an acceptable precision/error (such as in terms of the properties of tissue, its physical dimensions and location in space, etc.). Consequently, computer system 120 may determine that it is too risky to try and ablate the tissue in question and, therefore, may include in the output of the scan information that indicates that it found tissue it wanted to ablate but the confidence was not high enough to do so in a safe manner.

The characterization technique may also have advantages over neural networks. Existing neural networks are generalized function approximators. For example, techniques such as deep learning typically use previous examples as inputs. In general, it is not possible for these machine-learning models to determine the actual function they are trying to approximate because there is no reference point for them to use to estimate the error in their predictions. In particular, it can be difficult for a neural network to make predictions based on an input that is very different from the examples it was trained on. In this regard, a neural network can be thought of as a lossy compute compression engine. In contrast, the forward model in the characterization technique is based on the physics. Consequently, in the characterization technique the functions are known, so the response can be computed using the functions as opposed to using an approximation, and thus the characterization technique can be used to determine when its predictions are unreliable.

However, because neural networks are effective approximations/compressions of the actual computation, they may execute faster on the same input with less computational power required, at the expense or risk of not being able to reliably identify situations where the accuracy of the output (such as the predictions or simulations) is degraded. Therefore, in some embodiments the characterization technique is combined with one or more neural networks. Because a neural network is an approximation, and it will likely execute faster than a full simulation, it may be beneficial to run both in parallel so that the first-order approximation is given by the neural network. Then, two inverse solvers may be run in parallel. One may be based on a neural network and the other may involve a brute-force calculation. The difference between the two inverse solvers may be the error in the neural-network-based approach. This approach may allow the neural network to learn because the pure simulation and numerical approach may be able to give real-time feedback to the neural network and to back propagate/update the weights in the neural network. This hybrid approach would still not require or need a priori training, but would be able to leverage the pattern-matching benefits of large neural networks with the determinism and accuracy of simulation/numerical techniques in the characterization technique. The hybrid approach may assist the neural network when it has an input unlike any of the examples used to train it. Similarly, the hybrid approach may be used to go directly from time-domain measurement to the quantized/parameterized output (i.e. the inverse problem outputs).

Figure 8:
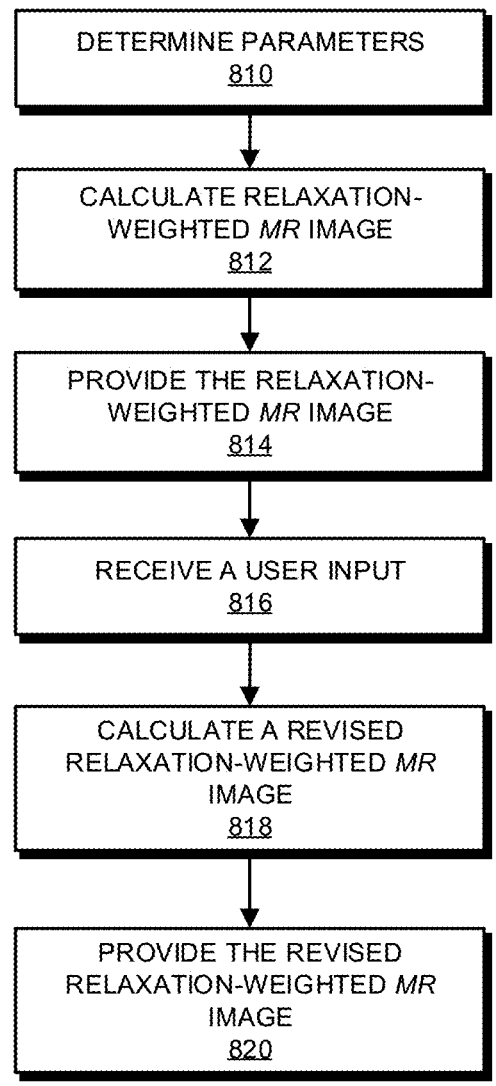
FIG. 8 is a flow diagram illustrating a method for providing a dynamic relaxation-time-weighted MR image in accordance with an embodiment of the present disclosure.

We now describe other embodiments of the characterization technique. Because the characterization technique allows estimated MR signals to be generated based on the parameters in the MR model, a range of weighted MR images may be generated based on a user or operator's instructions. For example, the $T_1$ or $T_2$-weighting (or flare) in MR images may be dynamically varied based on user instructions. This is shown in FIG. 8, which presents a flow diagram illustrating a method 800 for providing a dynamic relaxation-time-weighted MR image, which may be performed by a system (such as system 100 in FIG. 1). During operation, the system may determine parameters (operation 810) in a forward model of a magnetic response of a sample based on measurements of a MR signal associated with the sample while an external magnetic field and an RF pulse sequence are applied to the sample.

Then, the system may calculate a relaxation-time-weighted MR image (operation 812) based on the measurements, the parameters, the forward model and a ratio of a longitudinal relaxation time along a direction parallel to the external magnetic field and a transverse relaxation time along a direction perpendicular to the external magnetic field.

Moreover, the system may provide the relaxation-time-weighted MR image (operation 814).

Subsequently, the system may receive a user input (operation 816) that specifies an update to the ratio. For example, the user may adjust one or more virtual sliders in a user interface displayed on a touch-sensitive display that specifies $T_1$, $T_2$ or the ratio.

Furthermore, the system may calculate a revised relaxation-time-weighted MR image (operation 818) based on the measurements, the parameters, the forward model and the updated ratio.

Next, the system may provide the revised relaxation-time-weighted MR image (operation 820).

Note that 'image' in method 800 is not restricted to a 2D representation of information. In particular, in embodiments where the external magnetic-field direction is varied during the measurements, the determined parameters may include information with respect to multiple different axes or directions (and, more generally, basis vectors). Consequently, the parameters in the MR model may include 3D information about different properties of the sample with respect to many different basis vectors. Therefore, in some embodiments, 'image' should be understood to include 3D or a higher dimensional representation of the acquired information.

Figure 9:
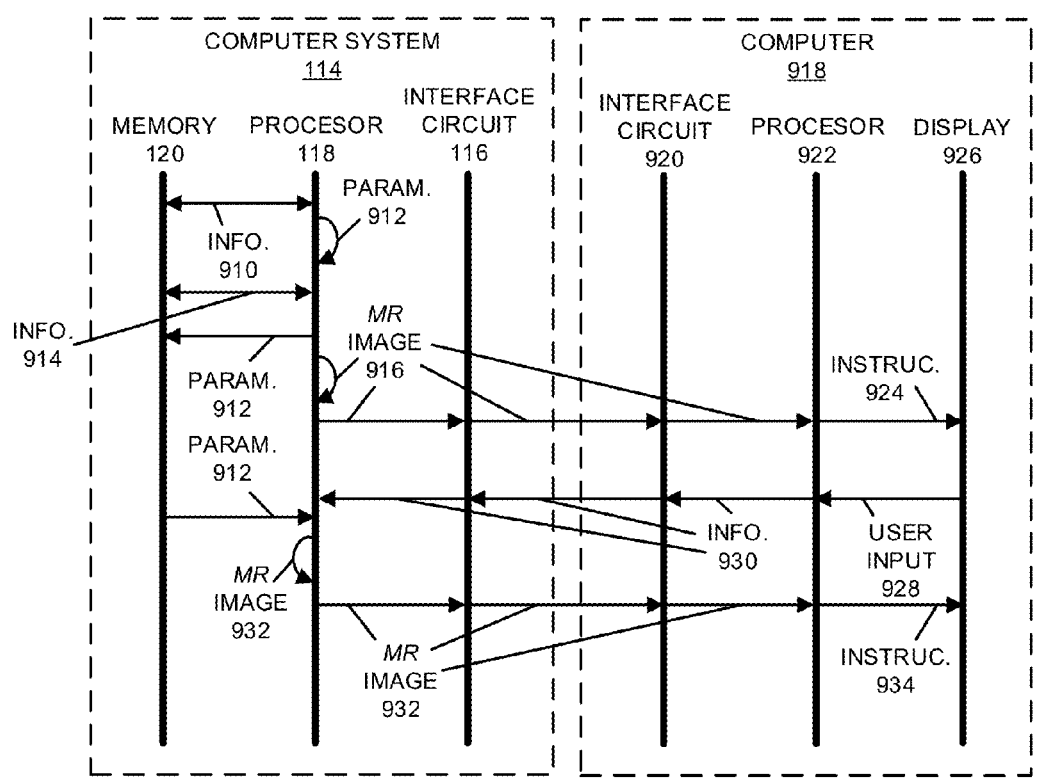
FIG. 9 is a drawing illustrating communication among components in the system in FIG. 1 in accordance with an embodiment of the present disclosure.

FIG. 9 presents a drawing illustrating communication among components in system 100 in FIG. 1. In particular, processor 118 in computer system 114 may access information 910 in memory 120, such as measured MR signals for a sample. Using this information, processor 118 may analyze information 910 to determine parameters 912, such as $T_1$ or $T_2$. This analysis may involve: registration, alignment, segmentation, determination of parameters in an MR model, simulation or estimation of MR signals using the MR model, and/or comparison of the measured MR signals with one or more templates. During the analysis, processor 118 may access additional information 914 in memory 120. Processor 118 may also store parameters 912 in memory 120.

Then, processor 118 may calculate a relaxation-time-weighted MR image 916 based on the MR signals, parameters 912, the forward MR model and a ratio of $T_1$ to $T_2$ (or $T_2$ to $T_1$). Moreover, processor 118 may instruct interface circuit 116 to provide relaxation-time-weighted MR image 916 to computer 918, which may be used by a radiologist.

After receiving relaxation-time-weighted MR image 916, interface circuit 920 in computer 918 may provide relaxation-time-weighted MR image 916 to processor 922. Furthermore, processor 922 may provide instructions 924 to display 926 to display relaxation-time-weighted MR image 916.

Next, processor 922 may receive user input 928. For example, display 926 may be a touch-sensitive display, and user input 928 may be based on user interaction with a user interface (with virtual icons) displayed on display 926. Alternatively or additionally, user input 928 may be provided by the user using a physical user-interface device, such as a keyboard, a mouse, etc. User input 928 may specify $T_1$, $T_2$ and/or an update to the ratio of $T_1$ and $T_2$ (or $T_2$ to $T_1$).

In response, processor 922 may instruct interface circuit 920 to provide information 930 that specifies the updated ratio of $T_1$ and $T_2$ to computer system 114. After receiving information 930, interface circuit 116 may provide the updated ratio of $T_1$ and $T_2$ to processor 118, and processor 118 may calculate a revised relaxation-time-weighted MR image 932 based on the MR signals, parameters 912, the forward MR model and the updated ratio of $T_1$ to $T_2$. Moreover, processor 118 may instruct interface circuit 116 to provide relaxation-time-weighted MR image 932 to computer 918.

After receiving relaxation-time-weighted MR image 932, interface circuit 920 in computer 918 may provide relaxation-time-weighted MR image 932 to processor 922. Furthermore, processor 922 may provide instructions 934 to display 926 to display relaxation-time-weighted MR image 932.

In contrast with existing approaches to MRI or MRSI that usually provide qualitative or 'weighted' measurements of a limited set of properties, the characterization technique may facilitate richer and more dynamic quantitative information about a sample. For example, as shown in FIG. 10, which presents a drawing illustrating a graphical user interface 1000, a region 1010 may present or display relaxation-time-weighted magnetic-resonance image 1012. This relaxation-time-weighted magnetic-resonance image may correspond to measurements of an MR signal associated with the sample while an external magnetic field and an RF pulse sequence are applied to the sample, parameters in a forward model of a magnetic response of the sample, the forward model and a ratio of $T_1$ and $T_2$ (or $T_2$ to $T_1$). In some embodiments, $T_2^*$ is used instead of $T_2$ when generating the relaxation-time-weighted magnetic-resonance image.

Moreover, graphical user interface 1000 may include one or more virtual icons (such as slider 1014) that allow a user to modify or update the ratio of $T_1$ and $T_2$. As shown in FIG. 11, which presents a drawing illustrating a graphical user interface 1100, in response to a user modification of the ratio of $T_1$ and $T_2$ using virtual icon 1014 (such as by sliding the slider to a new position), region 1010 may display a revised relaxation-time-weighted MR image 1016, revised relaxation-time-weighted MR image 1016 corresponding to measurements of the MR signal, the parameters, the forward model and the modified ratio of $T_1$ and $T_2$. Thus, the characterization technique may be used to generate and/or present dynamically adjustable $T_1$ and/or $T_2$-weighted images.

Figure 12:
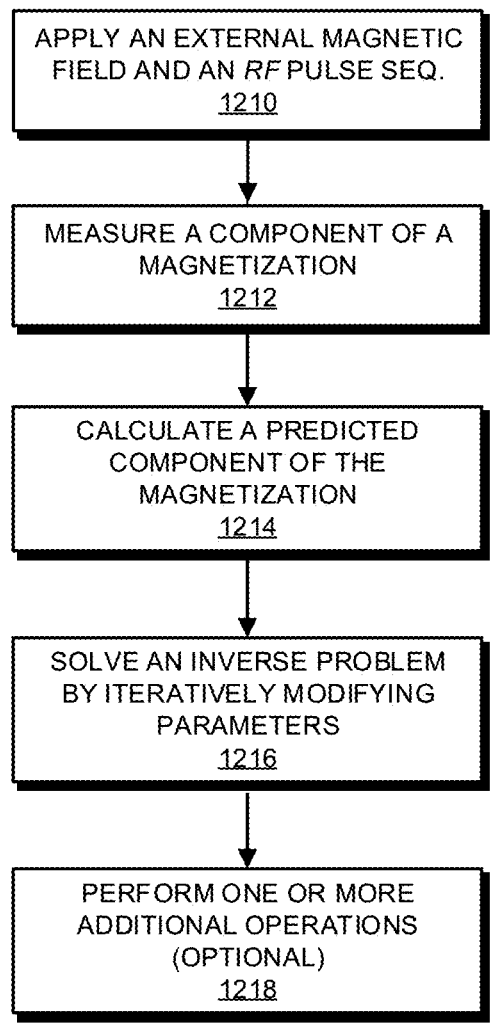
FIG. 12 is a flow diagram illustrating a method for determining parameters associated with a sample in accordance with an embodiment of the present disclosure.

We now describe a more generalized version of the characterization technique and method 300 (FIG. 3). FIG. 12 presents a flow diagram illustrating a method 1200 for determining parameters associated with a sample, which may be performed by a system (such as system 100 in FIG.

1). During operation, the system may apply an external magnetic field and an RF pulse sequence (operation 1210) to the sample.

Then, the system may measure at least a component of a magnetization (operation 1212) associated with the sample.

Moreover, the system may calculate at least a predicted or estimated component of the magnetization (operation 1214) for voxels associated with the sample based on the measured component of the magnetization, a forward model, the external magnetic field and the RF pulse sequence.

Next, the system may solve an inverse problem by iteratively modifying the parameters (operation 1216) associated with the voxels in the forward model until a difference between the predicted component of the magnetization and the measured component of the magnetization is less than a predefined value. Note that the parameters may include a density of a type of nuclei, a longitudinal relaxation time along a direction parallel to the external magnetic field (such as $T_1$) and a transverse relaxation time along a direction perpendicular to the external magnetic field (such as $T_2$ or $T_2^*$).

Moreover, the iterative modification may be based on a Jacobian matrix using Newton's method. Furthermore, the iterative modifications may be constrained based on parameters determined using previous measurements of at least the component of the magnetization. Alternatively or additionally, initial values of the parameters may be within predefined parameter ranges for different types of tissue in the sample.

In some embodiments, the system optionally performs one or more additional operations (operation 1218). For example, the system may segment tissue types in the sample based on discontinuous changes in at least some of the parameters along a direction between the voxels. Moreover, the parameters may be determined without performing a Fourier transform on the measured component of the magnetization. Furthermore, the calculation of the component of the magnetization and the iterative modifications may be performed concurrently with the measurement of the component of the magnetization.

Additionally, the system may change at least one of a magnitude and a direction of the external magnetic field as a function of time during the measurement. For example, the system may: modify at least one of the external magnetic field and the RF pulse sequence; apply at least the one of the modified external magnetic field and the RF pulse sequence to the sample before the sample has completely relaxed or without resetting a state of the sample; measure at least a second instance of the component of the magnetization; calculates at least a second instance of the predicted component of the magnetization for the voxels associated with the sample based on the measured second instance of the component of the magnetization, the forward model, the modified external magnetic field or the modified RF pulse sequence; and solve the inverse problem by iteratively modifying the parameters associated with the voxels in the forward model until a difference between the second instance of the predicted component of the magnetization and the second instance of the measured component of the magnetization is less than the predefined value. Moreover, the system may determine a dynamic state of the sample based on the forward model, the external magnetic field and the RF pulse sequence, where the dynamic state when at least one of the modified external magnetic field and the modified RF pulse sequence is applied to the sample may be used as an initial condition when calculating the second instance of the predicted component of the magnetization.

Thus, the characterization technique may allow continuous measurement and modification of the parameters. Note that at least one of the modified external magnetic field and the modified RF pulse sequence may be selected to minimize the difference between the second instance of the predicted component of the magnetization and the second instance of the measured component of the magnetization.

Furthermore, as described previously with reference to FIG. 6, the parameters may be determined sequentially based on time scales associated with the parameters, and a parameter that has a shortest time scale may be determined first.

In some embodiments of method 300 (FIG. 3), 800 (FIG. 8) and/or 1200 (FIG. 12), there may be additional or fewer operations. Furthermore, the order of the operations may be changed, and/or two or more operations may be combined into a single operation.

Figure 13:
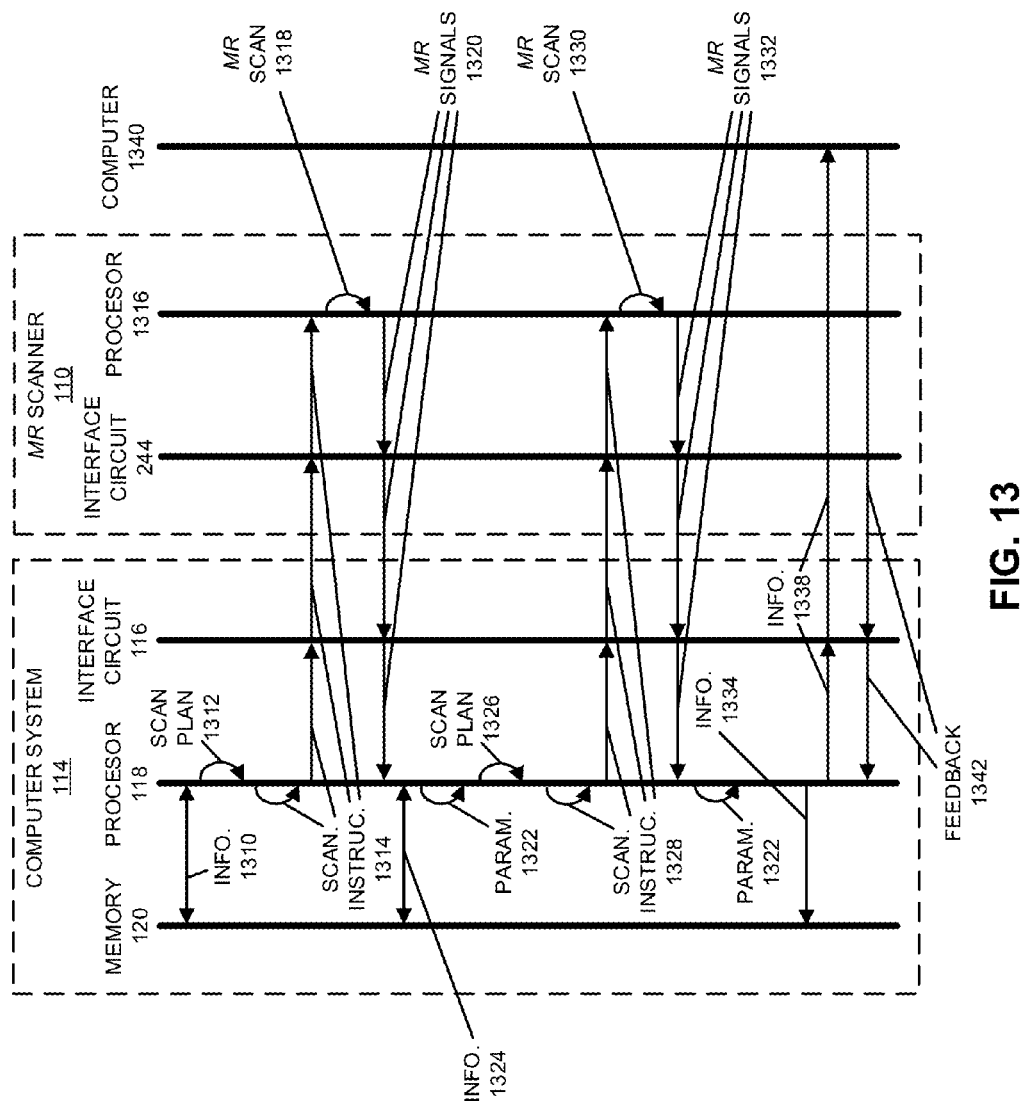
FIG. 13 is a drawing illustrating communication among components in the system in FIG. 1 in accordance with an embodiment of the present disclosure.

FIG. 13 presents a drawing illustrating communication among components in system 100 in FIG. 1. In particular, processor 118 in computer system 114 may access information 1310 in memory 120. Using this information, processor 118 may determine a scan plan 1312 and scanning instructions 1314. Then, processor 118 may provide, via interface circuit 116, scanning instructions 1314 to MR scanner 110.

After interface circuit 244 receives scanning instructions 1314, processor 1316 may execute them, so that MR scanner 110 performs an initial MR scan 1318. During MR scan 1318, MR scanner 110 may apply an external magnetic field(s) and RF pulse sequences(s) to a sample based on scanning instructions 1314, and may acquire or capture MR signals 1320, which are provided to computer system 114.

Processor 118 may analyze MR signals 1320 to determine parameters 1322 in an MR model of the sample. During the analysis, processor 118 may calculate at least a predicted or estimated component of the magnetization for voxels associated with the sample based on MR signals 1320, a forward MR model, the external magnetic field and the RF pulse sequence. Moreover, during the analysis, processor 118 may access additional information 1324 in memory 120.

Based on residual differences between MR signals 1320 and the estimated MR signals, processor 118 may dynamically update scan plan 1326. Then, processor 118 may determine updated scanning instructions 1328, which are provided to MR scanner 110.

After MR scanner 110 receives scanning instructions 1328, processor 1316 may execute them, so that MR scanner 110 performs MR scan 1330. During MR scan 1330, MR scanner 110 may acquire or capture MR signals 1332, which are provided to computer system 114.

Note that processor 118 may repeat one or more of the aforementioned operations until the MR scan(s) of the individual are completed and/or a desired accuracy of one or more determined parameters 1322 is achieved. Thus, processor 118 may solve an inverse problem by iteratively modifying parameters 1322 associated with the voxels in the forward MR model until a difference between the predicted MR signals and the measured MR signals is less than a predefined value. Processor 118 may also store information 1334 (such as the MR signals, metadata and other related information) in memory 120.

In addition, computer system 114 may provide information 1336 about the MR scan(s) to a third party (such as a radiologist), such as to a computer 1338 associated with the third party. Subsequently, computer 1338 may provide feedback 1340 from the third party that is used to update the current scan plan, a future scan plan, a recommended future scan time, one or more templates, etc.

In an exemplary embodiment of the tensor field mapping, a polarizing field is optionally applied to a sample. Then, an excitation is applied to the sample. Note that the excitation field may be other than one or more RF pulses. Moreover, a response of the sample to the excitation is measured. In some embodiments, the signal inputs and outputs from the measurement device (such as RF pulses or magnetic-field inhomogeneity, information about the MR scanner, etc.) are also measured. Next, the response of the sample is simulated using a forward model. Furthermore, parameters in the forward model are iteratively modified based on differences between the measured response and the simulated or the predicted response of the sample.

Thus, by using one or more non-invasive imaging or measurement techniques, quantitative comparisons of non-invasive imaging or measurements and simulated or computed measurements may be used to iteratively update a predictive model with parameters that characterize or describe voxels in a sample.

While the preceding discussion illustrated the use of MR techniques in the characterization technique, this approach may be generalized to a measurement system that is able to physically model and measure a material in real-time using a wide variety of measurement techniques. In general, this measurement system can use a combination of mechanical and/or electromagnetic waves to 'perturb' or 'excite' the volume being scanned in order to evaluate the correctness of a prediction in terms of how the volume responds to the perturbation. This also includes the ability for the measurement system to simulate itself and any part of the environment in which the measurement system is located that could affect the correctness or accuracy of the predictive model the measurement system is trying to generate to describe the volume being scanned or measured.

Note that the different measurement techniques may provide tensor-field mapping and the ability to detect anomalies in tensor fields. These maps can be images or quantitative tensor field maps, and each of the measurements techniques may provide a visualization of a different type of tensor field map captured with a different measurement technique. By looking at or considering two or more of these maps, of the measurement system may have access to orthogonal information.

Thus, the measurement system may provide a way to capture, in real-time or near real-time, higher-order or hyper-dimensional pseudo or hybrid tensors or matrices at each voxel in 3D space. Using electromagnetic and/or mechanical perturbations or excitations, the measurement system may use different measurement techniques to measure disturbances and responses, and then to simulate the responses. Moreover, the measurement system may iterate this process based on differences between the measured and the simulated responses. For example, during the iteration, the sampling frequency, the measurement technique, etc. may be modified to determine additional information that is subsequently used to refine the simulations and to reduce the differences. Stated differently, the next perturbation or disturbance may be chosen to minimize the error of the difference across the hyper-dimensional space. Note that this adaptation or learning may be based on one or more supervised learning techniques (such as a deep-learning technique, a support vector machine, a classification and regression tree, logistic regression, linear regression, nonlinear regression, a neural network, pattern recognition, a Bayesian technique, etc.) and/or a non-deterministic approach (such as a heuristic).

Consequently, the hyper-dimensional matrices at the voxels may not have a fixed resolution and/or a fixed set of parameters. Instead, this information (such as a sparsity of the matrices) may vary based on the results of previous scans and/or a current scan. For example, coarse scans may be followed by fine-resolutions scans of particular regions or features that are of interest based on constraints, such as a prior knowledge (e.g., a medical history of one or more individuals, etc.).

The result of this characterization may be a (4+N)D (three spatial dimensions, one time dimension, and N measurement dimensions at each point in space) quantitative model of the volume being scanned. Thus, the characterization technique may involve MR techniques other than MRI or may include MM. Note that the (4+N)D quantitative model may be projected onto an arbitrary subset of the full (4+N)D space, including 2D or 3D images.

In some embodiments, the use of multidimensional data and models provides enhanced diagnostic accuracy (i.e., a lower false-positive rate) relative to conventional MRI approaches, even if a larger voxel size is used. Thus, the characterization technique may allow improved diagnostic accuracy with a larger voxel size than would be needed in conventional MM. However, as noted previously, the characterization technique may be used with a wide variety of measurement techniques in addition to MM.

Figure 14:
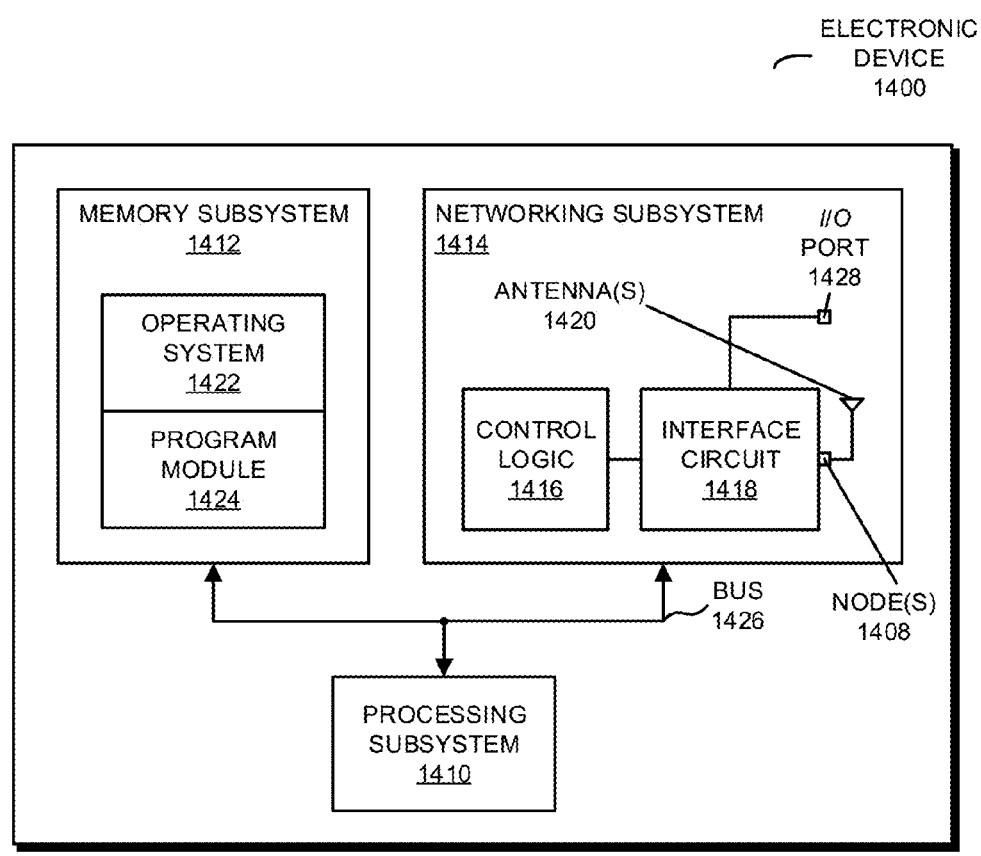
FIG. 14 is a block diagram illustrating an electronic device in accordance with an embodiment of the present disclosure.

We now further describe an electronic device that performs at least some of the operations in the characterization technique. FIG. 14 presents a block diagram illustrating an electronic device 1400 in system 100 (FIG. 1), such as computer system 114 (FIG. 1) or another of the computer-controlled components in system 100 (FIG. 1). This electronic device includes a processing subsystem 1410, memory subsystem 1412, and networking subsystem 1414. Processing subsystem 1410 may include one or more devices configured to perform computational operations and to control components in system 100 (FIG. 1). For example, processing subsystem 1410 may include one or more microprocessors, one or more graphics processing units (GPUs), application-specific integrated circuits (ASICs), microcontrollers, programmable-logic devices, and/or one or more digital signal processors (DSPs).

Memory subsystem 1412 may include one or more devices for storing data and/or instructions for processing subsystem 1410 and networking subsystem 1414. For example, memory subsystem 1412 may include dynamic random access memory (DRAM), static random access memory (SRAM), and/or other types of memory. In some embodiments, instructions for processing subsystem 1410 in memory subsystem 1412 include one or more program modules 1424 or sets of instructions, which may be executed in an operating environment (such as operating system 1422) by processing subsystem 1410. Note that the one or more computer programs may constitute a computer-program mechanism or a program module (i.e., software). Moreover, instructions in the various modules in memory subsystem 1412 may be implemented in: a high-level procedural language, an object-oriented programming language, and/or in an assembly or machine language. Furthermore, the programming language may be compiled or interpreted, e.g., configurable or configured (which may be used interchangeably in this discussion), to be executed by processing subsystem 1410.

In addition, memory subsystem 1412 may include mechanisms for controlling access to the memory. In some embodiments, memory subsystem 1412 includes a memory hierarchy that comprises one or more caches coupled to a memory in electronic device 1400. In some of these embodiments, one or more of the caches is located in processing subsystem 1410.

In some embodiments, memory subsystem 1412 is coupled to one or more high-capacity mass-storage devices (not shown). For example, memory subsystem 1412 may be coupled to a magnetic or optical drive, a solid-state drive, or another type of mass-storage device. In these embodiments, memory subsystem 1412 may be used by electronic device 1400 as fast-access storage for often-used data, while the mass-storage device is used to store less frequently used data.

In some embodiments, memory subsystem 1412 includes a remotely located archive device. This archive device can be a high-capacity network attached mass-storage device, such as: network attached storage (NAS), an external hard drive, a storage server, a cluster of servers, a cloud-storage provider, a cloud-computing provider, a magnetic-tape backup system, a medical records archive service, and/or another type of archive device. Moreover, processing subsystem 1410 may interact with the archive device via an application programming interface to store and/or access information from the archive device. Note that memory subsystem 1412 and/or electronic device 1400 may be compliant with the Health Insurance Portability and Accountability Act.

Figure 15:
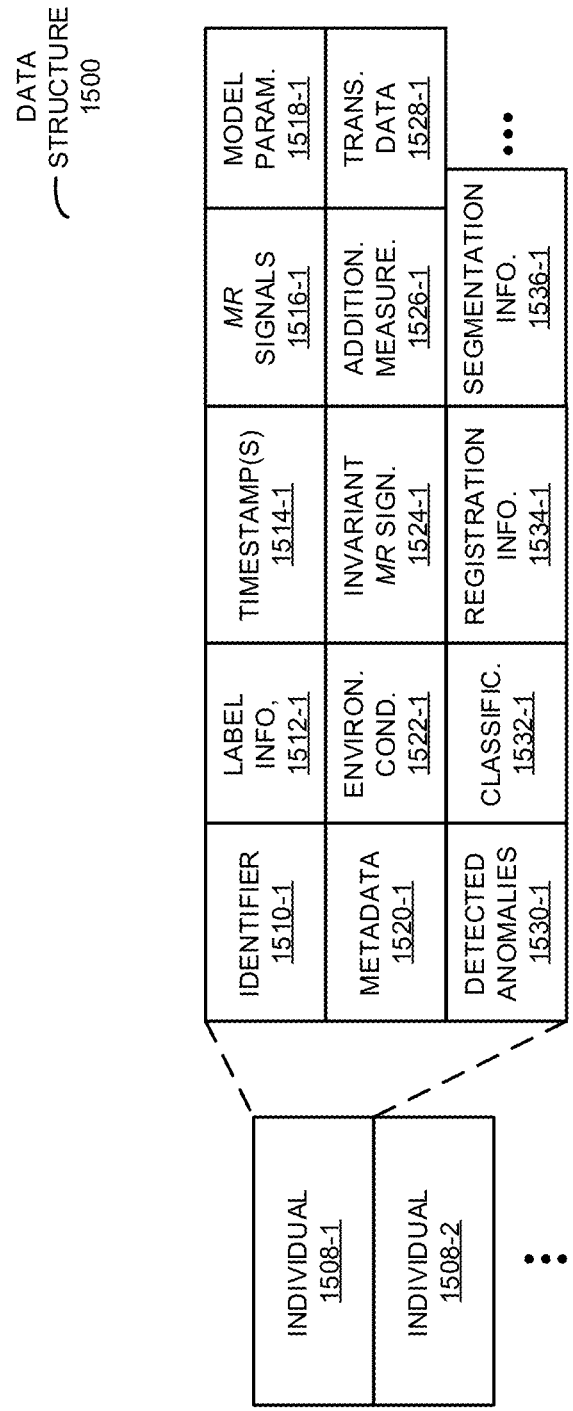
FIG. 15 is a drawing illustrating a data structure that is used by the electronic device of FIG. 14 in accordance with an embodiment of the present disclosure.

An example of the data stored (locally and/or remotely) in memory subsystem 1412 is shown in FIG. 15, which presents a drawing illustrating an example of a data structure 1500 that is used by electronic device 1400 (FIG. 14). This data structure may include: an identifier 1510-1 of individual 1508-1, label information 1512 (such as age, gender, biopsy results and diagnosis if one has already been made and/or any other suitable sample information), timestamps 1514 when data was acquired, received MR signals 1516 (and, more generally, raw data), MR capture and model parameters 1518 (including the voxel size, speed, resonant frequency, $T_1$ and $T_2$ relaxation times, signal processing techniques, RF pulse techniques, magnetic gradient strengths, the variable magnetic field $B_0$, the pulse sequence, etc.), metadata 1520 (such as information characterizing individual 1508-1, demographic information, family history, optional segmentation data, data generated from or in response to the raw data, etc.), environmental conditions 1522 (such as the temperature, humidity and/or barometric pressure in the room or the chamber in which individual 1508-1 was measured), a determined invariant MR signature 1524 (or an MR model), one or more additional measurements 1526 of physical properties of individual 1508-1 (such as weight, dimensions, images, etc.), transformed data 1528 generated from or in response to MR signals 1516 (such as an estimated invariant MR signature), optional detected anomalies 1530 (which, for a particular voxel, may include information specifying one or more of detected anomalies 1530), optional classifications 1532 of detected anomalies 1530, registration information 1534 and/or segmentation information 1536. Note that data structure 1500 may include multiple entries for different scanning instructions.

In one embodiment, data in data structure 1500 is encrypted using a block-chain or a similar cryptographic hash technique to detect unauthorized modification or corruption of records. Moreover, the data can be anonymized prior to storage so that the identity of an individual is anonymous unless the individual gives permission or authorization to access or release the individual's identity.

Referring back to FIG. 14, networking subsystem 1414 may include one or more devices configured to couple to and communicate on a wired, optical and/or wireless network (i.e., to perform network operations and, more generally, communication), including: control logic 1416, an interface circuit 1418, one or more antennas 1420 and/or input/output (I/O) port 1428. (While FIG. 14 includes one or more antennas 1420, in some embodiments electronic device 1400 includes one or more nodes 1408, e.g., a pad or connector, which can be coupled to one or more antennas 1420. Thus, electronic device 1400 may or may not include one or more antennas 1420.) For example, networking subsystem 1414 can include a Bluetooth networking system (which can include Bluetooth Low Energy, BLE or Bluetooth LE), a cellular networking system (e.g., a 3G/4G network such as UMTS, LTE, etc.), a universal serial bus (USB) networking system, a networking system based on the standards described in IEEE 802.11 (e.g., a Wi-Fi networking system), an Ethernet networking system, and/or another networking system.

Moreover, networking subsystem 1414 may include processors, controllers, radios/antennas, sockets/plugs, and/or other devices used for coupling to, communicating on, and handling data and events for each supported networking system. Note that mechanisms used for coupling to, communicating on, and handling data and events on the network for each network system are sometimes collectively referred to as a 'network interface' for network subsystem 1414. Moreover, in some embodiments a 'network' between components in system 100 (FIG. 1) does not yet exist. Therefore, electronic device 1400 may use the mechanisms in networking subsystem 1414 for performing simple wireless communication between the components, e.g., transmitting advertising or beacon frames and/or scanning for advertising frames transmitted by other components.

Within electronic device 1400, processing subsystem 1410, memory subsystem 1412, networking subsystem 1414 may be coupled using one or more interconnects, such as bus 1426. These interconnects may include an electrical, optical, and/or electro-optical connection that the subsystems can use to communicate commands and data among one another. Although only one bus 1426 is shown for clarity, different embodiments can include a different number or configuration of electrical, optical, and/or electro-optical connections among the subsystems.

Electronic device 1400 may be (or can be) included in a wide variety of electronic devices. For example, electronic device 1400 may be included in: a tablet computer, a smartphone, a smartwatch, a portable computing device, test equipment, a digital signal processor, a cluster of computing devices, a laptop computer, a desktop computer, a server, a subnotebook/netbook and/or another computing device.

Although specific components are used to describe electronic device 1400, in alternative embodiments, different components and/or subsystems may be present in electronic device 1400. For example, electronic device 1400 may include one or more additional processing subsystems, memory subsystems, and/or networking subsystems. Additionally, one or more of the subsystems may not be present in electronic device 1400. Moreover, in some embodiments, electronic device 1400 may include one or more additional subsystems that are not shown in FIG. 14.

Although separate subsystems are shown in FIG. 14, in some embodiments, some or all of a given subsystem or component can be integrated into one or more of the other subsystems or components in electronic device 1400. For example, in some embodiments the one or more program modules 1424 are included in operating system 1422. In some embodiments, a component in a given subsystem is included in a different subsystem. Furthermore, in some embodiments electronic device 1400 is located at a single geographic location or is distributed over multiple different geographic locations.

Moreover, the circuits and components in electronic device 1400 may be implemented using any combination of analog and/or digital circuitry, including: bipolar, PMOS and/or NMOS gates or transistors. Furthermore, signals in these embodiments may include digital signals that have approximately discrete values and/or analog signals that have continuous values. Additionally, components and circuits may be single-ended or differential, and power supplies may be unipolar or bipolar.

An integrated circuit may implement some or all of the functionality of networking subsystem 1414 (such as a radio) and, more generally, some or all of the functionality of electronic device 1400. Moreover, the integrated circuit may include hardware and/or software mechanisms that are used for transmitting wireless signals from electronic device 1400 and receiving signals at electronic device 1400 from other components in system 100 (FIG. 1) and/or from electronic devices outside of system 100 (FIG. 1). Aside from the mechanisms herein described, radios are generally known in the art and hence are not described in detail. In general, networking subsystem 1414 and/or the integrated circuit can include any number of radios. Note that the radios in multiple-radio embodiments function in a similar way to the radios described in single-radio embodiments.

While some of the operations in the preceding embodiments were implemented in hardware or software, in general the operations in the preceding embodiments can be implemented in a wide variety of configurations and architectures. Therefore, some or all of the operations in the preceding embodiments may be performed in hardware, in software or both.

In addition, in some of the preceding embodiments there are fewer components, more components, a position of a component is changed and/or two or more components are combined.

While the preceding discussion illustrated the characterization technique to solve a vector wave equation, in other embodiments the characterization technique may be used to solve a scalar equation. For example, an acoustic wave equation may be solved in an arbitrary inhomogeneous media based on ultrasound measurements using a forward model. (Thus, in some embodiments the excitation may be mechanical.) Note that the acoustic coupling in ultrasound measurements can dependent on the operator (i.e., the ultrasound measurements may be pressure dependent). Nonetheless, a similar approach may be used to: improve ultrasound imaging, determine 3D structure, facilitate improved presentation, etc.

In the preceding description, we refer to 'some embodiments.' Note that 'some embodiments' describes a subset of all of the possible embodiments, but does not always specify the same subset of embodiments.

The foregoing description is intended to enable any person skilled in the art to make and use the disclosure, and is provided in the context of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art, and the general principles defined herein may be applied to other embodiments and applications without departing from the spirit and scope of the present disclosure. Additionally, the discussion of the preceding embodiments is not intended to limit the present disclosure. Thus, the present disclosure is not intended to be limited to the embodiments shown, but is to be accorded the widest scope consistent with the principles and features disclosed herein.

What is claimed is:

1. A method for determining model parameters associated with a sample, comprising operations of:
    applying, to the sample, an external magnetic field using a magnet and a radio-frequency pulse sequence using a transmission coil, wherein the external magnetic field is associated with polarization of the sample;
    measuring, using a radio-frequency coil, a non-inductive sensor or both, at least a component of a magnetization response associated with the sample;
    calculating, with a computer that initiates a forward model with multiple voxels that represent the sample, at least a predicted value of the component of the magnetization response that was measured in the measuring operation, wherein the forward model simulates magnetic-resonance response physics occurring within the sample to a given external magnetic field and a given radio-frequency pulse sequence that are selected from a range of measurement conditions that includes the applied external magnetic field and the applied radio-frequency pulse sequence, and at least a different external magnetic field and at least a different radio-frequency pulse sequence,
    wherein the forward model is a function of the applied external magnetic field, the applied radio-frequency pulse sequence, the model parameters of the multiple voxels, and one of: Bloch equations, or Liouvillian computations,
    wherein the model parameters comprise a density of a type of nuclei, a longitudinal relaxation time along a direction parallel to the applied external magnetic field and a transverse relaxation time along a direction perpendicular to the applied external magnetic field, and
    wherein the model parameters are determined without performing a Fourier transform on the measured component of the magnetization response;
    computing, with the computer, a difference between at least the measured component of the magnetization response and at least the calculated predicted value of the component of the magnetization;
    solving, with the computer, an inverse problem as a function of the computed difference in order to determine revisions to the model parameters on a voxel-by-voxel basis;
    iteratively repeating instances of a group of operations comprising the operations of applying, measuring, calculating, computing and solving until the computed difference is less than a predefined value, wherein the magnetization of the sample either has not relaxed to a predefined state or is not reset to the predefined state between the instances of the group of operations, so that the sample has a dynamic magnetization state between at least some adjacent instances of the group of operations; and
    providing the model parameters as an output to a user, another electronic device, a display or memory when the computed difference is less than the predefined value.

2. The method of claim 1, wherein the forward model further comprises an error term associated with the dynamic magnetization of the sample.

3. The method of claim 1, wherein the revisions to the model parameters are based on a Jacobian matrix and use Newton's method.

4. The method of claim 1, wherein the revisions to the model parameters are constrained based on the model parameters that have been determined during at least a previous instance of the group of operations.

5. The method of claim 1, wherein the sample comprises different types of tissue; and
wherein initial values of the model parameters are within predefined parameter ranges for the different types of tissue that are present in the sample.

6. The method of claim 1, wherein the sample comprises different types of tissue; and
wherein the method further comprises segmenting the tissue types that are present in the sample based on discontinuous changes in at least some of the model parameters along a direction between adjacent voxels in the representation of the sample.

7. The method of claim 1, wherein the model parameters are determined sequentially in the instances of the group of operations based on time scales associated with the model parameters; and
wherein a model parameter that has a shortest time scale is determined first.

8. The method of claim 1, wherein the calculation of the component of the magnetization response and the revisions to the model parameters are performed concurrently with the measurement of the component of the magnetization response during a given instance of the group of operations.

9. The method of claim 1, wherein at least one of the applied external magnetic field and the applied radio-frequency pulse sequence is modified between at least two adjacent instances of the group of operations.

10. The method of claim 9, wherein the method further comprises determining the current dynamic magnetization state of the sample using the forward model;
wherein the forward model is a function of the applied external magnetic field and the applied radio-frequency pulse sequence; and
wherein the determined current dynamic magnetization state is used as an initial condition in the calculating and the determining operations that occur in a subsequent instance of the group of operations.

11. The method of claim 1, wherein at least one of a magnitude and a direction of the applied external magnetic field is changed as a function of time during acquisition of the measurement.

12. The method of claim 1, wherein at least one of the applied external magnetic field and the applied radio-frequency pulse sequence is modified between at least two adjacent instances of the group of operations; and
wherein at least the one of the modified applied external magnetic field and the modified applied radio-frequency pulse sequence are selected to reduce the computed difference.

13. A non-transitory computer-readable storage medium for use in conjunction with a computer, the computer-readable storage medium configured to store program instructions that, when executed by the computer, cause the computer to perform operations comprising:
applying, to a sample, an external magnetic field using a magnet and a radio-frequency pulse sequence using a transmission coil, wherein the external magnetic field is associated with polarization of the sample;
measuring, using a radio-frequency coil, a non-inductive sensor or both, at least a component of a magnetization response associated with the sample;
calculating, with the computer that initiates a forward model with multiple voxels that represent the sample, at least a predicted value of the component of the magnetization response that was measured in the measuring operation, wherein the forward model simulates magnetic-resonance response physics occurring within the sample to a given external magnetic field and a given radio-frequency pulse sequence that are selected from a range of measurement conditions that includes the applied external magnetic field and the applied radio-frequency pulse sequence, and at least a different external magnetic field and at least a different radio-frequency pulse sequence,
wherein the forward model is a function of the applied external magnetic field, the applied radio-frequency pulse sequence, model parameters of the multiple voxels, and one of: Bloch equations, or Liouvillian computations,
wherein the model parameters comprise a density of a type of nuclei, a longitudinal relaxation time along a direction parallel to the applied external magnetic field and a transverse relaxation time along a direction perpendicular to the applied external magnetic field, and
wherein the model parameters are determined without performing a Fourier transform on the measured component of the magnetization response;
computing, with the computer, a difference between at least the measured component of the magnetization response and at least the calculated predicted value of the component of the magnetization;
solving, with the computer, an inverse problem as a function of the computed difference in order to determine revisions to the model parameters on a voxel-by-voxel basis;
iteratively repeating instances of a group of operations comprising the operations of applying, measuring, calculating, computing and solving until the computed difference is less than a predefined value, wherein the magnetization of the sample either has not relaxed to a predefined state or is not reset to the predefined state between the instances of the group of operations, so that the sample has a dynamic magnetization state between at least some adjacent instances of the group of operations; and
providing the model parameters as an output to a user, another electronic device, a display or memory when the computed difference is less than the predefined value.

14. The non-transitory computer-readable storage medium of claim 13, wherein the forward model further comprises an error term associated with the dynamic magnetization of the sample.

15. The non-transitory computer-readable storage medium of claim 13, wherein at least one of the applied external magnetic field and the applied radio-frequency pulse sequence is modified between at least two adjacent instances of the group of operations; and
wherein at least the one of the modified applied external magnetic field and the modified applied radio-frequency pulse sequence are selected to reduce the computed difference.

16. The non-transitory computer-readable storage medium of claim 13, wherein the calculation of the component of the magnetization response and the revisions to the model parameters are performed concurrently with the measurement of the component of the magnetization response during a given instance of the group of operations.

17. The non-transitory computer-readable storage medium of claim 13, wherein at least one of the applied external magnetic field and the applied radio-frequency pulse sequence is modified between at least two adjacent instances of the group of operations.

18. The non-transitory computer-readable storage medium of claim 13, wherein at least one of a magnitude and a direction of the applied external magnetic field is changed as a function of time during acquisition of the measurement.

19. A system configured to determine model parameters, comprising:
a magnet and a transmission coil configured to generate magnetic fields;
a measurement device configured to perform measurements, wherein the measurement device comprises: a radio-frequency coil, a non-inductive sensor or both;
a processor, coupled to the magnet, the measurement device and memory, configured to execute program instructions; and
the memory, coupled to the processor, configured to store the program instructions that, when executed by the processor, cause the system to perform operations comprising:
applying, to a sample, an external magnetic field using the magnet and a radio-frequency pulse sequence using the transmission coil, wherein the external magnetic field is associated with polarization of the sample;
measuring, using a measurement device, at least a component of a magnetization response associated with the sample;
calculating, with the processor that initiates a forward model with multiple voxels that represent the sample, at least a predicted value of the component of the magnetization response that was measured in the measuring operation, wherein the forward model simulates magnetic-resonance response physics occurring within the sample to a given external magnetic field and a given radio-frequency pulse sequence that are selected from a range of measurement conditions that includes the applied external magnetic field and the applied radio-frequency pulse sequence, and at least a different external magnetic field and at least a different radio-frequency pulse sequence,
wherein the forward model is a function of the applied external magnetic field, the applied radio-frequency pulse sequence, model parameters of the multiple voxels, and one of: Bloch equations, or Liouvillian computations,
wherein the model parameters comprise a density of a type of nuclei, a longitudinal relaxation time along a direction parallel to the applied external magnetic field and a transverse relaxation time along a direction perpendicular to the applied external magnetic field, and
wherein the model parameters are determined without performing a Fourier transform on the measured component of the magnetization response;
computing, with the processor, a difference between at least the measured component of the magnetization response and at least the calculated predicted value of the component of the magnetization;
solving, with the processor, an inverse problem as a function of the computed difference in order to determine revisions to the model parameters on a voxel-by-voxel basis;
iteratively repeating instances of a group of operations comprising the operations of applying, measuring, calculating, computing and solving until the computed difference is less than a predefined value, wherein the magnetization of the sample either has not relaxed to a predefined state or is not reset to the predefined state between the instances of the group of operations, so that the sample has a dynamic magnetization state between at least some adjacent instances of the group of operations; and
providing the model parameters as an output to a user, another electronic device, a display or the memory when the computed difference is less than the predefined value.

20. The system of claim 19, wherein the operations comprise determining the current dynamic magnetization state of the sample using the forward model;
wherein the forward model is a function of the applied external magnetic field and the applied radio-frequency pulse sequence; and
wherein the determined current dynamic magnetization state is used as an initial condition in the calculating and the determining operations that occur in a subsequent instance of the group of operations.

21. The system of claim 19, wherein at least one of the applied external magnetic field and the applied radio-frequency pulse sequence is modified between at least two adjacent instances of the group of operations; and
wherein at least the one of the modified applied external magnetic field and the modified applied radio-frequency pulse sequence are selected to reduce the computed difference.

22. The system of claim 19, wherein the model parameters are determined sequentially in the instances of the group of operations based on time scales associated with the model parameters; and
wherein a model parameter that has a shortest time scale is determined first.

23. The system of claim 19, wherein the forward model further comprises an error term associated with the dynamic magnetization of the sample.

* * * * *